US009125906B2

(12) United States Patent
Buensuceso et al.

(10) Patent No.: US 9,125,906 B2
(45) Date of Patent: Sep. 8, 2015

(54) TREATMENT OF PERIPHERAL VASCULAR DISEASE USING UMBILICAL CORD TISSUE-DERIVED CELLS

(75) Inventors: Charito S. Buensuceso, North Brunswick, NJ (US); Anthony J. Kihm, Princeton, NJ (US); Sridevi Dhanaraj, Raritan, NJ (US); Roee Atlas, Givatayim (IL); Israel Nur, Moshav Timmorim (IL); Roberto Meidler, Rehovot (IL); Liliana Bar, Rehovot (IL)

(73) Assignee: DePuy Synthes Products, Inc., Raynham, MA (US)

( * ) Notice: Subject to any disclaimer, the term of this patent is extended or adjusted under 35 U.S.C. 154(b) by 280 days.

(21) Appl. No.: 13/206,913

(22) Filed: Aug. 10, 2011

(65) Prior Publication Data
US 2012/0213743 A1    Aug. 23, 2012

Related U.S. Application Data

(63) Continuation-in-part of application No. 11/617,346, filed on Dec. 28, 2006.

(60) Provisional application No. 60/754,366, filed on Dec. 28, 2005.

(51) Int. Cl.
| A61K 35/51 | (2015.01) |
| A61K 45/00 | (2006.01) |
| A61K 38/48 | (2006.01) |
| A61K 45/06 | (2006.01) |
| A61L 27/38 | (2006.01) |
| C12N 5/073 | (2010.01) |
| A61K 38/36 | (2006.01) |

(52) U.S. Cl.
CPC .............. *A61K 38/4833* (2013.01); *A61K 35/51* (2013.01); *A61K 38/363* (2013.01); *A61K 45/06* (2013.01); *A61L 27/3834* (2013.01); *A61L 27/3839* (2013.01); *A61L 27/3886* (2013.01); *A61L 27/3895* (2013.01); *C12N 5/0605* (2013.01); *C12N 2510/00* (2013.01)

(58) Field of Classification Search
CPC . A61K 35/51; A61K 38/363; A61K 38/4833; A61K 45/00; A61K 2300/00; C12N 5/0605; C12N 2510/00
USPC .......................... 424/93.21, 93.7; 435/325, 366
See application file for complete search history.

(56) References Cited

U.S. PATENT DOCUMENTS

| 4,352,883 A | 10/1982 | Lim |
| 4,882,162 A | 11/1989 | Ikada et al. |
| 4,925,677 A | 5/1990 | Feijen |
| 4,963,489 A | 10/1990 | Naughton et al. |
| 5,004,681 A | 4/1991 | Boyse et al. |
| 5,047,055 A | 9/1991 | Bao et al. |
| 5,192,553 A | 3/1993 | Boyse et al. |
| 5,286,632 A | 2/1994 | Jones |
| 5,320,962 A | 6/1994 | Stiles et al. |
| 5,342,761 A | 8/1994 | MacLeod |
| 5,437,994 A | 8/1995 | Emerson et al. |
| 5,443,950 A | 8/1995 | Naughton et al. |
| 5,466,233 A | 11/1995 | Weiner et al. |
| 5,486,359 A | 1/1996 | Caplan et al. |
| 5,589,376 A | 12/1996 | Anderson et al. |
| 5,670,483 A | 9/1997 | Zhang et al. |
| 5,677,181 A | 10/1997 | Parish |
| 5,698,518 A | 12/1997 | Carson et al. |
| 5,707,643 A | 1/1998 | Ogura et al. |
| 5,736,516 A | 4/1998 | Louis |
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,869,079 A | 2/1999 | Wong et al. |
| 5,902,598 A | 5/1999 | Chen et al. |
| 5,902,741 A | 5/1999 | Purchio et al. |
| 5,906,934 A | 5/1999 | Grande et al. |
| 5,919,702 A | 7/1999 | Purchio et al. |
| 5,942,225 A | 8/1999 | Bruder et al. |
| 5,955,343 A | 9/1999 | Holmes et al. |
| 5,962,325 A | 10/1999 | Naughton et al. |
| 5,994,094 A | 11/1999 | Hötten et al. |

(Continued)

FOREIGN PATENT DOCUMENTS

| EP | 0 333 328 | 9/1989 |
| EP | 0 529 751 | 3/1993 |

(Continued)

OTHER PUBLICATIONS

Spotnitz, Am. J. Surg. 182:8S-14S, 2001.*
Brookes, J. Bone and Joint Surgery (42-B):110-125, 1960.*
Al-Khaldi et al, Ann. Thorac. Surg. 75:204-209, 2003.*
Romanov et al, Stem Cells 21:105-110, 2003.*
Lodie et al, Tissue Engineering 8(5):739-751, 2002.*
In the U. S. Patent and Trademark Office, Non-Final Office Action in re: U.S. Appl. No. 11/617,346 dated Aug. 11, 2009, 12 pages.
In the U. S. Patent and Trademark Office, Final Action in re: U.S. Appl. No. 11/617,346 dated Apr. 15, 2010, 7 pages.
In the U. S. Patent and Trademark Office, Final Office Action in re: U.S. Appl. No. 11/617,346 dated Aug. 20, 2010, 12 pages.

(Continued)

*Primary Examiner* — Kevin Hill
(74) *Attorney, Agent, or Firm* — Bernard F. Plantz; Johnson & Johnson

(57) ABSTRACT

Compositions and methods of using cells derived from umbilical cord tissue, to stimulate and support angiogenesis, to improve blood flow, to regenerate, repair, and improve skeletal muscle damaged by a peripheral ischemic event, and to protect skeletal muscle from ischemic damage in peripheral vascular disease patients are disclosed. In particular, methods of treating a patient having a peripheral vascular disease with umbilical derived cells and fibrin glue are disclosed.

28 Claims, 15 Drawing Sheets

(56) References Cited

U.S. PATENT DOCUMENTS

| | | | |
|---|---|---|---|
| 6,001,647 A | 12/1999 | Peck et al. |
| 6,022,743 A | 2/2000 | Naughton et al. |
| 6,059,968 A | 5/2000 | Wolf |
| 6,140,039 A | 10/2000 | Naughton et al. |
| 6,171,610 B1 | 1/2001 | Vacanti et al. |
| 6,200,606 B1 | 3/2001 | Peterson et al. |
| 6,200,806 B1 | 3/2001 | Thomson |
| 6,214,369 B1 | 4/2001 | Grande et al. |
| 6,221,904 B1 | 4/2001 | Agus et al. |
| 6,251,090 B1 | 6/2001 | Avery et al. |
| 6,291,240 B1 | 9/2001 | Mansbridge et al. |
| 6,323,188 B1 | 11/2001 | Weissman |
| 6,326,201 B1 | 12/2001 | Fung et al. |
| 6,331,313 B1 | 12/2001 | Wong et al. |
| 6,333,029 B1 | 12/2001 | Vyakarnam et al. |
| 6,355,239 B1 | 3/2002 | Bruder et al. |
| 6,355,699 B1 | 3/2002 | Vyakarnam et al. |
| 6,358,737 B1 | 3/2002 | Bonewald et al. |
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,497,875 B1 | 12/2002 | Sorrell et al. |
| 6,511,511 B1 | 1/2003 | Slivka et al. |
| 6,528,245 B2 | 3/2003 | Sanchez-Ramos et al. |
| 6,534,084 B1 | 3/2003 | Vyakarnam et al. |
| 6,541,028 B1 | 4/2003 | Kuri-Harcuch et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |
| 8,039,258 B2 | 10/2011 | Harris et al. |
| 8,277,796 B2 | 10/2012 | Messina et al. |
| 8,318,483 B2 | 11/2012 | Mistry et al. |
| 8,703,121 B2 | 4/2014 | Harris et al. |
| 8,815,587 B2 | 8/2014 | Harris et al. |
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0064519 A1 | 5/2002 | Bruder et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1* | 1/2003 | Naughton et al. ........... 424/93.7 |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0028660 A1 | 2/2004 | Hariri et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0136967 A1 | 7/2004 | Weiss et al. |
| 2004/0230309 A1 | 11/2004 | DiMauro et al. |
| 2004/0258670 A1* | 12/2004 | Laughlin et al. ........... 424/93.21 |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1* | 3/2005 | Harmon et al. ............. 424/93.7 |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0118144 A1* | 6/2005 | Zhang ........................ 424/93.7 |
| 2005/0148074 A1 | 7/2005 | Davies et al. |
| 2005/0177249 A1 | 8/2005 | Kladakis et al. |
| 2005/0249731 A1 | 11/2005 | Aslan et al. |
| 2006/0094113 A1 | 5/2006 | Epstein et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2006/0251630 A1 | 11/2006 | Stewart et al. |
| 2006/0275273 A1 | 12/2006 | Seyedin et al. |
| 2007/0009494 A1 | 1/2007 | Mistry et al. |

(56) References Cited

U.S. PATENT DOCUMENTS

| | | |
|---|---|---|
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm |
| 2007/0264269 A1 | 11/2007 | Harmon et al. |
| 2007/0275362 A1 | 11/2007 | Edinger et al. |
| 2008/0050349 A1 | 2/2008 | Stewart |
| 2008/0112939 A1 | 5/2008 | Colter et al. |
| 2008/0145934 A1 | 6/2008 | Harris et al. |
| 2008/0166328 A1 | 7/2008 | Harmon et al. |
| 2008/0305148 A1 | 12/2008 | Fu |
| 2009/0092653 A1 | 4/2009 | Colter et al. |
| 2009/0162411 A1 | 6/2009 | Buensuceso et al. |
| 2009/0166178 A1 | 7/2009 | Harmon et al. |
| 2009/0169597 A1 | 7/2009 | Brown et al. |
| 2010/0158877 A1 | 6/2010 | Colter et al. |
| 2010/0158880 A1 | 6/2010 | Seyda et al. |
| 2010/0159025 A1 | 6/2010 | Kramer et al. |
| 2010/0159588 A1 | 6/2010 | Harmon et al. |
| 2010/0210013 A1 | 8/2010 | Mistry et al. |
| 2010/0215714 A1 | 8/2010 | Messina et al. |
| 2010/0247499 A1 | 9/2010 | Kihm et al. |
| 2010/0260843 A1 | 10/2010 | Messina et al. |
| 2011/0280838 A1 | 11/2011 | Kramer et al. |
| 2012/0315251 A1 | 12/2012 | Harris et al. |
| 2013/0022585 A1 | 1/2013 | Messina et al. |
| 2014/0154226 A1 | 6/2014 | Messina et al. |
| 2015/0064781 A1 | 3/2015 | Mistry et al. |

FOREIGN PATENT DOCUMENTS

| | | |
|---|---|---|
| EP | 0 552 380 | 7/1993 |
| EP | 1 216 718 | 6/2002 |
| EP | 1 316 322 | 6/2003 |
| EP | 1 405 649 | 4/2004 |
| JP | 2003-235549 | 8/2003 |
| JP | 2004-210713 | 7/2004 |
| JP | 2004-254682 | 9/2004 |
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 95/23216 | 8/1995 |
| WO | WO 96/01316 | 1/1996 |
| WO | WO 96/05309 | 2/1996 |
| WO | WO 98/17791 | 4/1998 |
| WO | WO 98/33515 | 8/1998 |
| WO | WO 98/51317 | 11/1998 |
| WO | WO 99/03973 | 1/1999 |
| WO | WO 00/09666 | 2/2000 |
| WO | WO 00/73421 | 12/2000 |
| WO | WO 01/11011 | 2/2001 |
| WO | WO 01/19379 | 3/2001 |
| WO | WO 01/34775 | 5/2001 |
| WO | WO 02/36751 | 5/2002 |
| WO | WO 02/46373 | 6/2002 |
| WO | WO 02/059278 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/054146 | 7/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070922 | 8/2003 |
| WO | WO 03/072728 | 9/2003 |
| WO | WO 03/080822 | 10/2003 |
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 2004/007532 | 1/2004 |
| WO | WO 2004/011012 | 2/2004 |
| WO | WO 2004/011621 | 2/2004 |
| WO | WO 2004/016747 | 2/2004 |
| WO | WO 2004/023100 | 3/2004 |
| WO | WO 2004/072273 | 8/2004 |
| WO | WO 2004/111207 | 12/2004 |
| WO | WO 2005/001076 | 1/2005 |
| WO | WO 2005/001077 | 1/2005 |
| WO | WO 2005/001078 | 1/2005 |
| WO | WO 2005/001079 | 1/2005 |
| WO | WO 2005/001080 | 1/2005 |
| WO | WO 2005/003334 | 1/2005 |
| WO | WO 2005/007176 | 1/2005 |
| WO | WO 2005/021738 | 3/2005 |
| WO | WO 2005/038012 | 4/2005 |
| WO | WO 2005/042703 | 5/2005 |
| WO | WO 2006/071773 | 7/2006 |
| WO | WO 2006/071777 | 7/2006 |
| WO | WO 2006/071778 | 7/2006 |
| WO | WO 2006/071794 | 7/2006 |
| WO | WO 2006/071802 | 7/2006 |
| WO | WO 2006/083394 | 8/2006 |
| WO | WO 2007/070870 | 6/2007 |
| WO | WO 2007/073552 | 6/2007 |
| WO | WO 2007/076522 | 7/2007 |
| WO | WO 2007/108003 | 9/2007 |
| WO | WO 2008/008229 | 1/2008 |
| WO | WO 2008/036447 | 3/2008 |
| WO | WO 2008/045498 | 4/2008 |
| WO | WO 2008/060541 | 5/2008 |
| WO | WO 2008/085221 | 7/2008 |
| WO | WO 2009/046335 | 4/2009 |
| WO | WO 2009/085860 | 7/2009 |
| WO | WO 2010/006219 | 1/2010 |
| WO | WO 2010/071862 | 6/2010 |
| WO | WO 2010/071863 | 6/2010 |
| WO | WO 2010/071864 | 7/2010 |
| WO | WO 2010/080364 | 7/2010 |
| WO | WO 2010/111663 | 9/2010 |
| WO | WO 2012/158952 A1 | 11/2012 |
| WO | WO 2013/022447 A1 | 2/2013 |

OTHER PUBLICATIONS

In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.

(56) References Cited

OTHER PUBLICATIONS

In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U. S. Patent and Trademark Office, Non-Final Office Action in re: U.S. Appl. No. 11/322,372 dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the U. S. Patent and Trademark Office, Final Office Action in re: U.S. Appl. No. 11/315,898, dated Sep. 16, 2008, 8 pages.
In the U. S. Patent and Trademark Office, Non-Final Office Action in re: U.S. Appl. No. 11/323,372, dates Sep. 3, 2008, 45 pages.
In the U. S. Patent and Trademark Office, Non-Final Office Action in re: U.S. Appl. No. 11/317,574, dated Sep. 30, 2008, 23 pages.
In the U. S. Patent and Trademark Office, Final Office Action in re: U.S. Appl. No. 11/315,969, dated Dec. 23, 2008, 11 pages.
In the U. S. Patent and Trademark Office, Non-Final Office Action in re: U.S. Appl. No. 10/951,357, dated Nov. 26, 2008, 19 pages.
In the U. S. Patent and Trademark Office, Final Office Action in re: U.S. Appl. No. 11/321,864, dated Jan. 8, 2009, 10 pages.
In the U. S. Patent and Trademark Office, Final Office Action in re: U.S. Appl. No. 11/321,863, dated Feb. 12, 2009, 15 pages.
In the U. S. Patent and Trademark Office, Non-Final Office Action in re: U.S. Appl. No. 11/315,943, dated Feb. 20, 2009, 9 pages.
In the U. S. Patent and Trademark Office, Final Office Action in re: U.S. Appl. No. 10/877,445, dated Mar. 19, 2009, 15 pages.
In the U. S. Patent and Trademark Office, Non-Final Office Action in re: U.S. Appl. No. 11/481,481, dated Mar. 20, 2009, 12 pages.
In the U. S. Patent and Trademark Office, Final Office Action in re: U.S. Appl. No. 11/315,897, dated Mar. 20, 2009, 13 pages.
In the U. S. Patent and Trademark Office, Non-Final Office Action in re: U.S. Appl. No. 11/481,480, dated Mar. 20, 2009, 13 pages.
In the U. S. Patent and Trademark Office, Final Office Action in re: U.S. Appl. No. 11/322,003 dated Feb. 13, 2009, 17 pages.
In the U. S. Patent and Trademark Office, Final Office Action in re: U.S. Appl. No. 10/876,998 dated Feb. 13, 2009, 10 pages.
In the U. S. Patent and Trademark Office, Final Office Action in re: U.S. Appl. No. 11/322,372 dated Feb. 13, 2009, 14 pages.
In the U. S. Patent and Trademark Office, Non-Final Office Action in re: U.S. Appl. No. 11/315,898 dated Feb. 18, 2009, 10 pages.
In the U. S. Patent and Trademark Office, Non-Final Office Action in re: U.S. Appl. No. 11/304,091 dated Feb. 27, 2009, 11 pages.
In the U. S. Patent and Trademark Office, Non-Final Office Action in re: U.S. Appl. No. 11/481,456 dated Apr. 16, 2009, 14 pages.
In the U. S. Patent and Trademark Office, Final Office Action in re: U.S. Appl. No. 11/317,574 dated Apr. 29, 2009, 21 pages.
In the U. S. Patent and Trademark Office, Non-Final Office Action in re: U.S. Appl. No. 11/871,045 dated Apr. 27, 2009, 7 pages.
In the U. S. Patent and Trademark Office, Advisory Action in re: U.S. Appl. No. 11/315,969 dated Sep. 29, 2009, 9 pages.
In the U. S. Patent and Trademark Office, Advisory Action in re: U.S. Appl. No. 11/322,372 dated May 12, 2009, 10 pages.
In the U. S. Patent and Trademark Office, Non-Final Office Action in re: U.S. Appl. No. 10/877,446 dated Jun. 12, 2009, 16 pages.
In the U. S. Patent and Trademark Office, Final Office Action in re: U.S. Appl. No. 11/304,091 dated Jul. 8, 2009, 11 pages.
In the U. S. Patent and Trademark Office, Final Office Action in re: U.S. Appl. No. 11/322,372 dated Aug. 6, 2009, 12 pages.
In the U. S. Patent and Trademark Office, Final Office Action in re: U.S. Appl. No. 11/481,456 dated Oct. 9, 2009, 11 pages.
In the U. S. Patent and Trademark Office, Non-Final Office Action in re: U.S. Appl. No. 11/612,872 dated Oct. 2, 2009, 9 pages.
In the U. S. Patent and Trademark Office, Final Office Action in re: U.S. Appl. No. 10/877,445 dated Aug. 25, 2009, 18 pages.
In the U. S. Patent and Trademark Office, Final Office Action in re: U.S. Appl. No. 11/321,863 dated Aug. 7, 2009, 11 pages.
In the U. S. Patent and Trademark Office, Final Office Action in re: U.S. Appl. No. 11/321,864 dated Aug. 17, 2009, 13 pages.
In the U. S. Patent and Trademark Office, Non-Final Office Action in re: U.S. Appl. No. 11/871,045 dated Nov. 30, 2009, 7 pages.
In the U. S. Patent and Trademark Office, Final Office Action in re: U.S. Appl. No. 11/315,969 dated May 13, 2009, 11 pages.
In the U. S. Patent and Trademark Office, Non-Final Office Action in re: U.S. Appl. No. 11/317,574 dated Dec. 28, 2009, 26 pages.
In the U. S. Patent and Trademark Office, Non-Final Office Action in re: U.S. Appl. No. 11/321,863 dated Jan. 7, 2010, 13 pages.
In the U. S. Patent and Trademark Office, Non-Final Office Action in re: U.S. Appl. No. 11/321,864 dated Jan. 27, 2010, 12 pages.
In the U. S. Patent and Trademark Office, Non-Final Office Action in re: U.S. Appl. No. 11/315,969 dated Jan. 27, 2010, 12 pages.
In the U. S. Patent and Trademark Office, Non-Final Office Action in re: U.S. Appl. No. 11/315,943 dated Feb. 19, 2010, 13 pages.

(56) References Cited

OTHER PUBLICATIONS

In the U. S. Patent and Trademark Office, Final Office Action in re: U.S. Appl. No. 11/316,104 dated Mar. 24, 2010, 12 pages.
In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Final Office Action in re: U.S. Appl. No. 11/315,897 dated May 14, 2010, 13 pages.
In the U. S. Patent and Trademark Office, Non-Final Office Action in re: U.S. Appl. No. 11/481,480 dated May 17, 2010, 10 pages.
In the U. S. Patent and Trademark Office, Final Office Action in re: U.S. Appl. No. 11/871,045 dated Jun. 3, 2010, 7 pages.
In the U. S. Patent and Trademark Office, Final Office Action in re: U.S. Appl. No. 11/612,872 dated May 26, 2010, 11 pages.
In the U. S. Patent and Trademark Office, Final Office Action in re: U.S. Appl. No. 10/877,445 dated Jul. 8, 2010, 20 pages.
In the U. S. Patent and Trademark Office, Non-Final Office Action in re: U.S. Appl. No. 10/876,998 dated Aug. 3, 2010, 14 pages.
In the U. S. Patent and Trademark Office, Final Office Action in re: U.S. Appl. No. 11/321,863 dated Aug. 17, 2010, 15 pages.
In the U. S. Patent and Trademark Office, Final Office Action in re: U.S. Appl. No. 11/321,864 dated Aug. 31, 2010, 7 pages.
In the U. S. Patent and Trademark Office, Final Office Action in re: U.S. Appl. No. 11/315,969 dated Aug. 31, 2010, 6 pages.
In the U. S. Patent and Trademark Office, Final Office Action in re: U.S. Appl. No. 11/322,372 dated Aug. 31, 2010, 11 pages.
In the U. S. Patent and Trademark Office, Non-Final Office Action in re: U.S. Appl. No. 12/245,571 dated Sep. 15, 2010, 8 pages.
In the U. S. Patent and Trademark Office, Non-Final Office Action in re: U.S. Appl. No. 11/316,104 dated Sep. 21, 2010, 13 pages.
In the U. S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 11/939,360 dated Oct. 7, 2010, 4 pages.
In the U. S. Patent and Trademark Office, Non-Final Office Action in re: U.S. Appl. No. 12/054,718 dated Sep. 29, 2010, 18 pages.
In the U. S. Patent and Trademark Office, Non-Final Office Action in re: U.S. Appl. No. 11/322,372 dated Jan. 21, 2010, 10 pages.
In the U. S. Patent and Trademark Office, Final Office Action in re: U.S. Appl. No. 11/481,481 dated Sep. 18, 2009, 11 pages.
In the U. S. Patent and Trademark Office, Advisory Action in re: U.S. Appl. No. 11/315,897 dated Jun. 30, 2009, 3 pages.
In the U. S. Patent and Trademark Office, Non-Final Action in re: U.S. Appl. No. 11/315,897 dated Sep. 2, 2009, 12 pages.
In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Non-Final Action in re: U.S. Appl. No. 11/316,104 dated Oct. 31, 2008, 15 pages.
In the U. S. Patent and Trademark Office, Final Action in re: U.S. Appl. No. 10/876,998 dated May 27, 2009, 14 pages.
In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.
In the U. S. Patent and Trademark Office, Non-Final Action in re: U.S. Appl. No. 12/337,439 dated Jan. 6, 2011, 11 pages.
In the U. S. Patent and Trademark Office, Non-Final Action in re: U.S. Appl. No. 10/876,998 dated Feb. 1, 2011, 11 pages.
In the U. S. Patent and Trademark Office, Non-Final Action in re: U.S. Appl. No. 11/481,456 dated Feb. 3, 2011, 10 pages.
In the U. S. Patent and Trademark Office, Non-Final Action in re: U.S. Appl. No. 11/481,481 dated Feb. 3, 2011, 10 pages.
In the U. S. Patent and Trademark Office, Non-Final Action in re: U.S. Appl. No. 12/389,305 dated Feb. 8, 2011, 14 pages.
In the U. S. Patent and Trademark Office, Non-Final Action in re: U.S. Appl. No. 11/481,480 dated Feb. 3, 2011, 10 pages.
In the U.S. Patent and Trademark Office, Final Office Action in re: U.S. Appl. No. 10/877,446 dated Nov. 2, 2011, 12 pages.
In the U.S. Patent and Trademark Office, Non-Final Office Action in re: U.S. Appl. No. 12/339,872 dated Oct. 7, 2011, 8 pages.
In the U.S. Patent and Trademark Office, Non-Final Office Action in re: U.S. Appl. No. 12/748,170 dated May 21, 2012, 7 pages.
In the U.S. Patent and Trademark Office, Final Office Action in re: U.S. Appl. No. 12/389,305 dated Oct. 12, 2011, 12 pages.
In the U.S. Patent and Trademark Office, Final Office Action in re: U.S. Appl. No. 12/429,849 dated Mar. 20, 2012, 9 pages.
In the U.S. Patent and Trademark Office, Non-Final Office Action in re: U.S. Appl. No. 12/642,773 dated Mar. 29, 2012, 28 pages.
In the U. S. Patent and Trademark Office, Final Action in re: U.S. Appl. No. 11/481,456 dated Oct. 11, 2011, 6 pages.
In the U.S. Patent and Trademark Office, Final Action in re: U.S. Appl. No. 11/481,456 dated Nov. 2, 2011, 10 pages.
In the U.S. Patent and Trademark Office, Non-Final Office Action in re: U.S. Appl. No. 12/697,081 dated Apr. 2, 2012.
In the U.S. Patent and Trademark Office, Non-Final Office Action in re: U.S. Appl. No. 12/642,774 dated Jul. 17, 2012, 9 pages.
In the U.S Patent and Trademark Office, Final Office Action in re: U.S. Appl. No. 12/642,773 dated Sep. 13, 2012, 21 pages.
"Cell Isolation Theory", in Tissue Dissociation Guide, Worthington Biochemical, accessible at http://www.tissuedissociation.com, accessed Aug. 8, 2007.
"Cell Lysis, p. 2" http://www.piercenet.com/objects/view.cfm?type=Page&ID=1904ED25-8FA4-475C-8068-C2EB13D5F4E7; accessed Aug. 7, 2008.
"Unigene Entry for Hs.522632, *Homo sapiens* TMP Metallopeptidase Inhibitor 1 (TIMP1)," printed from http://www.ncbi.nlm.nih.gov/UniGene on Oct. 12, 2006.
Aboody, K.S. et al., "Neural Stem Cells Display Extensive Tropism for Pathology in Adult Brain: Evidence From Intracranial Gliomase," *PNAS*, 2000; 97(23):12846-12851.
Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.
Age-Related Eye Disease Study Research Group, "A Randomized, Placebo-Controlled, Clinical Trial of High-Dose Supplementation With Vitamins C and E, Beta Carotene, and Zinc for Age-Related Macular Degeneration and Vision Loss," AREDS Report No. 8, *Arch Ophthalmol.*, 2001; 119(10): 1417-1436.
Aggarwal et al., "Human Mesenchymal Stem Cells Modulate Allogeneic Immune Cell Responses," *Blood*, 2005; 105(4):1815-1822.
Aldskogius, H. et al., "Strategies for Repair of the Deafferented Spinal Cord," *Brain Res. Rev.*, 2002; 40:301-308.
Allcock, H.R. et al., "Synthesis of Poly[(Amino Acid Alkyl Ester)Phosphazenes]1-3," *Macromolecules*, 1977; 10(4):824-830.
Altman, G.H. et al., "Advanced Bioreactor With Controlled Application of Multi-Dimensional Strain for Tissue Engineering," *J. Biomech. Eng.*, 2002; 124:742-749.
Altman, R.D. et al., "Radiographic Assessment of Progression in Osteoarthritis," *Arthritis & Rheum.*, 1987; 30(11):1214-1225.
Anseth, K.S. et al., "In Situ Forming Degradable Networks and Their Application in Tissue Engineering and Drug Delivery," *J. of Controlled Release*, 2002; 78:199-209.
Armulik, A. et al., "Endothelial/Pericyte Interactions," *Circ. Res.*, 2005; 97:512-523.
Aston, J. E., et al., "Repair of Articular Surfaces by Allografts of Articular and Growth-Plate Cartilage," *Journal of Bone and Joint Surgery*, 1986; 68-B(1):29-35.
Auda-Boucher, G. et al., "Staging of the Commitment of Murine Cardiac Cell Progenitors," *Dev. Bio.*, 2000; 225(1):214-225.
Avital, I. et al., "Isolation, Characterization, and Transplantation of Bone Marrow-Derived Hepatocyte Stem Cells," *Biochem. & Biophys. Res. Comm.*, 2001; 288:156-164.
Azizi, S.A. et al., "Engraftment and Migration of Human Bone Marrow Stromal Cells Implanted in the Brains of Albino Rats—Similarities to Astrocyte Grafts," *Proc. Natl. Acad. Sci. USA*, 1998; 95:3908-3913.

(56) References Cited

OTHER PUBLICATIONS

Bai, M., et al., "Dimerization of the Extracellular Calcium-sensing Receptor (CaR) on the Cell Surface of CaR-Transfected HEK293 Cells," *J. Biol Chem.*, 1998; 273(36): 23605-23610.

Baker, K.A. et al., "Intrastriatal and Intranigral Grafting of hNT Neurons in the 6-OHDA Rat Model of Parkinson's Disease," *Exper. Neurol.*, 2000; 162:350-360.

Balis, F. et al., "Central Nervous System Pharmacology of Antileukemic Drugs," *Am. J. of Pediatric Hematol. Oncol.*, 1989; 11(1):74-86.

Balkema, G.W. et al., "Impaired Visual Thresholds in Hypopigmented Animals," Visual Neuroscience, 1991; 6:577-585.

Bao, Z.Z. et al., "Regulation of Chamber-Specific Gene Expression in the Developing Heart by IrX 4," *Science*, 1999; 283(5405):1161-1164 (Abstract 1 page).

Barberi, T. et al., "Neural Subtype Specification of Fertilization and Nuclear Transfer Embryonic Stem Cells and Application in Parkinsonian Mice," *Nature Biotechnology*, 2003; 21(10):1200-1207.

Bartholomew, A. et al., "Mesenchymal stem cells suppress lymphocyte proliferation in vitro and prolong skin graft survival in vivo," Exp Hematol, 2002, 30:42-48.

Beck, R.W. et al., "A Clinical Comparison of Visual Field Testing With a New Automated Perimeter, the Humphrey Field Analyzer, and the Goldmann Perimeter," *Ophthalmology*, 1985; 92(1):77-82.

Bergers, G. et al., "The Role of Pericytes in Blood-Vessel Formation and Maintenance," Neuro-Oncology, 2005; 7:452-464.

Bergers, G. et al., "Cell Factories for Fighting Cancer," Nature Biotechnology, 2001; 19:20-21.

Bhindi, R. et al., "Rat Models of Myocardial Infarction," *Thromb Haemost*, 2006; 96:602-610.

Björklund, L.M. et al., "Embryonic Stem Cells Develop Into Functional Dopaminergic Neurons After Transplantation in a Parkinson Rat Model," PNAS, 2002; 99(4):2344-2349.

Blakemore et al., "Modelling Large Areas of Demyelination in the Rat Reveals the Potential and Possible Limitations of Transplanted Glial Cells for Remyelination in the CNS," *GLIA*, 2002; 38:155-168.

Bradley, B.A., "The Role of HLA Matching in Transplantation," *Immunol. Lett.*, 1991; 29:55-59.

Brodsky, S.V., "Coagulation, Fibrinolysis and Angiogenesis: New Insights From Knockout Mice," *Exp. Nephrol.*, 2002; 10:299-306.

Brooks, P., "Inflammation as an Important Feature of Osteoarthritis," *Bull. World Health Org.*, 2003; 81(9):689-690.

Brown, J.A. et al., "Blockade of Programmed Death-1 Ligands on Dendritic Cells Enhances T Cell Activation and Cytokine Production," *J. Immunology*, 2003; 170:1257-1266.

Bruder et al., "Mesenchymal Stem Cell Surface Antigen SB-10 Corresponds to Activated Leukocyte Cell Adhesion Molecule and Is Involved in Osteogenic Differentiation," *Journal of Bone and Mineral Research*, 1998; 13(4):655-663.

Burnstein, R.M. et al., "Differentiation and Migration of Long Term Expanded Human Neural Progenitors in a Partial Lesion Model of Parkinson's Disease," *Intern. J. of Biochem. & Cell Biology*, 2004; 36:702-713.

Bussolati et al., "Isolation of Renal Progenitor Cells from Adult Human Kidney," *American Journal of Pathology*, 2005; 166(2):545-555.

Caballero, S. et al., "The Many Possible Roles of Stem Cells in Age-Related Macular Degeneration," *Graefe's Arch. Clin. Exp. Ophthalmol.*, 2004; 242:85-90.

Campbell, I.K. et al., "Human Articular Cartilage and Chondrocytes Produce Hemopoietic Colony-Stimulating Factors in Culture in Response to IL-1," *J. of Immun.*, 1991; 147(4):1238-1246.

Can et al., "Concise Review: Human Umbilical Cord Stroma with Regard to the Source of Fetus-Derived Stem Cells," Stem Cells, 2007; 25:2886-2895.

Cao, Q. et al., "Stem Cell Repair of Central Nervous System Injury," *J. of Neuroscience Res.*, 2002; 68:501-510.

Caplan, A.I. et al., "Mesenchymal Stem Cells: Building Blocks for Molecular Medicine in the 21st Century," Trends in Molecular Med., 2001; 7(6):259-264.

Capoccia, B. J. et al, "Bone Marrow-Derived Aldehyde Dehdrogenase Expressing Cells Possess Endothelial Progenitor Function in Addition to Hematopoietic Repopulating Ability and Aid in Blood Flow Recovery after Acute Ischemic Injury," Blood, 2005; 106(11): 747A, Abstract No. 2663.

Carter, D. et al., "Characterization of MSC Potential to Treat GVHD Using Molecular Markers Linked to MSC-Mediated Immunosuppression in Vitro," *Blood*, 2005; 106(11) part 2, Abstract No. 4322, 160B.

Chagraoui, J. et al., "Fetal Liver Stroma Consists of Cells in Epithelial-To-Mesenchymal Transition," *Blood*, 2003; 101(8):2973-2982.

Chen, D. et al. "Differential Roles for Bone Morphogenic Protein (BMP) Receptor Type IB and IA in Differentiation and Specification of Mesenchymal Precursor Cells to Osteoblast and Adipocyte Lineages," *J. Cell Biol.*, 1998; 142(1):295-305.

Chen, H. et al., "The Effect of Hypothermia on Transient Middle Cerebral Artery Occlusion in the Rat," *J. Cereb. Blood Flow Metab.*, 1992; 12(4):621-628.

Chen, J. et al., "Therapeutic Benefit of Intravenous Administration of Bone Marrow Stromal Cells after Cerebral Ischemia in Rats," *Stroke*, 2001; 32(4):1005-1011.

Chen, J. et al., "Intravenous Administration of Human Umbilical cord Blood Reduces Behavioral Deficits After Stroke in Rats," Stroke, 2001; 32:2682-2688.

Chen, ST. et al., "A model of focal ischemic stroke in the rat: reproducible extensive cortical infarction," Stroke, 1986; 17: 738-743.

Cheng, A. et al. "Nitric Oxide Acts in a Positive Feedback Loop With BDNF to Regulate Neural Progenitor Cell Proliferation and Differentiation in the Mammalian Brain," Dev. Biol., 2003; 258:319-333.

Cho, H. J. et al, "Regulation of endothelial cell and endothelial progenitor cell survival and vasculogenesis by integrin-linked kinase," Arterioscler Thromb Vasc Biol, 2005; 25: 1154-60.

Constantini, S. et al., "The Effects of Methylprednisolone and the Ganglioside GM1 on Acute Spinal Cord Injury in Rats," *J. Neurosurg.*, 1994; 80(1):97-111.

Coumans, B. et al., "Lymphoid Cell Apoptosis Induced by Trophoblastic Cells: A Model of Active Foeto-Placental Tolerance," *J. of Immunological Methods*, 1999; 224:185-196.

Curcio, C. et al., "Photoreceptor Loss in Age-Related Macular Degeneration", *Investigative Ophthalmology & Visual Science*, 1996; 37(7): 1236-1249.

D'Cruz, P.M. et al., "Mutation of the Receptor Tyrosine Kinase Gene Mertk in the Retinal Dystrophic RCS Rat," *Hum. Mol. Genet.*, 2000; 9(4):645-651.

Daley, G.Q. et al., "Realistic Prospects for Stem Cell Therapeutics," *Hematol.*, 2003; 398-418.

Danon, D. et al., "Macrophage Treatment of Pressure Sores in Paraplegia," *J. Wound Care*, 1998; 7(6):281-283.

Danon, D. et al., "Treatment of Human Ulcers by Application of Macrophages Prepared From a Blood Unit," *Exp. Gerontol.*, 1997; 32(6):633-641.

Dawson, T.M. et al., "Neuroprotective and Neurorestorative Strategies for Parkinson's Disease," *Nat. Neurosci.*, 2002; 5 Suppl.:1058-1061.

del Monte, F. et al., "Improvement in Survival and Cardiac Metabolism After Gene Transfer of Sarcoplasmic Reticulum $Ca^{2+}$-ATPase in a Rat Model of Heart Failure," *Circulation*, 2001;104:1424-1429.

Diao et al, "Human Umbilical Cord Mesenchymal Stem Cells: Osteogenesis In Vivo as Seed Cells for Bone Tissue Engineering," J. BioMed Mater Res., 2009; 91A:123-131.

Dickinson, A.M. et al., "Non-HLA Immunogenetics in Hematopoietic Stem Cell Transplantation," *Curr. Opin. Immunol.*, 2005; 17(5):517-525.

Dimri, G.P. et al., "A Biomarker That Identifies Senescent Human Cells in Culture and in Aging Skin In Vivo," *Proc. Natl. Acad. Sci. USA*, 1995; 92:9363-9367.

Domb, A. et al., "Degradable Polymers for Site-Specific Drug Delivery," *Polymers for Advanced Technologies*, 1992; 3:279-292.

(56) References Cited

OTHER PUBLICATIONS

Doshi, S.N. et al., "Evolving Role of Tissue Factor and Its Pathway Inhibitor," *Critical Care Med.*, 2002; 30(5):S241-S250.

Doyle, J., "Spiraling Complexity, Robustness, and Fragility in Biology," http://www.cds.caltech.edu/~doyle/CmplxNets/Bio1.pdf, available online Feb. 28, 2004.

Draper et al., "Surface Antigens of Human Embryonic Stem Cells: Changes Upon Differentiation in Culture," *J. Anat.*, 2002; 200:249-258.

Du, Y. et al., "Functional Reconstruction of Rabbit Corneal Epithelium by Human Limbal Cells Cultured on Amniotic Membrane," *Molecular Vision*, 2003; 9:635-643.

Dykens, J. et al., "Photoreceptor Preservation in the S334ter Model of Retinitis Pigmentosa by a Novel Estradiol Analog", *Biochemical Pharmacology*, 2004; 68: 1971-1984.

Eagle, H., "The Specific Amino Acid Requirements of a Mammalian Cell (Strain L) in Tissue Culture," *J. Biol. Chem.*, 1955; 214:839-852.

Eblenkamp, M. et al., "Umbilical Cord Stromal Cells (UCSC). Cells Featuring Osteogenic Differentiation Potential," *Der Orthopade*, Dec. 2004; 33:1338-1345 (English abstract on p. 1339).

Edelstein, M. L. et al., "Gene Therapy Clinical Trials Worldwide 1989-2004—An Overview," *J. Gene Med.*, 2004; 6(6):597-602.

Edlund, H., "Pancreatic Organogenesis—Developmental Mechanisms and Implications for Therapy," *Nat. Rev. Genet.*, 2002; 3:524-532.

Efrat, S. et al., "Cell Replacement Therapy for Type 1 Diabetes," *Trends in Molecular Medicine*, 2002; 8(7):334-339.

Ehtesham, M. et al., "Induction of Glioblastoma Apoptosis Using Neural Stem Cell-Mediated Delivery of Tumor Necrosis Factor-Related Apoptosis-Inducing Ligand," *Cancer Res.*, 2002; 62:7170-7174.

Ehtesham, M. et al., "The Use of Interleukin 12-Secreting Neural Stem Cells for the Treatment of Intracranial Glioma," *Cancer Res.*, 2002; 5657-5663.

Eisenhofer, G.E. et al., "Tyrosinase: A Developmentally Specific Major Determinant of Peripheral Dopamine," *FASEB J.*, 2003; 17:1248-1255.

Ende, N. et al., "Parkinson's Disease Mice and Human Umbilical Cord Blood," *J. Med.*, 2002; 33(1-4):173-180.

Engstad, C.S. et al., "The Effect of Soluble β-1,3-Glucan and Lipopolysaccharide on Cytokine Production and Coagulation Activation in Whole Blood," *Int. Immunopharmacol.*, 2002; 2:1585-1597.

Enzmann, V. et al., "Enhanced Induction of RPE Lineage Markers in Pluripotent Neural Stem Cells Engrafted Into the Adult Rat Subretinal Space," *Investig. Ophthalmol. Visual Sci.*, 2003; 44:5417-5422.

Erices et al., Mesenchymal Progenitor Cells in Human Umbilical Cord Blood, *Br. J. Haematol.*, 2000; 109(1):235-42.

Fazleabas, A.T. et al., "Endometrial Function: Cell Specific Changes in the Uterine Environment," Mol. & Cellular. Endo., 2002; 186:143-147.

Fernandes, A.M. et al., "Mouse Embryonic Stem Cell Expansion in a Microcarrier-based Stirred Culture System," *Journal of Biotechnology*, 2007; 132(2): 227-236.

Fiegel, H.C. et al., "Liver-Specific Gene Expression in Cultured Human Hematopoietic Stem Cells," *Stem Cells*, 2003;21:98-104.

Fields, G.B.,"Induction of Protein-Like Molecular Architecture by Self-Assembly Processes," *Bioorg. Med. Chem.*, 1999; 7(1):75-81.

Fischer, D. et al., "Lens-Injury-Stimulated Axonal Regeneration Throughout the Optic Pathway of Adult Rats," *Exp. Neurol.*, 2001; 172:257-272.

Foley, A. et al., "Heart Induction: Embryology to Cardiomyocyte Regeneration," Trends Cardiovasc. Med., 2004; 14(3):121-125.

Franc, S. et al., "Microfibrillar Composition of Umbilical Cord Matrix : Characterization of Fibrillin, Collagen VI and Intact Collagen V," *Placenta*, 1988; 19:95-104.

Freed, C.R. et al., "Transplantation of Embryonic Dopamine Neurons for Severe Parkinson's Disease," *N. Engl. J. Med.*, 2001; 344(10):710-719.

Frenkel, O. et al., "Activated Macrophages for Treating Skin Ulceration: Gene Expression in Human Monocytes After Hypo-Osmotic Shock," *Clin. Exp. Immunol.*, 2002; 128:59-66.

Friedman, J.A. et al., "Biodegradable Polymer Grafts for Surgical Repair of the Injured Spinal Cord," *Neurosurgery*, 2002; 51(3):742-751.

Fukuchi, Y. et al., "Human Placenta-Derived Cells Have Mesenchymal Stem/Progenitor Cell Potential," *Stem Cells*, 2004; 22:649-658.

Fukuda, K., "Reprogramming of Bone Marrow Mesenchymal Stem Cells Into Cardiomyocytes," *C.R. Biol.*, 2002; 325:1027-1038.

Gellersen, B. et al., "Cyclic AMP and Progesterone Receptor Cross-Talk in Human Endometrium: A Decidualizing Affair," *J. Endocrinol.*, 2003; 178(3):357-372.

Gerdes, D. et al., "Cloning and Tissue Expression of Two Putative Steroid Membrane Receptors," *Biol. Chem.*, 1998; 379:907-911.

Gökhan, S. et al., "Basic and Clinical Neuroscience Applications of Embryonic Stem Cells," *Anat. Rec. (New Anat)*, 2001; 265:142-156.

Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001; 7: 581-588.

Gosiewska, A. et al., "Development of a Three-Dimensional Transmigration Assay for Testing Cell-Polymer Interactions for Tissue Engineering Applications," *Tissue Eng.*, 2001; 7(3):267-277.

Gottleib, D.I. "Large-Scale Sources of Neural Stem Cells," *Annu. Rev. Neurosci.*, 2002; 25:381-407.

Gröhn, P. et al., "Collagen-Coated $BA^{2+}$-Alginate Microcarriers for the Culture of Anchorage-Dependent Mammalian Cells," *Bio Techniques*, 1997; 22(5): 970-975.

Gupta, S. et al., "Isolation and Characterization of Kidney-Derived Stem Cells," *J. of Am. Soci. of Nephrol.*, 2006; 17(11):3028-3040.

Halvorsen, Y.C. et al., "Extracellular Matrix Mineralization and Osteoblast Gene Expression by Human Adipose Tissue-Derived Stromal Cells," *Tissue Eng.*, 2001; 7(6):729-741.

Hanahan, D. "Heritable Formation of Pancreatic β-Cell Tumours in Transgenic Mice Expressing Recombinant Insulin/Simian Virus 40 Oncogenes," *Nature*, 1985; 315:115-122.

Hartgerink, J.D. et al., "Peptide-Amphiphile Nanofibers: A Versatile Scaffold for the Preparation of Self-Assembling Materials," *PNAS*, 2002; 99(8):5133-5138.

Haruta, M. et al., "In Vitro and In Vivo Characterization of Pigment Epithelial Cells Differentiated From Primate Embryonic Stem Cells," *Investig. Ophthalmol. & Visual Sci.*, 2004; 45(3):1020-1025.

Hayflick, L., "The Longevity of Cultured Human Cells," *J. Am. Geriatr. Soc.*, 1974; 22(1):1-12.

Hayflick, L., "The Strategy of Senescence," *Gerontologist*, 1974; 14(1):37-45.

Haynesworth et al., "Cell Surface Antigens on Human Marrow-Derived Mesenchymal Cells are Detected by Monoclonal Antibodies," Bone, 1992; 13:69-80.

Herrera, M.B. et al., "Mesenchymal Stem Cells Contribute to the Renal Repair of Acute Tubular Epithelial Injury," *Int. J. Mol. Med.*, 2004; 14(6):1035-1041.

Hill, D.P. et al., "Screening for Novel Pattern Formation Genes Using Gene Trap Approaches," *Methods in Enzymology*, 1993; 225:664-681.

Hill, M. et al., "Treatment for Swallowing Difficulties (Dysphagia) in Chronic Muscle Disease," *The Cochrane Library Cochrane Database Syst Rev.*, 2004; 2:1-12.

Hishikawa, K. et al., "Musculin/MyoR is Expressed in Kidney Side Population Cells and Can Regulate Their Function," *Journal of Cell Biology*, 2005; 169(6):921-928.

Holz, F.G. et al., "Intraocular Microablation of Choroidal Tissue by a 308 nm AIDA Excimer Laser for RPE-Transplantation in Patients With Age-Related Macular Degeneration," *Biomed. Technik*, (Berlin), 2003; 48:82-85.

Hongpaisan, J., "Inhibition of Proliferation of Contaminating Fibroblasts by D-Valine in Cultures of Smooth Muscle Cells From Human Myometrium," Cell Biol. Int., 2000; 24(1):1-7.

Hoynowski, S.M. et al., "Characterization and Differentiation of Equine Umbilical Cord-Derived Matrix Cells," *Biochemical and Biophysical Research Communications*, 2007; 362:347-353.

(56) References Cited

OTHER PUBLICATIONS

Hu, A. et al., "Hepatic Differentiation From Embryonic Stem Cells In Vitro," *Chin. Med. J.*, 2003; 116(12):1893-1897.

Hughes, G.C. et al., "Therapeutic Angiogenesis in Chronically Ischemic Porcine Myocardium: Comparative Effects of BFGF and VEGF," *Ann. Thorac. Surg.*, 2004; 77:812-818.

Hutmacher, D.W., "Scaffold Design and Fabrication Technologies for Engineering Tissues—State of the Art and Future Perspectives," *J. Biomater. Sci. Polymer Edn.*, 2001;12(1):107-24.

Ikeda, Y. et al, "Development of angiogenic cell and gene therapy by transplantation of umbilical cord blood with vascular endothelial growth factor gene," Hypertens Res, 2004; 27:119-28.

In't Anker, P., et al., "Isolation of Mesenchymal Stem Cells of Fetal or Maternal Origin from Human Placenta," *Stem Cells*, 2004; 22:1338-1345.

Isacson, O., "The Production and Use of Cells as Therapeutic Agents in Neurodegenerative Diseases," *The Lancet (Neurology)*, 2003; 2:417-424.

Isacson, O., et al., "Specific Axon Guidance Factors Persist in the Adult Brain as Demonstrated by Pig Neuroblasts Transplanted to the Rat," *Neurosci.*, 1996; 75(3):827-837.

Ishii, M. et al., "Molecular Markers Distinguish Bone Marrow Mesenchymal Stem Cells From Fibroblasts," *Biochemical and Biophysical Research Communications*, 2005; 332:297-303.

Ito, Y. et al., "A Quantitative Assay Using Basement Membrane Extracts to Study Tumor Angiogenesis In Vivo," *Int. J. Cancer*, 1996; 67:148-152.

Iwasaki, T., "Recent Advances in the Treatment of Graft-Versus-Host Disease," *Clin. Med. Res.*, 2004; 2(4):243-252.

Jackson, K.A. et al., "Regeneration of Ischemic Cardiac Muscle and Vascular Endothelium by Adult Stem Cells," *J. Clin. Invest.*, 2001; 107:1395-1402.

Jaffe, E.A. et al., "Culture of Human Endothelial Cells Derived From Umbilical Veins; Identification by Morphologic and Immunologic Criteria" *J Clin Invest*, 1973; 52:2745-2756.

Jaiswal et al., Adult Human Mesenchymal Stem Cell Differentiation to the Osteogenic or Adipogenic Lineage is Regulated by Motogen-Activated Protein Kinase, J. Biol. Chem., 2000; 275(13):9645-9652.

Janderová, L. et al., "Human Mesenchymal Stem Cells as an In Vitro Model for Human Adipogenesis," Obes. Res., 2003; 11(1):65-74.

Jang, Y.K. et al., "Retinoic Acid-Mediated Induction of Neurons and Glial Cells From Human Umbilical Cord-Derived Hematopoietic Stem Cells," *J. Neurosci. Res.*, 2004; 75(4):573-584.

Jeras, M., "The Role of In Vitro Alloreactive T-Cell Functional Tests in the Selection of HLA Matched and Mismatched Haematopoietic Stem Cell Donors," *Transpl. Immunol.*, 2002; 10:205-214.

Jikuhara, T. et al., "Left Atrial Function as a Reliable Predictor of Exercise Capacity in Patients With Recent Myocardial Infarction," *Chest*, 1997; 111(4):922-928.

Jo, Y.W. et al., "Use of Pharmasep Unit for Processing Microspheres," *AAPS PharmSciTech*, 2001; 2(1):Technical Note 2.

Johe, K.K. et al., "Single Factors Direct the Differentiation of Stem Cells From the Fetal and Adult Central Nervous System," *Genes & Devel.*, 1996; 10:3129-3140.

Johnstone, B. et al., "In Vitro Chondrogenesis of Bone-Marrow-Derived Mesenchymal Progenitor Cells," *Exp. Cell Res.*, 1998; 238:265-272.

Jomura, S. et al., "Potential Treatment of Cerebral Global Ischemia with Oct-4+ Umbilical Cord Matrix Cells," Stem Cells, Sep. 7, 2006, AlphaMed Press, Downloaded from www.StemCells.com at Ethicon, Inc. on Sep. 11, 2006 and Supplemental Data: 2.

Jones, J. et al., "Insulin-Like Growth Factors and their Binding Proteins: Biological Actions," Endocrine Review, 1995; 16(1):3-34.

Jones-Villeneuve, E.M. et al., "Retinoic Acid-Induced Neural Differentiation of Embryonal Carcinoma Cells," *Mol. & Cellu. Biol.*, 1983; 3(12):2271-2279.

Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, (2002); 277(9): 7574-7580.

Joussen, A.M. "Cell Transplantation in Age Related Macular Degeneration: Current Concepts and Future Hopes," *Graefe's Arch. Clin. Exp. Ophthalmol.*, 2004; 242:1-2.

Kadiyala, S. et al., "Culture Expanded Canine Mesenchymal Stem Cells Possess Osteochondrogenic Potential In Vivo and In Vitro," *Cell Transplant.*, 1997; 6(2):125-134.

Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," J. Exp. Med., Sep. 1984; 160:633-651.

Kicic, A. et al., "Differentiation of Marrow Stromal Cells Into Photoreceptors in the Rat Eye," *J. of Neurosci.*, 2003; 23(21):7742-7749.

Kim, J. et al., "Dopamine Neurons Derived From Embryonic Stem Cells Function in an Animal Model of Parkinson's Disease," *Nature*, 2002; 418:50-56.

Kim, J.Y. et al., "Ocular Surface Reconstruction: Limbal Stem Cell Transplantation," *Ophthal. Clin. N. Am.*, 2003; 16:67-77.

Kim, S.K. et al., "Intercellular Signals Regulating Pancreas Development and Function," Genes Dev., 2001; 15:111-127.

Kirschstein, R. et al., "Can Stem Cells Repair a Damaged Heart?" *Stem Cells: Scientific Progress and Future Research Directions*, 2001; 87-92.

Kisiday, J. et al., "Self-Assembling Peptide Hydrogel Fosters Chondrocyte Extracellular Matrix Production and Cell Division: Implications for Cartilage Tissue Repair," *PNAS*, 2002; 99(15):9996-10001.

Kitamura, S. et al., "Establishment and Characterization of Renal Progenitor Like Cells from S3 Segment of Nephron in Rat Adult Kidney," *The FASEB Journal: Official Publication of The Federation of American Societies for Experimental Biology*, 2005; 19(13).

Klahr, S et al., "Obstructive Nephropathy and Renal Fibrosis," *Am. J. Physiol. Renal. Physiol.*, 2002; 283(5):F861-875.

Klassen, H. et al., "Stem Cells and Retinal Repair," *Prog. Retin. Eye Res.*, 2004; 23(2):149-181.

Klein, J., Immunology: The Science of Self-Nonself Discrimination, John Wiley & Sons, New York, 1982; 453-58.

Kokufuta, E. et al., "Effects of Surfactants on the Phase Transition of Poly(N-isopropylacrylamide) Gel," *Macromolecules*, 1993; 26:1053-1059.

Kopeček, J., "Smart and Genetically Engineered Biomaterials and Drug Delivery Systems," *European Journal of Pharmaceutical Sciences*, 2003; 20:1-16.

Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76;1643-1648.

Kusama et al., "Growth and morphogenesis of mouse prostate epithelial cells in collagen gel matrix culture" *Cell Biol Int Rep*, 1989; 13:569-575.

Kushida, A., et al., "Decrease in Culture Temperature Releases Monolayer Endothelial Cell Sheets Together with Deposited Fibronectin Matrix from Temperature-Responsive Culture Surfaces," *J. of Biomedical Materials Research*, 1999; 45(4):355-362.

Laface, D. et al., "Gene Transfer Into Hematopoietic Progenitor Cells Mediated by an Adeno-Associated Virus Vector," *Virology*, 1988; 162:483-486.

Lang, K.J.D. et al., "Differentiation of Embryonic Stem Cells to a Neural Fate: A Route to Re-Building the Nervous System?" *J. of Neurosci. Res.*, 2004; 76:184-92.

Langeggen, H. et al.,"HUVEC Take Up Opsonized Zymosan Particles and Secrete Cytokines IL-6 and IL-8 In Vitro," *FEMS Immunol. Med. Microbiol.*, 2003; 36:55-61.

Le Belle, J.E. et al., "Stem Cells for Neurodegenerative Disorders: Where Can We Go From Here?," *Biodrugs*, 2002; 16(6):389-401.

Le Blanc, K. et al., "Treatment of Severe Acute Graft-Versus-Host Disease With Third Party Haploidentical Mesenchymal Stem Cells," *Lancet*, 2004; 363(9419):1439-1441.

Le Bouteiller, P. et al., "Soluble HLA-G1 at the Materno-Foetal Interface—A Review," Placenta, 2003; 24(Suppl. A):S10-S15.

Li, A. et al., "IL-8 Directly Enhanced Endothelial Cell Survival, Proliferation, and Matrix Metalloproteinases Production and Regulated Angiogenesis," *J. Immunol.*, 2003; 170:3369-3376.

(56) References Cited

OTHER PUBLICATIONS

Li, C.D. et al, "Mesenchymal Stem Cells Derived From Human Placenta Suppress Allogeneic Umbilical Cord Blood Lymphocyte Proliferation," *Cell Research*, 2005; 15(7):539-547.

Li, L.X. et al., "Inherited Retinal Dystrophy in the RCS Rat: Prevention of Photoreceptor Degeneration by Pigment Epithelial Cell Transplantation," *Exp. Eye Res.*, 1988; 47:911-917.

Li, Y. et al., "Intact, Injured, Necrotic and Apoptotic Cells after Focal Cerebral Ischemia in the Rat," *J. Neurol. Sci.*, 1998; 156:119-132.

Li, Y. et al., "Intracerebral Transplantation of Bone Marrow Stromal Cells in a 1-Methyl-4-Phenyl-1,2,3,6-Tetrahydropyridine Mouse Model of Parkinson's Disease," *Neuroscience Letts.*, 2001; 315:67-70.

Li, Y. et al., "Transplanted Olfactory Ensheathing Cells Promote Regeneration of Cut Adult at Optic Nerve Axons," *J. of Neuro.*, 2003; 23(21):7783-7788.

Li, Y. et al., "Ultrastructural and Light Microscopic Evidence of Apoptosis after Middle Cerebral Artery Occlusion in the Rat," *Am. J. Pathol.*, 1995; 146(5):1045-1051.

Liddiard, et al., "An Improved Method for the Preparation of Human Fetal and Adult Hepatocytes," *Arch. Toxicol.*, 1980; 44(1-3):107-12.

Lindenlaub, T. et al., "Partial Sciatic Nerve Transection as a Model of Neuropathic Pain: A Qualitative and Quantitative Study," *Pain*, 2000; 89(1): 97-106.

Lindvall, O. et al., "Stem Cell Therapy for Human Neurodegenerative Disorders—How to Make It Work," *Nature Medicine*, 2004;10(Suppl.):S42-S50.

Liu, K. et al, "Constitutive and Regulated Expression of Telomerase Reverse Transcriptase (hTERT) in Human Lymphocytes," *Proc. Natl. Acad. Sci.*, 1999; 96:5147-5152.

Liu, Y. et al., "Molecular and Genetic Mechanisms of Obesity: Implications for Future Management," *Curr. Mol. Med.*, 2003; 3(4):325-340.

Lockhart, D.J. et al., "Expression Monitoring by Hybridization to High-Density Oligonucleotide Arrays," *Nat. Biotechnol.*, 1996;14:1675-1680.

Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-751.

Lund, R.D. et al., "Cell Transplantation as a Treatment for Retinal Disease," *Progress in Retinal and Eye Research*, 2001; 20(4):415-449.

Lund, R.D. et al., "Retinal Transplantation: Progress and Problems in Clinical Application," *J. Leukocyte Biol.*, 2003; 74:151-160.

Lund, R.D. et al., "Subretinal Transplantation of Genetically Modified Human Cell Lines Attenuates Loss of Visual Function in Dystrophic Rats," *PNAS*, 2001; 98(17):9942-9997.

Luo, D. et al., "Synthetic DNA Delivery Systems," *Nat. Biotechnol.*, 2000; 18:33-36.

Luyten, F.P. et al., "Skeletal Tissue Engineering: Opportunities and Challenges," *Best Pract. Res. Clin. Rheumatol.*, 2001; 15(5):759-769.

Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.

Ma, P.X . et al., "Synthetic Nano-Scale Fibrous Extracellular Matrix ," *J. Biomed Mater Res.*, 1999; 46(1):60-72.

MacDonald, R.J. "Expression of the Pancreatic Elastase I Gene in Transgenic Mice," *Hepatology*, 1987; 7(1):42S-51S.

Mackay, A.M. et al., "Chondrogenic Differentiation of Cultured Human Mesenchymal Stem Cells From Marrow," *Tissue Engineering*, 1998; 4(4):415-428.

Maeshima, A. et al., "Adult Kidney Tubular Cell Population Showing Phenotypic Plasticity, Tubulogenic Capacity, and Integration Capability into Developing Kidney," *Journal of American Society of Nephrology*, 2006; 17(1):188-198.

Makino et al., "Cardiomyocytes can be generated from marrow stromal cells in vitro," *J. Clin. Invest.*, 1999; 103:697-70.

Marx, W.F. et al., "Endovascular Treatment of Experimental Aneurysms by Use of Biologically Modified Embolic Devices: Coil-Mediated Intraaneurysamal Delivery of Fibroblast Tissue Allografts," *Am. J. Neuroradiol.*, 2001; 22:323-333.

Mason, A.J. et al., "The Hypogonadal Mouse: Reproductive Functions Restored by Gene Therapy," Science, 1986; 234:1372-1378.

Mayer-Proschel, M. et al., "Isolation of Lineage-Restricted Neuronal Precursors From Multipotent Neuroepithelial Stem Cells," *Neuron.*, 1997; 19:773-785.

Medicetty, S. et al., "Transplantation of Human Umbilical Cord Matrix Stem Cells Alleviates Apomorphine-Induced Rotations in Parkinsonian Rats", 2003, XP-002383776, 1 page.

Melero-Martin, J. et al., "Optimal In-Vitro Expansion of Chondroprogenitor Cells in Monolayer Culture," *Biotechnology and Bioengineering*, 2006; 93(3):519-533.

Merriam-Webster Medline Plus Online Medical Dictionary, definitions of "iliac", "ilium" ileal/ileac and "ileum"; accessible online at http://www.nlm.nih.gov/medlineplus/mplusdictionary.html, last accessed Feb. 12, 2008.

Merriam-Webster Online Dictionary $10^{th}$ Edition, Definition of "Scaffold" [retrieved on Sep. 12, 2008].

Merx, M.W. et al., "Transplantation of Human Umbilical Vein Endothelial Cells Improves Left Ventricular Function in a Rat Model of Myocardial Infarction," *Basic Res. Cardiol.*, 2005; 100:208-216.

Messina, D.J., et al., "Comparison of Pure and Mixed Populations of Human Fetal-Derived Neural Progenitors Transplanted Into Intact Adult Rat Brain," *Exper. Neurol.*, 2003; 184:816-829.

Mitchell, K.E. et al., "Matrix Cells From Wharton's Jelly Form Neurons and Glia," *Stem Cells*, 2003; 21:50-60.

Moll, S. et al., "Monitoring Warfarin Therapy in Patients With Lupus Anticoagulants," *Ann. Intern. Med.*, 1997; 127(3):177-185.

Mombaerts, P. et al., "Creation of a Large Genomic Deletion at the T-Cell Antigen Receptor β-Subunit Locus in Mouse Embryonic Stem Cells by Gene Targeting," *Proc. Nat. Acad. Sci. USA*, 1991; 88:3084-3087.

Moore, A.E. et al., "Parkinsonian Motor Deficits are Reflected by Proportional A9/A10 Dopamine Neuron Degeneration in the Rat," *Exp. Neurol.*, 2001; 172(2):363-76.

Morgenstern, J.P. et al., "Advanced Mammalian Gene Transfer: High Titre Retroviral Vectors With Multiple Drug Selection Markers and a Complementary Helper-Free Packaging Cell Line," *Nucleic Acids Res.*, 1990; 18(12):3587-3596.

Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.

Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," *Blood*, 2002; 99(11):4200-4206.

Moulder, J.E., "Pharmacological Intervention to Prevent or Ameliorate Chronic Radiation Injuries," *Semin. Radiat. Oncol.*, 2003; 13(1):73-84.

Murohara, T., "Therapeutic vasculogenesis using human cord blood-derived endothelial progenitors," Trends Cardiovasc Med, 2001; 11: 303-307.

Nakamura, T. et al., "Ocular Surface Reconstruction Using Cultivated Mucosal Epithelial Stem Cells," *Cornea*, 2003; 22(Supp. 1):S75-S80.

Naughton et al., "Cells isolated from Wharton's jelly of the human umbilical cord develop a cartilage phenotype when treated with TGF-b in vitro" 1997; FASEB J 11:A19 (Abstract 108).

Newman, K.D. et al.,"Poly(D,L lactic-co-glycolic acid) Microspheres as Biodegradable Microcarriers for Pluripotent Stem Cells," *Biomaterials*, 2004; 25:5763-5771.

Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.*, 1990; 26:119-128.

Ninichuk, V. et al.,"Multipotent Mesenchymal Stem Cells Reduce Interstitial Fibrosis but Do Not Delay Progression of Chronic Kidney Disease in Collagen4A3-Deficient Mice," *Kidney Int.*, 2006; 70:121-129.

(56) References Cited

OTHER PUBLICATIONS

Nishida, K. et al., "Functional Bioengineered Corneal Epithelial Sheet Grafts From Corneal Stem Cells Expanded Ex Vivo on a Temperature-Responsive Cell Culture Surface," *Transplantation*, 2004; 77(3):379-385.

Nishishita, T. et al., "A Potential Pro-Angiogenic Cell Therapy With Human Placenta-Derived Mesenchymal Cells," *Biochemical and Biophysical Research Communications*, 2004; 325:24-31.

Nixon, P.J. et al., "The Contribution of Cone Responses to Rat Electroretinograms," *Clin. Experiment Ophthalmol.*, 2001; 29:193-196.

Nork, T.M. et al., "Swelling and Loss of Photoreceptors in Chronic Human and Experimental Glaucomas," *Arch. Ophthalmol.*, 2000; 118:235-245.

Nowak, A.P. et al., "Rapidly Recovering Hydrogel Scaffolds From Self-Assembling Diblock Copolypeptide Amphilphiles," *Nature*, 2002; 417:424-428.

Nusinowitz, S. et al., "Rod Multifocal Electroretinograms in Mice," *Invest Ophthalmol Vis. Sci.*, 1999; 40(12): 2848-2858.

Oh, S.H. et al., "Hepatocyte Growth Factor Induces Differentiation of Adult Rat Bone Marrow Cells Into a Hepatocyte Lineage In Vitro," *Biochem. & Biophys. Res. Comm.*, 2000; 279:500-504.

Ohnishi, S. et al., "Mesenchymal stem cells attenuate cardiac fibroblast proliferation and collagen synthesis through paracrine actions" FEBS Letters, 2007;581:3961-6.

Okumoto, K. et al., "Differentiation of Bone Marrow Cells Into Cells That Express Liver-Specific Genes In Vitro: Implication of the Notch Signals in Differentiation," *Biochem. & Biophys. Res. Commun.*, 2003; 304:691-695.

Oliver, J.A. et al., "The Renal Papilla is a Niche for Adult Kidney Stem Cells," *J. Clin Invest.*, 2004, 114(6):795-804.

Orlic, D. et al., "Stem Cells for Myocardial Regeneration," *Circ. Res.*, 2002; 91:1092-1102.

Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.*, 1985; 50:399-409.

Ortiz, L.A. et al., "Mesenchymal stem cell engraftment in lung is enhanced in response to bleomycin exposure and ameliorates its fibrotic effects," PNAS, 2003; 100:8407-8411.

Ortiz, L.A. et al., "Interleukin 1 receptor antagonist mediates the antiiflammatory and antifibrotic effect of mesenchymal stem cells during lung injury," PNAS, 2007;104:11002-7.

Osborne, N.N. et al., "Some Current Ideas on the Pathogenesis and the Role of Neuroprotection in Glaucomatous Optic Neuropathy," *Eur. J. Ophthalmol.*, 2003; 13(Supp. 3):S19-S26.

Palù, G. et al., "In Pursuit of New Developments for Gene Therapy of Human Diseases," *J. Biotechnol.*, 1999; 68:1-13.

Panepucci, R.A. et al., "Comparison of Gene Expression of Umbilical Cord Vein and Bone Marrow-Derived Mesenchymal Stem Cells," *Stem Cells*, 2004; 22(7):1263-78.

Patel, K.M. et al., "Mesenchymal Stem Cells Attenuate Hypoxic Pulmonary Vasoconstriction by a Paracrine Mechanism," J Surg Res., 2007; 143:281-5.

Pera, M.F. et al., "Human Embryonic Stem Cells", *J. Cell Science*, 2000; 113:5-10.

Pesce, M. et al., "Myoendothelial Differentiation of Human Umbilical Cord Blood-Derived Stem Cells in Ischemic Limb Tissues," Circulation Research, 2003; 93:e51-e62.

Petersdorf, E.W., "HLA Matching in Allogeneic Stem Cell Transplantation," *Curr. Op. Hematol*, 2004; 11:386-391.

Phipps, J.A. et al., "Paired-Flash Identification of Rod and Cone Dysfunction in the Diabetic Rat," *Investigative Ophthalmology & Visual Science*, 2004; 45:4592-4600.

Pisharodi, M. et al., "An Animal Model for Neuron-Specific Spinal Cord Lesions by the Microinjection of N-Methylaspartate, Kainic Acid, and Quisqualic Acid," *Appl. Neurophysiology*, 1985; 48:226-233.

Pittenger, M.F. et al., "Mesenchymal Stem Cells and Their Potential as Cardiac Therapeutics," *Circ. Res.*, 2004; 95:9-20.

Pittenger, M.F. et al., "Multilineage Potential of Adult Human Mesenchymal Stem Cells," *Science*, 1999; 284:143-47 and seven pages of online supplementary material.

Plaia, T., et al., "Characterization of a New NIH-Registered Variant Human Embryonic Stem Cell Line, BG01V: A Tool for Human Embryonic Stem Cell Research," *Stem Cells*, 2006: 24(3): 531-546.

Pountos, I. et al., "Mesenchymal Stem Cell Tissue Engineering: Techniques for Isolation, Expansion and Application," *Injury*, 2007; 38(Supp. 4):S23-33.

Quaini, F. et al., "Chimerism of the Transplanted Heart," *NEJM*, 2002; 346:5-15.

Rabbany, S.Y. et al., "Molecular Pathways Regulating Mobilization of Marrow-Derived Stem Cells for Tissue Revascularization," *TRENDS in Molecular Med.*, 2003; 9(3):109-117.

Rafii, S. et al., "Therapeutic Stem and Progenitor Cell Transplantation for Organ Vascularization and Regeneration," *Nature Med.*, 2003; 9(6):702-712.

Rahman, Z. et al., "Isolation and Primary Culture Urothelial Cells from Normal Human Bladder," *Urol. Research*, 1987; 15:315-320.

Ramon-Cueto, A. et al., "Functional Recovery of Paraplegic Rats and Motor Axon Regeneration in Their Spinal Cords by Olfactory Ensheathing Glia," *Neuron*, 2000; 25:425-435.

Ratner, B.D., et al., "Biomaterials: Where We Have Been and Where we are Going," Annu. Rev. Biomed. Eng., 2004; 6:41-75.

Readhead, C. et al., "Expression of a Myelin Basic Protein Gene in Transgenic Shiverer Mice: Correction of the Dysmyelinating Phenotype," *Cell*, 1987; 48:703-712.

Refaie, A. et al., "Experimental Islet Cell Transplantation in Rats: Optimization of the Transplantation Site," *Trans. Proc.*, 1998; 30:400-403.

Rehman, J. et al., "Secretion of Angiogenic and Antiapoptotic Factors by Human Adipose Stromal Cells," *Circulation*, 2004; 109:1292-1298.

Reubinoff, B.E. et al., "Neural Progenitors From Human Embryonic Stem Cells," *Nature Biotechnology*, 2001; 19:1134-1140.

Reyes, M. et al., "Purification and Ex Vivo Expansion of Postnatal Human Marrow Mesodermal Progenitor Cells," *Blood*, 2001; 98(9):2615-2625.

Rezai, K.A. et al., "Iris Pigment Epithelium Transplantation," *Graefe's Arch. Clin. Ophthalmol.*, 1997; 235:558-562.

Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.

Rios, M. et al., "Catecholamine Synthesis is Mediated by Tyrosinase in the Absence of Tyrosine Hydroxylase," *J. Neurosci.*, 1999, 19(9):3519-3526.

Rojas, M. et al. "Bone Marrow-Derived Mesenchymal Stem Cells in Repair of the Injured Lung," Am J Respir Cell Mol Biol., 2005; 33:145-152.

Romanov, Y.A. et al., "Searching for Alternative Sources of Postnatal Human Mesenchymal Stem Cells: Candidate MSC-Like Cells from Umbilical Cord," *Stem Cells*, 2003; 21:105-110.

Rosen, E.M. et al., "HGF/SF in Angiogenesis," *Ciba Found. Symp.*, 1997; 212:215-229.

Roskams, A.J. et al., "Directing Stem Cells and Progenitor Cells on the Stage of Spinal Cord Injury," *Exp. Neurol.*, 2005; 193:267-272.

Russo, E., Cultivating Policy from Cell Types, *The Scientist*, 2001; 15(11):6 (printout is numbered 1-6).

Rutherford, A. et al., "Eyeing-Up Stem Cell Transplantation," *Trends in Molecular Medicine*, 2001; 7(1):11.

Ryadnov, M.G. et al., "Engineering the Morphology of a Self-Assembling Protein Fibre," *Nat. Mater*, 2003; 2:329-332.

Sagrinati, C. et al., "Isolation and Characterization of Multipotent Progenitor Cells from the Bowman's Capsule of Adult Human Kidney," *Journal of American Society of Nephrology*, 2006; 17(9)2443-56.

Sahn, D.J. et al., "Recommendations Regarding Quantitation in M-Mode Echocardiography: Results of a Survey of Echocardiographic Measurements," *Circulation*, 1978; 58(6):1072-83.

Sakariassen, K.S. et al., "Methods and Models to Evaluate Shear-Dependent and Surface Reactivity-Dependent Antithrombotic Efficacy," *Thromb. Res.*, 2001; 104:149-174.

(56) References Cited

OTHER PUBLICATIONS

Salcedo, R. et al., "Human Endothelial Cells Express CCR2 and Respond to MCP-1: Direct Role of MCP-1 in Angiogenesis and Tumor Progression," *Blood*, 2000; 96(1):34-40.
Salgado, A.J. et al., "Bone Tissue Engineering: State of the Art and Future Trends," *Macromol. Biosci.*, 2004; 4:743-765.
Sauvé, Y. et al., "The Relationship Between Full Field Electroretinogram and Perimetry-Like Visual Thresholds in RCS Rats During Photoreceptor Degeneration and Rescue by Cell Transplants," *Vision Res.*, 2004; 44(1):9-18.
Schallert, T. et al., "Use-Dependent Structural Events in Recovery of Function," *Brain Plasticity, Adv. Neurol.*, 1997; 73:229-238.
Schouten, J.W. et al., "A Review and Rationale for the Use of Cellular Transplantation as a Therapeutic Strategy for Traumatic Brain Injury," *Journal of Neurotrauma*, 2004; 21(11):1501-1538.
Schraermeyer, U. et al., "Subretinally Transplanted Embryonic Stem Cells Rescue Photoreceptor Cells From Degeneration in the RCS Rats," *Cell Transplantation*, 2001; 10:673-680.
Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," *Tissue Antigens*, 1999; 54(4):409-37.
Schwartz, R.E. et al., "Multipotent Adult Progenitor Cells From Bone Marrow Differentiate Into Functional Hepatocyte-Like Cells," *J. of Clin. Invest.*, 2002; 109:1291-1302.
Sébire, G. et al., "In Vitro Production of IL-6, IL-β, and Tumor Necrosis Factor-α by Human Embryonic Microglial and Neural Cells," J. Immunol., 1993; 150(4):1517-1523.
Sethe, S. et al., "Aging of Mesenchymal Stem Cells," *Ageing Research Reviews*, 2006; 5:91-116.
Shani, M., "Tissue-Specific Expression of Rat Myosin Light-Chain 2 Gene in Transgenic Mice," *Nature*, 1985; 314:283-286.
Shimizu, T. et al., "Fabrication of Pulsatile Cardiac Tissue Grafts Using a Novel 3-Dimensional Cell Sheet Manipulation Technique and Temperature-Responsive Cell Culture Surfaces," *Circulation Research*, 2002; 90:e40-e48.
Shimizu, T. et al., "Cell Sheet Engineering for Myocardial Tissue Reconstruction," *Biomaterials*, 2003; 24:2309-2316.
Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-1126.
Siminoff, R. et al., "Properties of Reptilian Cutaneous Mechanoreceptors," *Exp. Neurol.*, 1968; 20:403-414.
Sommer, et al., "Ocular Tissue Engineering," *Ad. Exptl. Med. Biol.*, 2007, 585, pp. 413-429.
Song, H. et al., "Astroglia Induce Neurogenesis From Adult Neural Stem Cells," *Nature*, 2002; 417(6884):39-44.
Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12(5):354-365.
Storch, T.G. "Oxygen Concentration Regulates 5-Azacytidine-Induced Myogenesis in $C_3H/10T1/2$ Cultures," *Biochim. Biophys. Acta*, 1990; 1055:126-129.
Street, C.N. et al., "Stem Cells: A Promising Source of Pancreatic Islets for Transplantation in Type 1 Diabetes," Curr. Top Dev. Biol., 2003; 58:111-136.
Svendsen, C.N. "The Amazing Astrocyte," *Nature*, 2002; 417:29-32.
Svendsen, C.N. et al., "Long-Term Survival of Human Central Nervous System Progenitor Cells Transplanted Into a Rat Model of Parkinson's Disease," *Experim. Neurol.*, 1997; 148:135-146.
Swanson, R.A. et al., "A Semiautomated Method for Measuring Brain Infarct Volume," *J. Cereb. Blood Flow Metab.*, 1990; 10(2):290-293.
Swift, G.H. et al., "Tissue-Specific Expression of the Rat Pancreatic Elastase I Gene in Transgenic Mice," *Cell*, 1984; 38:639-646.
Tao, W., "Application of Encapsulated Cell Technology for Retinal Degenerative Disease", *Expert. Opin. Biol. Ther.*, 2006; 6(7): 717-726.

Taylor, D.A. et al., "Cardiac Chimerism as a Mechanism for Self-Repair: Does It Happen and If So to What Degree?" *Circulation*, 2002; 106:2-4.
Taylor, D.A. et al., "Regenerating Functional Myocardium: Improved Performance After Skeletal Myoblast Transplantation," *Nature Medicine*, 1998; 4(8):929-1200).
Thorsby, E. et al., "Role of HLA Molecules in the Induction of Alloimmune Responses: Clinical Significance in the Cyclosporine Era," *Transplant Proc.*, 2004; 36(Suppl 2S):16S-21S.
Timmermans, F. et al., "Stem Cells for the Heart, Are We There Yet?" *Cardiology*, 2003; 100:176-185.
Toma, C. et al., "Human Mesenchymal Stem Cells Differentiate to a Cardiomyocyte Phenotype in the Adult Murine Heart," Circulation 2002; 105:93-98.
Tomita, M. et al., "Bone Marrow-Derived Stem Cells Can Differentiate Into Retinal Cells in Injured Rat Retina," Stem Cells, 2002; 20:279-283.
Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001; 19:408-418.
Trenka-Benthin, S., 2005, Testicular Lesion Histology Report and Photomicrograph Indexes.
Tresco, P.A. et al., "Cellular Transplants as Sources for Therapeutic Agents," *Advanced Drug Delivery Reviews*, 2000; 42:3-27.
Tsonis, P.A. et al., "Lens and Retina Regeneration: Transdifferentiation, Stem Cells and Clinical Applications," *Experim. Eye Res.*, 2004; 78:161-172.
Turner, D., "The Human Leucocyte Antigen (HLA) System," *Vox Sang.*, 2004; 87(Suppl 1):S87-S90.
Tusher, V.G. et al., "Significance Analysis of Microarrays Applied to the Ionizing Radiation Response," *PNAS*, 2001; 98(9):5116-5121.
Ujike, H. et al., "Gene Expression Related to Synaptogenesis, Neuritogenesis, and MAP Kinase in Behavioral Sensitization to Psychostimulants," *Ann. N.Y. Acad. Sci.*, 2002; 965:55-67.
Ulloa-Montoya, F. et al., "Culture Systems for Pluripotent Stem Cells," *Journal of Bioscience and Bioengineering*, 2005; 100(1):12-27.
Urbich, C. et al., "Endothelial Progenitor Cells Characterization and Role in Vascular Biology,", *Circ. Res.*, 2004; 95:343-353.
Urbich, C. et al., "Endothelial Progenitor Cells Characterization and Role in Vascular Biology," *Circ. Res.*, 2004; 95:343-353.
Vajsar, J. et al., "Walker-Warburg Syndrome," *Orphanet Journal of Rare Diseases*, 2006; 1:29.
Van Hoffelen, S.J. et al., "Incorporation of Murine Brain Progenitor Cells Into the Developing Mammalian Retina," *Invest. Ophthalmol. Vis. Sci.*, 2003; 44(1):426-434.
Vassliopoulos, G. et al., "Transplanted Bone Marrow Regenerates Liver by Cell Fusion," *Nature*, 2003; 422:901-904.
Verma, I. M. et al., "Gene Therapy—Promises, Problems and Prospects," *Nature*, 1997; 389:239-242.
Vermot-Desroches, C. et al., "Heterogeneity of Antigen Expression Among Human Umbilical Cord Vascular Endothelial Cells: Identification of Cell Subsets by Co-Expression of Haemopoietic Antigens," *Immunol. Lett.*, 1995; 48:1-9.
Villegas-Perez, M.P. et al., "Influences of Peripheral Nerve Grafts on the Survival and Regrowth of Axotomized Retinal Ganglion Cells in Adult Rats," *J. Neurosci.*, 1988; 8(1):265-280.
Villegas-Perez, M.P. et al., "Rapid and Protracted Phases of Retinal Ganglion Cell Loss Follow Axotomy in the Optic Nerve of Adult Rats," *J. Neurobiology*, 1993; 24(1):23-36.
von Koskull, H. et al., "Induction of Cytokeratin Expression in Human Mesenchymal Cells," *J. Cell Physiol.*, 1987; 133:321-329.
Walboomers, X .F. et al., "Cell and Tissue Behavior on Micro-Grooved Surfaces," *Odontology*, 2001; 89:2-11.
Wang, D. et al., "Synthesis and Characterization of a Novel Degradable Phosphate-Containing Hydrogel," *Biomaterials*, 2003; 24:3969-3980.
Wang, X . et al., "Cell Fusion Is the Principal Source of Bone-Marrow-Derived Hepatocytes," *Nature*, 2003; 422:897-900.
Webster, T.J. et al.,"Nanoceramic Surface Roughness Enhances Osteoblast and Osteoclast Functions for Improved Orthopaedic/Dental Implant Efficacy," *Scripta Materialia*, 2001; 44(8/9):1639-1642.

(56) References Cited

OTHER PUBLICATIONS

Wegman, A. et al., "Nonsteroidal Anti-Inflammatory Drugs or Acetaminophen for Osteoarthritis of the Hip or Knee? A Synstematic Review of Evidence and Guidelines," J. Rheumatol., 2004; 31(2):344-354.
Weiss, M.L. et al., "Human Umbilical Cord Matrix Stem Cells: Preliminary Characterization and Effect of Transplantation in a Rodent Model of Parkinson's Disease," Stem Cells, 2006; 24:781-792.
Weiss, M.L. et al., "Transplantation of Porcine Umbilical Cord Matrix Cells Into the Rat Brain," Exp. Neur., 2003; 182:288-299.
Wenning, G.K. et al., "Neural Transplantation in Animal Models of Multiple System Atrophy: A Review," J. Nueral Transm., 1999; Suppl.(55):103-113.
Wikipedia, Definition of "Iliac crest" provided by Wikipedia, the free encyclopedia; retrieved from the Internet at URL: http://en.wikipedia.org/wiki/Iliac_crest; downloaded on Dec. 18, 2007.
Williams, J.T. et al., "Cells Isolated From Adult Human Skeletal Muscle Capable of Differentiating Into Multiple Mesodermal Phenotypes," Am. Surg. Jan. 1999:65(I):22-26.
Wobus, A.M. et al., "Retinoic Acid Accelerates Embryonic Stem Cell-Derived Cardiac Differentiation and Enhances Development of Ventricular Cardiomyocytes," J. Mol. Cell Cardiol., 1997; 29:1525-1539.
Wolford, L.M. et al., "Considerations in Nerve Repair," BUMC Proceedings, 2003; 16:152-156.
Woodbury, D., et al., "Adult Rat and Human Bone Marrow Stromal Cells Differentiate Into Neurons," J. Neurosci. Res., 2000; 61:364-370.
Wulf, G.G. et al., "Mesengenic Progenitor Cells Derived From Human Placenta," Tissue Engineering, 2004; 10(7/8):1136-1147.
Xu, A. et al.,"Soft, Porous Poly(D,L lactide-co-glycotide) Microcarriers Designed for Ex Vivo Studies and for Transplantation of Adherent Cell Types including Progenitors," Annals of the New York Academy of Sciences, 2001, vol. 944: 144-159.
Xu, C. et al., "Characterization and Enrichment of Cardiomyocytes Derived From Human Embryonic Stem Cells," Circ. Res., 2002; 91:501-508.
Xu, Y. et al., "Dopamine, in the Presence of Tyrosinase, Covalently Modifies and Inactivates Tyrosine Hydroxylase," J. Neurosci. Res., 1998; 54:691-697.
Yamada, M. et al., "Bone Marrow-Derived Progenitor Cells Are Important for Lung Repair after Lipopolysaccharide-Induced Lung Injury," J Immunol., 2004; 172:1266-72; erratum J Immunol. 2004;173:4755.
Yamashima, T., "Implication of Cysteine Proteases Calpain, Cathepsin and Caspase in Ischemic Neuronal Death of Primates," Progress in Neurobiology, 2000; 62:273-295.
Yang, H. et al., "Region-Specific Differentiation of Neural Tube-Derived Neuronal Restricted Progenitor Cells After Heterotopic Transplantation," PNAS, 2000; 97(24):13366-13371.
Ye Q. et al., "Recovery of Placental-Derived Adherent Cells With Mesenchymal Stem Cell Characteristics", Blood, 2001; 98(11 Part 2):147B (Abstract No. 4260).
Yip, H.K., et al., "Axonal Regeneration of Retinal Ganglion Cells: Effect of Trophic Factors," Prog. Retin Eye Res., 2000; 19(5):559-575.
Yokoo, T. et al., "Stem Cell Gene Therapy for Chronic Renal Failure," Curr Gene Ther., 2003; 3:387-394.
Yu, M. et al., "Mid-Trimester Fetal Blood-Derived Adherent Cells Share Characteristics Similar to Mesenchymal Stem Cells but Full-Term Umbilical Cord Blood Does Not," British J. of Haematology, 2004; 124:666-675.
Zangani, D. et al., "Multiple Differentiation Pathways of Rat Mammary Stromal Cells In Vitro: Acquisition of a Fibroblast, Adipocyte or Endothelial Phenotype is Dependent on Hormonal and Extracellular Matrix Stimulation," Differentiation, 1999; 64:91-101.
Zeng, B.Y. et al., "Regenerative and Other Responses to Injury in the Retinal Stump of the Optic Nerve in Adult Albino Rats: Transection of the Intracranial Optic Nerve," J. Anat., 1995; 186:495-508.
Zhang, L. et al., "A Test for Detecting Long-Term Sensorimotor Dysfunction in the Mouse after Focal Cerebral Ischemia," J. Neurosci. Methods, 2002; 117:207-214.
Zhang, S. et al., "In Vitro Differentiation of Transplantable Neural Precursors From Human Embryonic Stem Cells," Nature Biotechnology, 2001; 19:1129-1133.
Zhang, X. et al., "Efficient Adeno-Associated Virus-Mediated Gene Expression in Human Placenta-Derived Mesenchymal Cells," Microbiol. Immunol., 2003; 47(1):109-116.
Zhang, Y. et al., "Comparison of Mesenchymal Stem Cells from Human Placenta and Bone Marrow," Chinese Medical Journal, 2004; 117:882-887.
Zhang, Z.G. et al., "Correlation of VEGF and Angiopoietin Expression with Disruption of Blood-Brain Barrier and Angiogenesis after Focal Cerebral Ischemia," J. Cereb. Blood Flow Metab., 2002; 22(4):379-392.
Zimmerman, S. et al., "Lack of Telomerase Activity in Human Mesenchymal Stem Cells," Leukemia, 2003; 17:1146-1149.
Zuloff-Shani, A. et al., "Macrophage Suspensions Prepared From a Blood Unit for Treatment of Refractory Human Ulcers," Transfus. Apheresis Sci., 2004; 30:163-167.
In the U.S. Patent and Trademark Office, Non-Final Office Action in re: U.S. Appl. No. 12/642,775 dated Nov. 21, 2012, 16 pages.
In the U.S. Patent and Trademark Office, Non-Final Office Action in re: U.S. Appl. No. 13/111,933 dated Dec. 19, 2012, 17 pages.
In the U.S. Patent and Trademark Office, Non-Final Office Action in re: U.S. Appl. No. 13/605,716 dated Feb. 13, 2013, 13 pages.
Cai, J. et al "Stem cell and precursor cell therapy," NeuroMolecular Medicine, 2002; 3:233-249.
Linnes, M.P. et al., "A fibrinogen-based precision microporous scaffold for tissue engineering," Biomaterials, 2007; 28:5298-306.
Seaver et al. "The chick oviduct in tissue culture. I. Initial characterization of growing primary oviduct tissue cultures," Exp. Cell Res., 1984; 155: 241-251.
Seiji, T. et al., "Possibility of Regenerative Medicine Using Human Amniotic Cells," Regenerative Medicine, 2002; 1(2):79-85. (English Language Abstract).
Wang, Y. et al., "Enhanced Recovery of Hematopoietic Progenitor and Stem Cells from Cultivated, Postpartum Human Placenta," Blood, 2001; 98(11): 183a (Abstract 769 ).
In the U.S. Patent and Trademark Office, Final Office Action in re: U.S. Appl. No. 13/111,933 dated May 28, 2013 , 14 pages.
In the U.S. Patent and Trademark Office, Final Office Action in re: U.S. Appl. No. 11/317,574 dated Jul. 11, 2013, 29 pages.
Abbas, A.K. et al., "Chapter 8—Activation of T Lymphocytes," Cellular and Molecular Immunology (5th Ed., 2003), Saunders, Philadelphia, p. 171 (plus book cover pp. 1 and 2)(3 pages).
Fauza, D., "Chapter 28 Fetal Tissue Engineering," Principles of Tissue Engineering, Lanza et al. editors (2nd ed., May 2002), Academic Press, New York, p. 353-355.
In the U.S. Patent and Trademark Office Final Office Action in re: U.S. Appl. No. 12/389,305 dated Aug. 6, 2014, 57 pages.
In the U.S. Patent and Trademark Office, Non-Final Office Action in re: U.S. Appl. No. 11/611,602 dated Oct. 9, 2014, 15 pages.
In the U.S. Patent and Trademark Office, Final Office Action in re: U.S. Appl. No. 11/317,574 dated Feb. 3, 2014, 12 pages
In the U.S. Patent and Trademark Office, Final Office Action in re: U.S. Appl. No. 11/321,864 dated Nov. 3, 2014, 10 pages.
In the U.S. Patent and Trademark Office, Final Office Action in re: U.S. Appl. No. 10/876,998 dated Dec. 16, 2014, 19 pages.
In the U.S. Patent and Trademark Office, Non-Final Office Action in re: U.S. Appl. No. 11/322,372 dated Nov. 25, 2014, 24 pages.
In the U.S. Patent and Trademark Office, Final Office Action in re: U.S. Appl. No. 11/315,969 dated Dec. 18, 2014, 30 pages.
In the U.S. Patent and Trademark Office, Final Office Action in re: U.S. Appl. No. 11/321,863 dated Jan. 31, 2014, 17 pages.
Ciavarella, S. et al., "Umbilical Cord Mesenchymal Stem Cells: Role of Regulatory Genes in Their Differentiation to Osteoblasts," Stem Cells and Development, 2009; 18:1211-1220.
Hass, R. et al., "Different populations and sources of human mesenchymal stem cells (MSC): A comparison of adult and neonatal tissue-derived MSC," Cell Communication and Signaling, 2011; 9:12, p. 1-14.

(56) References Cited

OTHER PUBLICATIONS

Ho, A.D. et al., "Heterogeneity of mesenchymal stromal cell preparations," *Cytotherapy*, 2008; 10(4):320-30.

Mattsson, J. et al. "Graft Failure after Allogenic Hematopoietic Cell Transplantation," *Biol Blood Marrow Transplant*, 2008; 14 (Supplement 1): 165-170.

Rachakatla, R. S. et al., "Development of Human Umbilical Cord Matrix Stem Cell-Based Gene Therapy for Experimental Lung Tumors," *Cancer Gene Therapy*, 2007; 14:828-835.

Secco, M. et al., "Multipotent Stem Cells from Umbilical Cord: Cord is Richer than Blood!" *Stem Cells*, 2008; 26:146-150.

Solomon, D. E., "An in vitro examination of extracellular matrix scaffold for use in wound healing," *Int. J. Path*, 2002, 93: 209-216.

Troyer, D. L. et al., "Concise Review: Wharton's Jelly-Derived Cells Are a Primitive Stromal Cell Population," *Stem Cells*, 2008; 26:591-599.

In the U.S. Patent and Trademark Office, Non-Final Office Action in re: U.S. Appl. No. 14/152,649 dated Feb. 26, 2015, 9 pages.

In the U.S. Patent and Trademark Office, Final Office Action in re: U.S. Appl. No. 14/444,689 dated Mar. 24, 2015, 9 pages.

In the U.S. Patent and Trademark Office, Final Office Action in re: U.S. Appl. No. 11/317,574 dated Apr. 1, 2015, 12 pages.

In the U.S. Patent and Trademark Office, Final Office Action in re: U.S. Appl. No. 11/617,346 dated Apr. 15, 2015, 21 pages.

Chen K. et al., "Human umbilical cord mesenchymal stem cells hUC-MSCs exert immunosuppressive activities through a PGE2-dependent mechanism," *Clinical Immunology*, 2010, 135; 448-458.

Leventhal, C. et al. "Endothelial trophic support for neuronal production and recruitment from the adult mammalian subependyma," *Molecular and Cellular Neuroscience*, 1999; 13; 450-464.

Otsuka, A. et al. "Lipopolysaccharide augments HLA-A,B,C molecule expression but inhibits interferon-gamma-induced HLA-DR molecule expression on cultured human endothelial cells," *Immunology*, 1991; 73; 428-432.

Park, B-G et al., "Development of high density mammalian cell culture system for the production of tissue-type plasminogen activator," *Biotechnology and Bioprocess Engineering*, 2000; 5:123-129.

Pittenger, M.F. et al.; "Human mesenchymal stem cells: progenitor cells for cartilage, bone, fat and stroma," Current *Topics in Microbiology and Immunology*, 2000; 251:3-11.

Schuler, JJ et al., "Efficacy of prostaglandin E1 in the treatment of lower extremity ischemic ulcers secondary to peripheral vascular occlusive disease. Results of a prospective randomized, double-blind, multicenter clinical trial," J. *Vasc. Surg.*, 1984, 1(1):160-70.

\* cited by examiner

A.

B.

A.

B.

TREATMENT OF PERIPHERAL VASCULAR DISEASE USING UMBILICAL CORD TISSUE-DERIVED CELLS

CROSS-REFERENCE TO RELATED APPLICATIONS

This application is a continuation-in-part of U.S. patent application Ser. No. 11/617,346, filed Dec. 28, 2006, which claims benefit to U.S. Provisional Patent Application No. 60/754,366, filed Dec. 28, 2005, the contents of which are incorporated by reference herein, in their entirety.

FIELD OF THE INVENTION

The invention relates to the field of cell based or regenerative therapy for peripheral vascular disease patients, especially those with peripheral ischemia. In particular, the invention provides cells derived from umbilical cord tissue having the capability to stimulate and support angiogenesis, to improve blood flow, to regenerate, repair, and improve skeletal muscle damaged by a peripheral ischemic event, and to protect skeletal muscle from ischemic damage.

BACKGROUND OF THE INVENTION

Various publications, including patents, published applications, technical articles and scholarly articles are cited throughout the specification. Each of these cited publications is incorporated by reference herein, in its entirety.

Peripheral vascular disease (PVD) can result from atherosclerotic occlusion of the blood vessels, particularly in limbs and areas distal from the heart, resulting in diminished blood flow and insufficient oxygen perfusion to tissues in the vicinity of and downstream from the occlusion. PVD is frequently manifested in the iliac blood vessels, femoral and popliteal blood vessels, and subclavian blood vessels, and its effects can be exacerbated by thrombi, emboli, or trauma. It is estimated that approximately 8 to 12 million individuals in the United States, especially among the elderly population and those with diabetes, are afflicted with PVD.

Common symptoms of PVD include cramping in the upper and lower limbs and extremities, numbness, weakness, muscle fatigue, pain in the limbs and extremities, hypothermia in the limbs and extremities, discoloration of the extremities, dry or scaly skin, and hypertension. The most common symptom is claudication or feelings of pain, tightness, and fatigue in muscles downstream of the occluded blood vessel that occurs during some form of exercise such as walking, but self-resolve after a period of rest.

In terms of pathophysiology, the occluded blood vessels cause ischemia of tissues at the site of and distal to the obstruction. This ischemia is generally referred to as peripheral ischemia, meaning that it occurs in locations distal to the heart. The severity of the ischemia is a function of the size and number of obstructions, whether the obstruction is near a muscle or organ, and whether there is sufficient redundant vasculature. In more severe cases, the ischemia results in death of the affected tissues, and can result in amputation of affected limbs, or even death of the patient.

Current methods for treatment of more severe cases of PVD include chemotherapeutic regimens, angioplasty, insertion of stents, reconstructive surgery, bypass grafts, resection of affected tissues, or amputation. Unfortunately, for many patients, such interventions show only limited success, and many patients experience a worsening of the conditions or symptoms.

Presently, there is interest in using either stem cells, which can divide and differentiate, or muscles cells from other sources, including smooth and skeletal muscles cells, to assist the in the repair or reversal of tissue damage. Transplantation of stem cells can be utilized as a clinical tool for reconstituting a target tissue, thereby restoring physiologic and anatomic functionality. The application of stem cell technology is wide-ranging, including tissue engineering, gene therapy delivery, and cell therapeutics, i.e., delivery of biotherapeutic agents to a target location via exogenously supplied living cells or cellular components that produce or contain those agents (For a review, see Tresco, P. A. et al., (2000) *Advanced Drug Delivery Reviews* 42:2-37). The identification of stem cells has stimulated research aimed at the selective generation of specific cell types for regenerative medicine.

One obstacle to realization of the therapeutic potential of stem cell technology has been the difficulty of obtaining sufficient numbers of stem cells. Embryonic, or fetal tissue, is one source of stem cells. Embryonic stem and progenitor cells have been isolated from a number of mammalian species, including humans, and several such cell types have been shown capable of self-renewal and expansion, as well differentiation into a number of different cell lineages. But the derivation of stem cells from embryonic or fetal sources has raised many ethical and moral issues that are desirable to avoid by identifying other sources of multipotent or pluripotent cells.

Postpartum tissues, such as the umbilical cord and placenta, have generated interest as an alternative source of stem cells. For example, methods for recovery of stem cells by perfusion of the placenta or collection from umbilical cord blood or tissue have been described. A limitation of stem cell procurement from these methods has been an inadequate volume of cord blood or quantity of cells obtained, as well as heterogeneity in, or lack of characterization of, the populations of cells obtained from those sources.

A reliable, well-characterized and plentiful supply of substantially homogeneous populations of such cells having the ability to differentiate into an array of skeletal muscle, pericyte, or vascular lineages would be an advantage in a variety of diagnostic and therapeutic applications for skeletal muscle repair, regeneration, and improvement, for the stimulation and/or support of angiogenesis, and for the improvement of blood flow subsequent to a peripheral ischemic event, particularly in PVD patients.

SUMMARY OF THE INVENTION

One aspect of the invention features method of treating a patient having peripheral vascular disease, the method comprising administering to the patient umbilical cord tissue-derived cells in an amount effective to treat the peripheral vascular disease, wherein the umbilical cord tissue-derived cells are derived from human umbilical cord tissue substantially free of blood, wherein the cells are capable of self-renewal and expansion in culture and have the potential to differentiate into cells of at least a skeletal muscle, vascular smooth muscle, pericyte, or vascular endothelium phenotype; wherein the cells require L-valine for growth and can grow in at least about 5% oxygen; wherein the cells further comprise at least one of the following characteristics: (a) potential for at least about 40 doublings in culture; (b) attachment and expansion on a coated or uncoated tissue culture vessel, wherein the coated tissue culture vessel comprises a coating of gelatin, laminin, collagen, polyornithine, vitronectin, or fibronectin; (c) production of at least one of tissue factor, vimentin, and alpha-smooth muscle actin; (d) production of at least one of CD10, CD13, CD44, CD73, CD90, PDGFr-alpha, PD-L2 and HLA-A,B,C; (e) lack of production of at least one of CD31, CD34, CD45, CD80, CD86, CD117, CD141, CD178, B7-H2, HLA-G, and HLA-DR,DP,DQ, as detected by flow cytometry; (f) expression of a gene, which relative to a human cell that is a fibroblast, a mesenchymal stem cell, or an iliac crest bone marrow cell, is increased for at least one of a gene encoding: interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; tumor necrosis factor, alpha-induced protein 3; (g) expression of a gene, which relative to a human cell that is a fibroblast, a mesenchymal stem cell, or an iliac crest bone marrow cell, is reduced for at least one of a gene encoding: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (Drosophila); crystallin, alpha B; dishevelled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (Drosophila); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (Drosophila); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; cytochrome c oxidase subunit VIIa polypeptide 1 (muscle); similar to neuralin 1; B cell translocation gene 1; hypothetical protein FLJ23191; and DKFZp586L151; (h) secretion of at least one of MCP-1, IL-6, IL-8, GCP-2, HGF, KGF, FGF, HB-EGF, BDNF, TPO, MIP1b, RANTES, and TIMP1; and (i) lack of secretion of at least one of TGF-beta2, ANG2, PDGFbb, MIP1a and VEGF, as detected by ELISA.

In a particular embodiment, the peripheral vascular disease is peripheral ischemia. In certain embodiments, the cells are induced in vitro to differentiate into a skeletal muscle, vascular smooth muscle, pericyte, or vascular endothelium lineage cells prior to administration. In other embodiments, the cells are genetically engineered to produce a gene product that promotes treatment of peripheral vascular disease.

In some embodiments of the method, cells are administered with at least one other cell type, which may include skeletal muscle cells, skeletal muscle progenitor cells, vascular smooth muscle cells, vascular smooth muscle progenitor cells, pericytes, vascular endothelial cells, vascular endothelium progenitor cells, or other multipotent or pluripotent stem cells. The other cell type can administered simultaneously with, or before, or after, the umbilical cord tissue-derived cells.

In other embodiments, the cells are administered with at least one other agent, which may be an antithrombogenic agent, an anti-inflammatory agent, an immunosuppressive agent, an immunomodulatory agent, pro-angiogenic, or an antiapoptotic agent, for example. The other agent can be administered simultaneously with, or before, or after, the umbilical cord tissue-derived cells.

The cells are preferably administered at or proximal to the sites of the peripheral ischemia, but can also be administered at sites distal to the peripheral ischemia. They can be administered by injection, infusion, a device implanted in the patient, or by implantation of a matrix or scaffold containing the cells. The cells may exert a trophic effect, such as proliferation, on the skeletal muscle, vascular smooth muscle or vascular endothelium of the patient. The cells may induce migration of skeletal muscle cells, vascular smooth muscle cells, vascular endothelial cells, skeletal muscle progenitor cells, pericytes, vascular smooth muscle progenitor cells, or vascular endothelium progenitor cells to the site or sites of peripheral vascular disease, such as peripheral ischemia.

Another aspect of the invention features pharmaceutical compositions and kits for treating a patient having a peripheral vascular disease, comprising a pharmaceutically acceptable carrier and the umbilical cord tissue-derived cells described above or preparations made from such umbilical cord tissue-derived cells. In some preferred embodiments, the preparations comprise FGF and HGF. The pharmaceutical compositions and kits are designed and/or formulated for practicing the methods of the invention as outlined above.

According to another aspect of the invention, the above-described methods may be practiced using a preparation made from the umbilical cord tissue-derived cells, wherein the preparation comprises a cell lysate of the umbilical cord tissue-derived cells, an extracellular matrix of the umbilical cord tissue-derived cells or a conditioned medium in which the umbilical cord tissue-derived cells were grown. It is preferred that such preparations comprise FGF and HGF.

Other aspects of the invention feature pharmaceutical compositions and kits containing preparations comprising cell lysates, extracellular matrices or conditioned media of the umbilical cord tissue-derived cells.

One embodiment of the invention is a method of treating a patient having a peripheral vascular disease, comprising administering a pharmaceutical composition comprising a fibrin glue and an isolated homogenous population of cells obtained from human umbilical cord tissue in an amount effective to treat the disease, wherein the umbilical cord tissue is substantially free of blood, and wherein isolated homogenous population of cells is capable of self-renewal and expansion in culture, has the potential to differentiate and does not express CD117 and/or telomerase. The isolated population of cells may also have one or more of the following characteristics:

(a) expresses oxidized low density lipoprotein receptor 1, reticulon, chemokine receptor ligand 3, and/or granulocyte chemotactic protein;

(b) does not express CD31, CD34 or CD45;

(c) expresses, relative to a human fibroblast, mesenchymal stem cell, or iliac crest bone marrow cell, increased levels of interleukin 8 or reticulon 1;

(d) has the potential to differentiate into cells of at least a skeletal muscle, vascular smooth muscle, pericyte or vascular endothelium phenotype; and (d) expresses CD10, CD13, CD44, CD73, and CD90.

In one embodiment, the peripheral vascular disease is peripheral ischemia. The pharmaceutical composition is administered at the sites of peripheral ischemia. In another embodiment, the pharmaceutical composition is administered locally. In one embodiment, the pharmaceutical composition is administered by injection, infusion, a device implanted in a patient, or by implantation of a matrix or scaffold containing the pharmaceutical composition. In an alternate embodiment, the pharmaceutical composition is administered by intramuscular injection and injection into adipose depots in muscle. In another embodiment, the pharmaceutical composition is administered by injection into interstitial spaces so as not to enter directly into circulation. The isolated population of cells may be induced in vitro to differentiate into a skeletal muscle, vascular muscle, pericyte or vascular endothelium lineage prior to administration. The population of cells may also be genetically engineered to produce a gene product that promotes treatment of peripheral vascular disease. Optionally, the composition further comprises an agent selected from the group consisting of an antithrombogenic agent, an immunosuppressive agent, an immunomodulatory agent, a pro-angiogenic, an antiapoptotic agent and mixtures thereof. Alternatively, the composition further comprises at least one other cell type (such as e.g. a skeletal muscle cell, a skeletal muscle progenitor cell, a vascular smooth muscle cell, a vascular smooth muscle progenitor cell, a pericyte, a vascular endothelial cell, a vascular endothelium progenitor cell or other multipotent or pluripotent stem cell). In one embodiment, the pharmaceutical composition exerts a trophic effect (such as e.g. proliferation of vascular endothelial cells). In another embodiment, the pharmaceutical composition induces migration of vascular endothelial cells and/or vascular endothelium progenitor cells to the sites of the peripheral disease. In yet an alternate embodiment, the pharmaceutical composition induces migration of vascular smooth muscle cells and/or vascular smooth muscle progenitor cells to the sites of the peripheral disease. In another embodiment, the pharmaceutical composition induces migration of pericytes to the sites of the peripheral vascular disease. In one embodiment, the fibrin glue comprises fibrinogen and thrombin. In another embodiment, the fibrin glue comprises from about 16 to about 24 IU/ml of thrombin and from about 39.3 to about 60.7 mg/ml of fibrinogen.

Another embodiment of the invention is a method of treating a patient having a peripheral vascular disease, comprising administering a fibrin glue (e.g. a composition comprising fibrinogen and thrombin) and an isolated homogenous population of cells obtained from human umbilical cord tissue in an amount effective to treat the disease, wherein the umbilical cord tissue is substantially free of blood, and wherein isolated homogenous population of the cells is capable of self-renewal and expansion in culture, has the potential to differentiate and does not express CD117 and/or telomerase. The isolated population of cells may have other characteristics, including one or more of the following:

(a) expresses oxidized low density lipoprotein receptor 1, reticulon, chemokine receptor ligand 3, and/or granulocyte chemotactic protein;

(b) does not express CD31, CD34 or CD45;

(c) express, relative to a human fibroblast, mesenchymal stem cell, or iliac crest bone marrow cell, increased levels of interleukin 8 or reticulon 1;

(d) has the potential to differentiate into cells of at least a skeletal muscle, vascular smooth muscle, pericyte or vascular endothelium phenotype; and (d) expresses CD10, CD13, CD44, CD73, and CD90.

In one embodiment, the peripheral vascular disease is peripheral ischemia and, optionally, the fibrin glue and the population of cells are administered at the sites of peripheral ischemia. Various routes of administration may be used including administered by injection, infusion, a device implanted in a patient, or by implantation of a matrix or scaffold containing the cells. In one embodiment, the population of cells and fibrin glue are administered locally (such as e.g. by intramuscular injection and injection into adipose depots in muscle). In another embodiment, the cells and fibrin glue are administered by injection into interstitial spaces so as not to directly enter into circulation. Optionally, the isolated population of cells is induced in vitro to differentiate into a skeletal muscle, vascular muscle, pericyte or vascular endothelium lineage prior to administration. The population of cells may also be genetically engineered to produce a gene product that promotes treatment of peripheral vascular disease. In one embodiment, the method further comprises administration of an agent selected from the group consisting of an antithrombogenic agent, an immunosuppressive agent, an immunomodulatory agent, a pro-angiogenic, an antiapoptotic agent and mixtures thereof. In another embodiment, the method further comprises administration of at least one other cell type (such as e.g. a skeletal muscle cell, a skeletal muscle progenitor cell, a vascular smooth muscle cell, a vascular smooth muscle progenitor cell, a pericyte, a vascular endothelial cell, a vascular endothelium progenitor cell or other multipotent or pluripotent stem cell). In one embodiment, the population of cells exerts a trophic effect (e.g. proliferation of vascular endothelial cells). The population of cells may induce migration of vascular endothelial cells and/or vascular endothelium progenitor cells to the sites of the peripheral disease. Alternatively, the population of cells may induce migration of vascular smooth muscle cells and/or vascular smooth muscle progenitor cells to the sites of the peripheral disease. The population of cells also may induce migration of pericytes to the sites of the peripheral vascular disease. The fibrin glue may comprise fibrinogen and thrombin. In one embodiment, the fibrin glue is administered simultaneously with, or before, or after, the isolated homogenous population of cells obtained from human umbilical cord tissue. In another embodiment, the fibrin glue comprises from about 16 to about 24 IU/ml of thrombin and from about 39.3 to about 60.7 mg/ml of fibrinogen.

Another embodiment of the invention is a kit for treating a patient having a peripheral vascular disease comprising fibrinogen, thrombin and an isolated homogenous population of cells obtained from human umbilical cord tissue in an amount effective to treat the disease, wherein the umbilical cord tissue is substantially free of blood, and wherein said isolated homogenous population of the cells is capable of self-renewal and expansion in culture, has the potential to differentiate and do not express CD117 and/or telomerase. The kit may further comprise instructions for use. In one embodiment, the fibrinogen and isolated homogenous population of cells are in provided in a composition to which thrombin may be added immediately prior to use. The isolated population of cells may have other characteristics, including one or more of the following:

(a) expresses oxidized low density lipoprotein receptor 1, reticulon, chemokine receptor ligand 3, and/or granulocyte chemotactic protein;
(b) does not express CD31, CD34 or CD45;
(c) express, relative to a human fibroblast, mesenchymal stem cell, or iliac crest bone marrow cell, increased levels of interleukin 8 or reticulon 1;
(d) has the potential to differentiate into cells of at least a skeletal muscle, vascular smooth muscle, pericyte or vascular endothelium phenotype; and
(d) expresses CD10, CD13, CD44, CD73, and CD90.

In one embodiment, the kit comprises from about 16 to about 24 IU/ml of thrombin and from about 39.3 to about 60.7 mg/ml of fibrinogen. In one embodiment, the kit comprises a fibrinogen component comprising fibrin and factor XII and a thrombin component comprising thrombin and calcium.

Other features and advantages of the invention will be understood by reference to the detailed description and examples that follow.

DETAILED DESCRIPTION

Figure 1A:
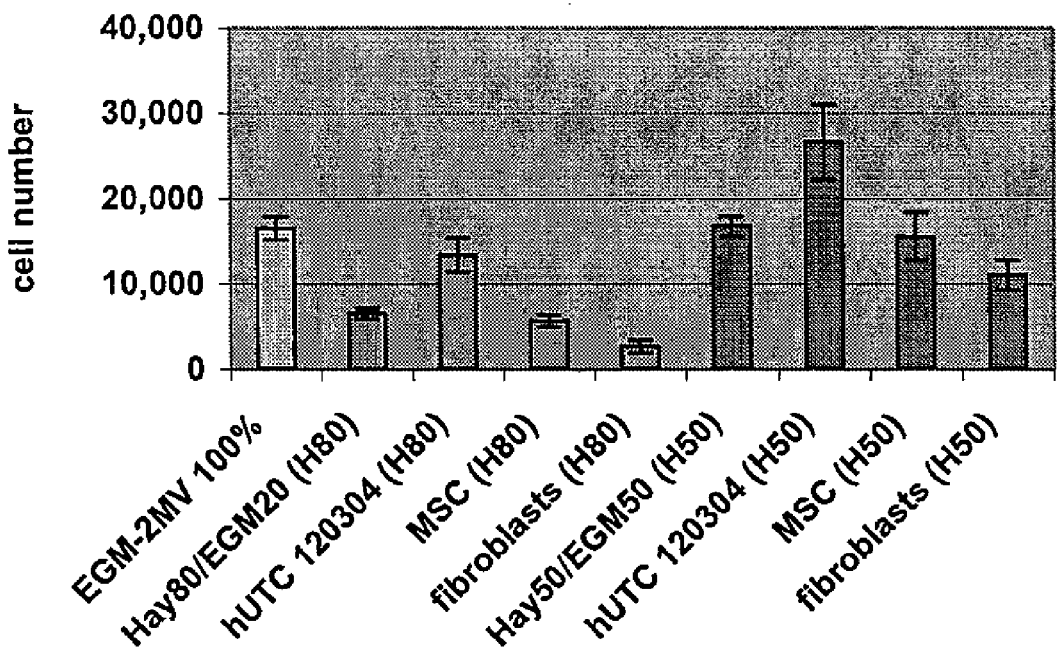
FIG. 1 shows the effect of hUTC lot#120304, MSCs, and fibroblasts on the proliferation of endothelial cells. Endothelial cells were seeded onto the bottom of a 24-well tissue culture dish at a density of 5000 cells/cm$^2$ (10,000 cells/well) and hUTC lot#120304, MSCs, or fibroblasts inside transwell inserts at a density of 5000 cells/cm$^2$ (1,650 cells/insert) in co-culture media (Hayflick 80%+EGM-2MV 20% or Hayflick 50%+EGM-2MV 50%). After 7 days of co-culture, cells were harvested and counted using a Guava® instrument. Endothelial cells were also maintained in EGM-2MV media as positive control. A, HUVECs. B, HCAECs. C, HIAECs.

Various terms are used throughout the specification and claims. Such terms are to be given their ordinary meaning in the art unless otherwise indicated. Other specifically defined terms are to be construed in a manner consistent with the definition provided herein.

Stem cells are undifferentiated cells defined by the ability of a single cell both to self-renew and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Mutt/potent cells include those able to give rise to a subset of cell lineages, but all within a particular tissue, organ, or physiological system. For example, hematopoietic stem cells (HSC) can produce progeny that include HSC (self-renewal), blood cell-restricted oligopotent progenitors, and all cell types and elements (e.g., platelets) that are normal components of the blood. Cells that are oligopotent can give rise to a more restricted subset of cell lineages than multipotent stem cells. Cells that are unipotent are able to give rise to a single cell lineage (e.g., spermatogenic stem cells).

Stem cells are also categorized on the basis of the source from which they are obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e. which cells it came from and what cells it can give rise to. The lineage of a cell places the cell within a hereditary scheme of development and differentiation.

In a broad sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase differentiates into a mesodermal, ectodermal or endodermal lineage refers to a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to, pleurigenic cells, hepatogenic cells, cells that give rise to the lining of the intestine, and cells that give rise to pancreogenic and splanchogenic cells.

The cells used in the present invention are generally referred to as referred to as umbilical cord tissue-derived cells (UTC(s) or hUTC(s)). They also may sometimes be referred to as umbilicus-derived cells (UDCs). In addition, the cells may be described as being stem or progenitor cells, the latter term being used in the broad sense. The term derived is used to indicate that the cells have been obtained from their biological source and grown or otherwise manipulated in vitro (e.g., cultured in a Growth Medium to expand the population and/or to produce a cell line). The in vitro manipulations of umbilical stem cells and the unique features of the umbilicus-derived cells of the present invention are described in detail below.

Pericytes, also known in the art as Rouget cells or mural cells, refers to the cells typically found embedded within the vascular basement membrane of blood microvessels (Armulik A et al. (2005) *Circ. Res.* 97:512-23), that are believed to play a role in, among other things, communication/signalling with endothelial cells, vasoconstriction, vasodilation, the regulation of blood flow, blood vasculature formation and development, angiogenesis, and endothelial differentiation and growth arrest (Bergers G et al. (2005) *Neuro-Oncology* 7:452-64).

Various terms are used to describe cells in culture. Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a Growth Medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

A conditioned medium is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Generally, a trophic factor is defined as a substance that promotes survival, growth, proliferation and/or maturation of a cell, or stimulates increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

As used herein, the term growth medium generally refers to a medium sufficient for the culturing of umbilical cord tissue-derived cells. In particular, one presently preferred medium for the culturing of the cells of the invention in comprises Dulbecco's Modified Essential Media (DMEM). Particularly preferred is DMEM-low glucose (DMEM-LG) (Invitrogen, Carlsbad, Calif.). The DMEM-LG is preferably supplemented with serum, most preferably fetal bovine serum or human serum. Typically, 15% (v/v) fetal bovine serum (e.g. defined fetal bovine serum, Hyclone, Logan Utah) is added, along with antibiotics/antimycotics ((preferably 100 Unit/milliliter penicillin, 100 milligrams/milliliter streptomycin, and 0.25 microgram/milliliter amphotericin B; Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to Growth Medium. In certain chemically-defined media the cells may be grown without serum present at all. In such cases, the cells may require certain growth factors, which can be added to the medium to support and sustain the cells. Presently preferred factors to be added for growth on serum-free media include one or more of bFGF, EGF, IGF-I, and PDGF. In more preferred embodiments, two, three or all four of the factors are add to serum free or chemically defined media. In other embodiments, LIF is added to serum-free medium to support or improve growth of the cells.

Also relating to the present invention, the term standard growth conditions, as used herein refers to culturing of cells at 37° C., in a standard atmosphere comprising 5% $CO_2$. Relative humidity is maintained at about 100%. While the foregoing conditions are useful for culturing, it is to be understood that such conditions are capable of being varied by the skilled artisan who will appreciate the options available in the art for culturing cells.

The term effective amount refers to a concentration or amount of a compound, material, or composition, as described herein, that is effective to achieve a particular biological result. Such results include, but are not limited to, the regeneration, repair, or improvement of skeletal tissue, the improvement of blood flow, and/or the stimulation and/or support of angiogenesis in peripheral ischemia patients. Such effective activity may be achieved, for example, by administering the cells and/or compositions of the present invention to peripheral ischemia patients. With respect to umbilical cord tissue-derived cells as administered to a patient in vivo, an effective amount may range from as few as several hundred or fewer to as many as several million or more. In specific embodiments, an effective amount may range from $10^3$-$10^{11}$, more specifically at least about $10^4$ cells. It will be appreciated that the number of cells to be administered will vary depending on the specifics of the disorder to be treated, including but not limited to size or total volume/surface area to be treated, and proximity of the site of administration to the location of the region to be treated, among other factors familiar to the medicinal biologist.

The terms treat, treating or treatment refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

The terms effective period (or time) and effective conditions refer to a period of time or other controllable conditions (e.g., temperature, humidity for in vitro methods), necessary or preferred for an agent or pharmaceutical composition to achieve its intended result.

The terms patient or subject are used interchangeably herein, and refer to animals, preferably mammals, and more preferably humans, who are treated with the pharmaceutical or therapeutic compositions or in accordance with the methods described herein.

Ischemia refers to any decrease or stoppage in the blood supply to any bodily organ, tissue, or part caused by any constriction or obstruction of the vasculature. Ischemic episode or ischemic event are used interchangeably herein and refer to any transient or permanent period of ischemia. Peripheral ischemia refers to any decrease or stoppage in the blood supply to any bodily organ, tissue, or part, excluding the heart, caused by any constriction or obstruction of the vasculature. Peripheral vascular disease (PVD) refers to diseases of the blood vessels outside the heart and brain. It often involves a narrowing of the blood vessels carrying blood to the extremities, and results from two types of circulation disorders, namely, (1) functional peripheral vascular disease that involves short-term spasm that narrows the blood vessels; and (2) organic peripheral vascular disease that involves structural changes in the blood vessels, such as caused by inflammation or fatty blockages, for example. As used herein, PVD also encompasses Raynouds, intermittent claudication and critical limb ischemia.

The term pharmaceutically acceptable carrier or medium, which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways. The biodegradation rate can vary according to the desired release rate once implanted in the body. The matrix desirably also acts as a temporary scaffold until replaced by newly grown skeletal muscle, pericytes, vascular smooth muscle, or vascular endothelial tissue. Therefore, in one embodiment, the matrix provides for sustained release of the other agents used in conjunction with the umbilical cord tissue-derived cells and may provide a structure for developing tissue growth in the patient. In other embodiments, the matrix simply provides a temporary scaffold for the developing tissue. The matrix can be in particulate form (macroparticles greater than 10 microns in diameter or microparticles less than 10 microns in diameter), or can be in the form of a structurally stable, three-dimensional implant (e.g., a scaffold). The implant can be, for example, a cube, cylinder, tube, block, film, sheet, or an appropriate anatomical form.

Several terms are used herein with respect to cell or tissue transplantation. The terms autologous transfer, autologous transplantation, autograft and the like refer to transplantation wherein the transplant donor is also the transplant recipient. The terms allogeneic transfer, allogeneic transplantation, allograft and the like refer to transplantation wherein the transplant donor is of the same species as the transplant recipient, but is not the recipient. A cell transplant in which the donor cells have been histocompatibly matched with a recipient is sometimes referred to as a syngeneic transfer. The terms xenogeneic transfer, xenogeneic transplantation, xenograft and the like refer to transplantation wherein the transplant donor is of a different species than the transplant recipient.

In its various embodiments described herein, the present invention features methods and pharmaceutical compositions for treatment of peripheral vascular disease that utilize progenitor cells and cell populations derived from umblicus tissue. These methods and pharmaceutical compositions are designed to stimulate and support angiogenesis, to improve blood flow, to regenerate, repair, and improve skeletal muscle damaged by a peripheral ischemic event, and/or to protect skeletal muscle from ischemic damage. The cells, cell populations and preparations comprising cell lysates, conditioned media and the like, used in the pharmaceutical preparations and methods of the present invention are described in detail in US Patent Publication Nos. 2005/0058631 and 2005/0054098, and also herein below.

One embodiment of the invention is a method of treating a peripheral vascular disease with an umbilical cord tissue-derived cell as described in herein. In one embodiment of the invention, the cells are provided as part of a pharmaceutical composition.

In another embodiment of the invention, the method of treating a peripheral vascular disease utilizes fibrin glue (also known as a fibrin sealant). As used herein, the term "fibrin glue" shall encompass any biological or synthetic substance used to create a fibrin clot. In one embodiment, the fibrin glue is scaffold for cell implantation. Optimally, the fibrin glue has the ability to withstand, for a sufficient period of time, its degradation inside the body. In one embodiment, the fibrin glue comprises fibrinogen (factor I), such as e.g. recombinant fibrinogen or fibrinogen purified from blood, and thrombin. In another embodiment, the fibrin glue comprises fibrinogen, thrombin, factor XIII and optionally one or more of calcium, aprotinin, fibronectin and plasminogen. In yet another embodiment, the fibrin glue comprises fibrinogen, thrombin and optionally one or more of factor XIII, anti-fribinolytic agents (e.g. transexamic acid), stabilizers (e.g. arginine hydrocholoride), calcium, aprotinin, fibronectin and plasminogen. In an alternate embodiment, the fibrin glue is substantially free of added protease inhibitors. In yet another embodiment, the fibrin glue comprises BAC2 (fibrinogen) and thrombin. In an alternate embodiment, the fibrin glue is EVICEL® fibrin glue (EVICEL® Fibrin sealant (Human), Omrix Pharmaceuticals) (thrombin and BAC2 (fibrinogen)). In one embodiment, the fibrin glue may be provided as a multi-component system, which is mixed prior to use, with one component comprising fibrin (and optionally factor XIII) and another component comprising thrombin (and optionally calcium). In another embodiment, the fibrin glue is a scaffold as described in U.S. Provisional Application No. 61/372,929 (filed Aug. 12, 2010), the disclosure of which is incorporated by reference in its entirety as it pertains to the description, characterization and use of fibrin scaffolds.

The fibrin glue may be administered simultaneously with, or before, or after umbilical-cord tissue derived cells as described herein (umbilical-derived cells). In one embodiment, the fibrin glue and umbilical-derived cells as described herein are provided in the form of a composition such as e.g. a pharmaceutical composition. In one embodiment, the composition is administered locally (such as e.g. via intramuscular injection or injection into adipose depots in muscle). In another embodiment, the fibrin glue and umbilical-derived cells as described herein are administered locally (such as e.g. via intramuscular injection or injection into adipose depots in muscle). In another embodiment, the composition, or the cells and fibrin glue, are administered by injection into interstitial spaces so as not to directly enter into circulation. In another embodiment, the method comprises providing the cells in fibrinogen to which thrombin is added immediately prior to local delivery. In one embodiment, the fibrin glue comprises from about 16 to about 24 IU/ml, alternatively from about 18 to 22 IU/ml of thrombin and from about 39.3 to about 60.7 mg/ml, alternatively from about 45 to about 60 mg/ml, alternatively from about 40 to about 55 mg/ml, alternatively from about 45 to about 55 mg/ml of fibrinogen (e.g. BAC2). In yet another embodiment, the fibrin glue comprises about 16, 17, 18, 19, 20, 21, 22, 23 or 24 IU/ml of thrombin and about 40, 43, 45, 48, 50, 52, 53, 58 or 60 mg/ml of fibrinogen. In one embodiment, about $1\times10^6$ cells are used with the fibrin glue.

According to the methods described herein, a mammalian umbilical cord is recovered upon or shortly after termination of either a full-term or pre-term pregnancy, for example, after expulsion of after birth. The umbilical cord tissue may be transported from the birth site to a laboratory in a sterile container such as a flask, beaker, culture dish, or bag. The container may have a solution or medium, including but not limited to a salt solution, such as Dulbecco's Modified Eagle's Medium (DMEM) (also known as Dulbecco's Minimal Essential Medium) or phosphate buffered saline (PBS), or any solution used for transportation of organs used for transplantation, such as University of Wisconsin solution or perfluorochemical solution. One or more antibiotic and/or antimycotic agents, such as but not limited to penicillin, streptomycin, amphotericin B, gentamicin, and nystatin, may be added to the medium or buffer. The tissue may be rinsed with an anticoagulant solution such as heparin-containing solution. It is preferable to keep the tissue at about 4-10° C. prior to extraction of umbilical cord tissue-derived cells. It is even more preferable that the tissue not be frozen prior to extraction of umbilical cord tissue-derived cells.

Isolation of umbilical-derived cells preferably occurs in an aseptic environment. The umbilical cord may be separated from the placenta by means known in the art. Blood and debris are preferably removed from the tissue prior to isolation of umbilical cord tissue-derived cells. For example, the umbilical tissue may be washed with buffer solution, including but not limited to phosphate buffered saline. The wash buffer also may comprise one or more antimycotic and/or antibiotic agents, including but not limited to penicillin, streptomycin, amphotericin B, gentamicin, and nystatin.

Umbilical tissue comprising a whole umbilical cord or a fragment or section thereof is disaggregated by mechanical force (mincing or shear forces). In a presently preferred embodiment, the isolation procedure also utilizes an enzymatic digestion process. Many enzymes are known in the art to be useful for the isolation of individual cells from complex tissue matrices to facilitate growth in culture. Digestion enzymes range from weakly digestive (e.g. deoxyribonucleases and the neutral protease, dispase) to strongly digestive (e.g. papain and trypsin), and are available commercially. A nonexhaustive list of enzymes compatible herewith includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Preferred methods involve enzymatic treatment with for example collagenase and dispase, or collagenase, dispase, and hyaluronidase. In certain embodiments, a mixture of collagenase and the neutral protease dispase are used in the dissociating step. More specific embodiments employ digestion in the presence of at least one collagenase from *Clostridium histolyticum*, and either of the protease activities, dispase and thermolysin. Still other embodiments employ digestion with both collagenase and dispase enzyme activities. Also utilized are methods that include digestion with a hyaluronidase activity in addition to collagenase and dispase activities. The skilled artisan will appreciate that many such enzyme treatments are known in the art for isolating cells from various tissue sources. For example, the enzyme blends for tissue disassociation sold under the trade name LIBERASE® (Roche, Indianapolis, Ind.) are suitable for use in the instant methods. Other sources of enzymes are known, and the skilled artisan may also obtain such enzymes directly from their natural sources. The skilled artisan is also well-equipped to assess new or additional enzymes or enzyme combinations for their utility in isolating the cells of the invention. Preferred enzyme treatments are 0.5, 1, 1.5, or 2 hours long or longer. In other preferred embodiments, the tissue is incubated at 37° C. during the enzyme treatment of the dissociation step.

In some embodiments of the invention, umbilical tissue is separated into sections comprising various aspects of the tissue, such as neonatal, neonatal/maternal, and maternal aspects of the placenta, for instance. The separated sections then are dissociated by mechanical and/or enzymatic dissociation according to the methods described herein. Cells of neonatal or maternal lineage may be identified by any means known in the art, for example, by karyotype analysis or in situ hybridization for a Y chromosome.

Isolated cells or umbilical tissue from which cells are derived may be used to initiate, or seed, cell cultures. Isolated cells are transferred to sterile tissue culture vessels either uncoated or coated with extracellular matrix or ligands such as laminin, collagen (native, denatured or crosslinked), gelatin, fibronectin, and other extracellular matrix proteins. Umbilical cord tissue-derived cells are cultured in any culture medium capable of sustaining growth of the cells such as, but not limited to, DMEM (high or low glucose), advanced DMEM, DMEM/MCDB 201, Eagle's basal medium, Ham's F10 medium (F10), Ham's F-12 medium (F12), Iscove's modified Dulbecco's medium, Mesenchymal Stem Cell Growth Medium (MSCGM), DMEM/F12, RPMI 1640, and serum/media free medium sold under the trade name CELL-GRO-FREE® (Mediatech, Inc., Herndon, Va.). The culture medium may be supplemented with one or more components including, for example, fetal bovine serum (FBS), preferably about 2-15% (v/v); equine serum (ES); human serum (HS); beta-mercaptoethanol (BME or 2-ME), preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin (EPO); amino acids, including L-valine; and one or more antibiotic and/or antimycotic agents to control microbial contamination, such as penicillin G, streptomycin sulfate, amphotericin B, gentamicin, and nystatin, either alone or in combination. The culture medium preferably comprises Growth Medium as defined in the Examples below.

The cells are seeded in culture vessels at a density to allow cell growth. In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at a temperature of about 25 to about 40° C. and more preferably are cultured at 37° C. The cells are preferably cultured in an incubator. The medium in the culture vessel can be static or agitated, for example, using a bioreactor. Umbilical cord tissue-derived cells preferably are grown under low oxidative stress (e.g., with addition of glutathione, Vitamin C, Catalase, Vitamin E, N-Acetylcysteine). "Low oxidative stress," as used herein, refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, CELL & TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston, which are incorporated herein by reference.

After culturing the isolated cells or tissue fragments for a sufficient period of time, umbilical cord tissue-derived cells will have grown out, either as a result of migration from the umbilical tissue or cell division, or both. In some embodiments of the invention, umbilical cord tissue-derived cells are passaged, or removed to a separate culture vessel containing fresh medium of the same or a different type as that used initially, where the population of cells can be mitotically expanded. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

In some aspects of the invention, the different cell types present in umbilical tissue are fractionated into subpopulations from which the umbilical cord tissue-derived cells can be isolated. Fractionation or selection may be accomplished using standard techniques for cell separation including, but not limited to, enzymatic treatment to dissociate umbilical tissue into its component cells, followed by cloning and selection of specific cell types, including but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and fluorescence activated cell sorting (FACS). For a review of clonal selection and cell separation techniques, see Freshney, 1994, CULTURE OF ANIMAL CELLS: A MANUAL OF BASIC TECHNIQUES, 3rd Ed., Wiley-Liss, Inc., New York, which is incorporated herein by reference.

The culture medium is changed as necessary, for example, by carefully aspirating the medium from the dish, for example, with a pipette, and replenishing with fresh medium. Incubation is continued until a sufficient number or density of cells accumulates in the dish. The original explanted tissue sections may be removed and the remaining cells trypsinized using standard techniques or using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be umbilical cord tissue-derived cells.

Umbilical cord tissue-derived cells may be cryopreserved. Accordingly, in a preferred embodiment described in greater detail below, umbilical cord tissue-derived cells for autologous transfer (for either the mother or child) may be derived from appropriate umbilical tissues following the birth of a child, then cryopreserved so as to be available in the event they are later needed for transplantation.

Umbilical cord tissue-derived cells may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked ImmunoSorbent Assay (ELISA)), mixed lymphocyte reaction (e.g., as measure of stimulation of PBMCs), and/or other methods known in the art.

Examples of cells derived from umbilicus tissue were deposited with the American Type Culture Collection (ATCC, 10801 University Blvd., Manassas, Va.) on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

In various embodiments, the umbilical cord tissue-derived cells possess one or more of the following growth features (1) they require L-valine for growth in culture; (2) they are capable of growth in atmospheres containing oxygen from about 5% to at least about 20% (3) they have the potential for at least about 40 doublings in culture before reaching senescence; and (4) they attach and expand on a coated or uncoated tissue culture vessel, wherein the coated tissue culture vessel comprises a coating of gelatin, laminin, collagen, polyornithine, vitronectin or fibronectin.

In certain embodiments the umbilical cord tissue-derived cells possess a normal karyotype, which is maintained as the cells are passaged. Karyotyping is particularly useful for identifying and distinguishing neonatal from maternal cells derived from placenta. Methods for karyotyping are available and known to those of skill in the art.

In other embodiments, the umbilical cord tissue-derived cells may be characterized by production of certain proteins, including (1) production of at least one of tissue factor, vimentin, and alpha-smooth muscle actin; and (2) production of at least one of CD10, CD13, CD44, CD73, CD90, PDGFr-alpha, PD-L2 and HLA-A,B,C cell surface markers, as detected by flow cytometry. In other embodiments, the umbilical cord tissue-derived cells may be characterized by lack of production of at least one of CD31, CD34, CD45, CD80, CD86, CD117, CD141, CD178, B7-H2, HLA-G, and HLA-DR,DP,DQ cell surface markers, as detected by flow cytometry. Particularly preferred are cells that produce at least two of tissue factor, vimentin, and alpha-smooth muscle actin. More preferred are those cells producing all three of the proteins tissue factor, vimentin, and alpha-smooth muscle actin.

In other embodiments, the umbilical cord tissue-derived cells may be characterized by gene expression, which relative to a human cell that is a fibroblast, a mesenchymal stem cell, or an iliac crest bone marrow cell, is increased for a gene encoding at least one of interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3.

In yet other embodiments, the umbilical cord tissue-derived cells may be characterized by gene expression, which relative to a human cell that is a fibroblast, a mesenchymal stem cell, or an iliac crest bone marrow cell, is reduced for a gene encoding at least one of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (Drosophila); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (Drosophila); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (Drosophila); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle).

In other embodiments, the umbilical cord tissue-derived cells may be characterized by secretion of at least one of MCP-1, IL-6, IL-8, GCP-2, HGF, KGF, FGF, HB-EGF, BDNF, TPO, MIP1b, RANTES, and TIMP1. In some embodiments, the umbilical cord tissue-derived cells may be characterized by lack of secretion of at least one of TGF-beta2, ANG2, PDGFbb, MIP1a and VEGF, as detected by ELISA.

In some preferred embodiments, the cells are derived from umbilical cord tissue substantially free of blood, are capable of self-renewal and expansion in culture, require L-valine for growth, can grow in at least about 5% oxygen, and comprise at least one of the following characteristics: potential for at least about 40 doublings in culture; attachment and expansion on a coated or uncoated tissue culture vessel that comprises a coating of gelatin, laminin, collagen, polyornithine, vitronectin, or fibronectin; production of vimentin and alpha-smooth muscle actin; production of CD10, CD13, CD44, CD73, and CD90; and, expression of a gene, which relative to a human cell that is a fibroblast, a mesenchymal stem cell, or an iliac crest bone marrow cell, is increased for a gene encoding interleukin 8 and reticulon 1. In some embodiments, such cells do not produce CD45 and CD117. The cells as described in this paragraph can be used in methods for treating a patient having peripheral vascular disease, can be used in pharmaceutical compositions for treating peripheral vascular disease, for example, wherein such compositions comprise the cells having these characteristics and a pharmaceutically acceptable carrier, and can be used in kits for making, using, and practicing such methods and pharmaceutical compositions as described and exemplified herein. In addition, the cells as described in this paragraph can be used to generate conditioned cell culture media or to make preparations such as cell extracts and subcellular fractions that can be used for making, using, and practicing such methods and pharmaceutical compositions as described and exemplified herein.

In preferred embodiments, the cells do not express telomerase (hTert). Accordingly, one embodiment of the invention is umbilical-derived cells that do not express telomerase (hTert) and that have one or more of the characteristics disclosed herein.

In one embodiment of the invention, the cells are isolated from human umbilical cord tissue substantially free of blood, capable of self-renewal and expansion in culture and lack the production of CD117 and/or telomerase. The cells optionally (i) express oxidized low density lipoprotein receptor 1, reticulon, chemokine receptor ligand 3, and/or granulocyte chemotactic protein; and/or (ii) do not express CD31, CD34 or CD45; and/or (iii) express, relative to a human fibroblast, mesenchymal stem cell, or iliac crest bone marrow cell, increased levels of interleukin 8 or reticulon 1; and/or (iv) have the potential to differentiate into cells of at least a skeletal muscle, vascular smooth muscle, pericyte or vascular endothelium phenotype; and/or (v) express CD10, CD13, CD44, CD73, and CD90.

In another embodiment of the invention, the cells are isolated from human umbilical cord tissue substantially free of blood, capable of self-renewal and expansion in culture and lack the production of CD117, CD34, CD31 and/or telomerase. In yet another embodiment of the invention, the cells are isolated from human umbilical cord tissue substantially free of blood, capable of self-renewal and expansion in culture and lack the production of CD117, CD45, CD34, CD31 and/or telomerase.

Among cells that are presently preferred for use with the invention in several of its aspects are umbilical cord tissue-derived cells having the characteristics described above and more particularly those wherein the cells have normal karyotypes and maintain normal karyotypes with passaging, and further wherein the cells express each of the markers CD10, CD13, CD44, CD73, CD90, PDGFr-alpha, and HLA-A,B,C, wherein the cells produce the immunologically-detectable proteins which correspond to the listed markers. Still more preferred are those cells which in addition to the foregoing do not produce proteins corresponding to any of the markers CD31, CD34, CD45, CD117, CD141, or HLA-DR,DP,DQ, as detected by flow cytometry.

Certain cells having the potential to differentiate along lines leading to various phenotypes are unstable and thus can spontaneously differentiate. Presently preferred for use with the invention are cells that do not spontaneously differentiate, for example along myoblast, skeletal muscle, vascular smooth muscle, pericyte, hemangiogenic, angiogenic, vasculogenic, or vascular endothelial lines. Preferred cells, when grown in Growth Medium, are substantially stable with respect to the cell markers produced on their surface, and with respect to the expression pattern of various genes, for example as determined using a medical diagnostic test sold under the trade name GENECHIP (Affymetrix, Inc., Santa Clara, Calif.). The cells remain substantially constant, for example in their surface marker characteristics over passaging, through multiple population doublings.

Another aspect of the invention features use of populations of the umbilical cord tissue-derived cells described above. In some embodiments, the cell population is heterogeneous. A heterogeneous cell population of the invention may comprise at least about 5%, 10%, 20%, 30%, 40%, 50%, 60%, 70%, 80%, 90%, or 95% umbilical cord tissue-derived cells of the invention. The heterogeneous cell populations of the invention may further comprise stem cells or other progenitor cells, such as myoblasts or other muscle progenitor cells, hemangioblasts, or blood vessel precursor cells, or it may further comprise fully differentiated skeletal muscle cells, smooth muscle cells, pericytes, or blood vessel endothelial cells. In some embodiments, the population is substantially homogeneous, i.e., comprises substantially only umbilical cord tissue-derived cells (preferably at least about 96%, 97%, 98%, 99% or more umbilical cord tissue-derived cells). The homogeneous cell population of the invention may comprise umbilicus- or placenta-derived cells. Homogeneous populations of umbilicus-derived cells are preferably free of cells of maternal lineage. Homogeneous populations of placenta-derived cells may be of neonatal or maternal lineage. Homogeneity of a cell population may be achieved by any method known in the art, for example, by cell sorting (e.g., flow cytometry) or by clonal expansion in accordance with known methods. Thus, preferred homogeneous cell populations may comprise a clonal cell line of umbilical cord tissue-derived cells. Such populations are particularly useful when a cell clone with highly desirable functionality has been isolated.

Also provided herein is the use of populations of cells incubated in the presence of one or more factors, or under conditions, that stimulate stem cell differentiation along a vascular smooth muscle, vascular endothelial, pericyte, or skeletal muscle pathway. Such factors are known in the art and the skilled artisan will appreciate that determination of suitable conditions for differentiation can be accomplished with routine experimentation. Optimization of such conditions can be accomplished by statistical experimental design and analysis, for example response surface methodology allows simultaneous optimization of multiple variables, for example in a biological culture. Presently preferred factors include, but are not limited to growth or trophic factors, chemokines, cytokines, cellular products, demethylating agents, and other stimuli which are now known or later determined to stimulate differentiation, for example, of stem cells along angiogenic, hemangiogenic, vasculogenic, skeletal muscle, vascular smooth muscle, pericyte, or vascular endothelial pathways or lineages.

Umbilical cord tissue-derived cells may also be genetically modified to produce therapeutically useful gene products, to produce angiogenic agents to facilitate or support additional blood vessel formation or growth, or to produce factors to recruit endothelial progenitor cells to the area of ischemic damage. Endothelial progenitor cells facilitate vasculogenesis and blood flow, particularly following an ischemic event (Urbich C and Dimmeler S (2004) *Circ. Res.* 95:343-53). Factors that play a role in endothelial cell recruitment include, but are not limited to VEGF, stromal derived factor-1 (SDF-1), erythropoietin (EPO), G-CSF, statins, strogen, PPARγ, CXCR4, FGF, and HGF. Genetic modification may be accomplished using any of a variety of vectors including, but not limited to, integrating viral vectors, e.g., retrovirus vector or adeno-associated viral vectors; non-integrating replicating vectors, e.g., papilloma virus vectors, SV40 vectors, adenoviral vectors; or replication-defective viral vectors. Other methods of introducing DNA into cells include the use of liposomes, electroporation, a particle gun, or by direct DNA injection.

Hosts cells are preferably transformed or transfected with DNA controlled by or in operative association with, one or more appropriate expression control elements such as promoter or enhancer sequences, transcription terminators, polyadenylation sites, among others, and a selectable marker. Any promoter may be used to drive the expression of the inserted gene. For example, viral promoters include, but are not limited to, the CMV promoter/enhancer, SV40, papillomavirus, Epstein-Barr virus or elastin gene promoter. In some embodiments, the control elements used to control expression of the gene of interest can allow for the regulated expression of the gene so that the product is synthesized only when needed in vivo. If transient expression is desired, constitutive promoters are preferably used in a non-integrating and/or replication-defective vector. Alternatively, inducible promoters could be used to drive the expression of the inserted gene when necessary. Inducible promoters include, but are not limited to, those associated with metallothionein and heat shock proteins.

Following the introduction of the foreign DNA, engineered cells may be allowed to grow in enriched media and then switched to selective media. The selectable marker in the foreign DNA confers resistance to the selection and allows cells to stably integrate the foreign DNA as, for example, on a plasmid, into their chromosomes and grow to form foci which, in turn, can be cloned and expanded into cell lines. This method can be advantageously used to engineer cell lines that express the gene product.

The cells of the invention may be genetically engineered to "knock out" or "knock down" expression of factors that promote inflammation or rejection at the implant site. Negative modulatory techniques for the reduction of target gene expression levels or target gene product activity levels are discussed below. "Negative modulation," as used herein, refers to a reduction in the level and/or activity of target gene product relative to the level and/or activity of the target gene product in the absence of the modulatory treatment. The expression of a gene native to a skeletal muscle cell, vascular smooth muscle cell, pericyte, vascular endothelial cell, or progenitor cells thereof can be reduced or knocked out using a number of techniques including, for example, inhibition of expression by inactivating the gene using the homologous recombination technique. Typically, an exon encoding an important region of the protein (or an exon 5' to that region) is interrupted by a positive selectable marker, e.g., neo, preventing the production of normal mRNA from the target gene and resulting in inactivation of the gene. A gene may also be inactivated by creating a deletion in part of a gene, or by deleting the entire gene. By using a construct with two regions of homology to the target gene that are far apart in the genome, the sequences intervening the two regions can be deleted (Mombaerts et al., 1991, *Proc. Nat. Acad. Sci. U.S.A.*

88:3084-3087). Antisense, DNAzymes, ribozymes, small interfering RNA (siRNA) and other such molecules that inhibit expression of the target gene can also be used to reduce the level of target gene activity. For example, antisense RNA molecules that inhibit the expression of major histocompatibility gene complexes (HLA) have been shown to be most versatile with respect to immune responses. Still further, triple helix molecules can be utilized in reducing the level of target gene activity. These techniques are described in detail by L. G. Davis et al. (eds), 1994, BASIC METHODS IN MOLECULAR BIOLOGY, 2nd ed., Appleton & Lange, Norwalk, Conn.

In other aspects, the invention utilizes cell lysates and cell soluble fractions prepared from umbilical cord tissue-derived cells, or heterogeneous or homogeneous cell populations comprising umbilical cord tissue-derived cells, as well as umbilical cord tissue-derived cells or populations thereof that have been genetically modified or that have been stimulated to differentiate along a skeletal muscle, vascular smooth muscle, pericyte, or vascular endothelium pathway. Such lysates and fractions thereof have many utilities. Use of the cell lysate soluble fraction (i.e., substantially free of membranes) in vivo, for example, allows the beneficial intracellular milieu to be used allogeneically in a patient without introducing an appreciable amount of the cell surface proteins most likely to trigger rejection, or other adverse immunological responses. Methods of lysing cells are well-known in the art and include various means of mechanical disruption, enzymatic disruption, or chemical disruption, or combinations thereof. Such cell lysates may be prepared from cells directly in their Growth Medium and thus containing secreted growth factors and the like, or may be prepared from cells washed free of medium in, for example, PBS or other solution. Washed cells may be resuspended at concentrations greater than the original population density if preferred.

In one embodiment, whole cell lysates are prepared, e.g., by disrupting cells without subsequent separation of cell fractions. In another embodiment, a cell membrane fraction is separated from a soluble fraction of the cells by routine methods known in the art, e.g., centrifugation, filtration, or similar methods.

Cell lysates or cell soluble fractions prepared from populations of umbilical cord tissue-derived cells may be used as is, further concentrated, by for example, ultrafiltration or lyophilization, or even dried, partially purified, combined with pharmaceutically-acceptable carriers or diluents as are known in the art, or combined with other compounds such as biologicals, for example pharmaceutically useful protein compositions. Cell lysates or fractions thereof may be used in vitro or in vivo, alone or for example, with autologous or syngeneic live cells. The lysates, if introduced in vivo, may be introduced locally at a site of treatment, or remotely to provide, for example needed cellular growth factors to a patient.

In a further embodiment, umbilical cord tissue-derived cells can be cultured in vitro to produce biological products in high yield. Umbilical cord tissue-derived cells that either naturally produce a particular biological product of interest (e.g., a trophic factor), or that have been genetically engineered to produce a biological product, can be clonally expanded using the culture techniques described herein. Alternatively, cells may be expanded in a medium that induces differentiation to a skeletal muscle, vascular smooth muscle, pericyte, or vascular endothelial lineage. In each case, biological products produced by the cell and secreted into the medium can be readily isolated from the conditioned medium using standard separation techniques, e.g., such as differential protein precipitation, ion-exchange chromatography, gel filtration chromatography, electrophoresis, and HPLC, to name a few. A "bioreactor" may be used to take advantage of the flow method for feeding, for example, a three-dimensional culture in vitro. Essentially, as fresh media is passed through the three-dimensional culture, the biological product is washed out of the culture and may then be isolated from the outflow, as above.

Alternatively, a biological product of interest may remain within the cell and, thus, its collection may require that the cells be lysed, as described above. The biological product may then be purified using any one or more of the above-listed techniques.

In other embodiments, the invention utilizes conditioned medium from cultured umbilical cord tissue-derived cells for use in vitro and in vivo as described below. Use of the cell conditioned medium allows the beneficial trophic factors secreted by the umbilical cord tissue-derived cells to be used allogeneically in a patient without introducing intact cells that could trigger rejection, or other adverse immunological responses. Conditioned medium is prepared by culturing cells in a culture medium, then removing the cells from the medium.

Conditioned medium prepared from populations of umbilical cord tissue-derived cells may be used as is, further concentrated, for example, by ultrafiltration or lyophilization, or even dried, partially purified, combined with pharmaceutically-acceptable carriers or diluents as are known in the art, or combined with other compounds such as biologicals, for example pharmaceutically useful protein compositions. Conditioned medium may be used in vitro or in vivo, alone or combined with autologous or syngeneic live cells, for example. The conditioned medium, if introduced in vivo, may be introduced locally at a site of treatment, or remotely to provide needed cellular growth or trophic factors to a patient.

In another embodiment, an extracellular matrix (ECM) produced by culturing umbilical cord tissue-derived cells on liquid, solid or semi-solid substrates is prepared, collected and utilized as an alternative to implanting live cells into a subject in need of tissue repair or replacement. Umbilical cord tissue-derived cells are cultured in vitro, on a three dimensional framework as described elsewhere herein, under conditions such that a desired amount of ECM is secreted onto the framework. The cells comprising the new tissue are removed, and the ECM processed for further use, for example, as an injectable preparation. To accomplish this, cells on the framework are killed and any cellular debris removed from the framework. This process may be carried out in a number of different ways. For example, the living tissue can be flash-frozen in liquid nitrogen without a cryopreservative, or the tissue can be immersed in sterile distilled water so that the cells burst in response to osmotic pressure.

Once the cells have been killed, the cellular membranes may be disrupted and cellular debris removed by treatment with a mild detergent rinse, such as Ethylenediaminetetraacetic acid (EDTA), 3-[(3-cholamidopropyl)dimethylammonio]-1-propanesulfonate (CHAPS) or a zwitterionic detergent. Alternatively, the tissue can be enzymatically digested and/or extracted with reagents that break down cellular membranes and allow removal of cell contents. Examples of such enzymes include, but are not limited to, hyaluronidase, dispase, proteases, and nucleases. Examples of detergents include non-ionic detergents such as, for example, alkylaryl polyether alcohol (TRITON X-100), octylphenoxy polyethoxy-ethanol (Rohm and Haas, Philadelphia, Pa.), BRIJ-35, a polyethoxyethanol lauryl ether (Atlas Chemical Co., San Diego, Calif.), polysorbate 20 (TWEEN 20), a polyethoxyethanol sorbitan monolaureate (Rohm and Haas, Philadelphia, Pa.), polyethylene lauryl ether (Rohm and Haas, Philadelphia, Pa.); and ionic detergents such as sodium dodecyl sulfate, sulfated higher aliphatic alcohols, sulfonated alkanes and sulfonated alkylarenes containing 7 to 22 carbon atoms in a branched or unbranched chain.

The collection of the ECM can be accomplished in a variety of ways, depending at least in part on whether the new tissue has been formed on a three-dimensional framework that is biodegradable or non-biodegradable, as in the case of metals. For example, if the framework is non-biodegradable, the ECM can be removed by subjecting the framework to sonication, high pressure water jets, mechanical scraping, or mild treatment with detergents or enzymes, or any combination of the above.

If the framework is biodegradable, the ECM can be collected, for example, by allowing the framework to degrade or dissolve in solution. Alternatively, if the biodegradable framework is composed of a material that can itself be injected along with the ECM, the framework and the ECM can be processed in toto for subsequent injection. Alternatively, the ECM can be removed from the biodegradable framework by any of the methods described above for collection of ECM from a non-biodegradable framework. All collection processes are preferably designed so as not to denature the ECM.

After it has been collected, the ECM may be processed further. For example, the ECM can be homogenized to fine particles using techniques well known in the art such as by sonication, so that it can pass through a surgical needle. The components of the ECM can also be crosslinked, if desired, by gamma irradiation. Preferably, the ECM can be irradiated between 0.25 to 2 mega rads to sterilize and crosslink the ECM. Chemical crosslinking using agents that are toxic, such as glutaraldehyde, is possible but not generally preferred.

The amounts and/or ratios of proteins, such as the various types of collagen present in the ECM, may be adjusted by mixing the ECM produced by the cells of the invention with ECM of one or more other cell types. In addition, biologically active substances such as proteins, growth factors and/or drugs, can be incorporated into the ECM. Exemplary biologically active substances include tissue growth factors, such as TGF-beta, and the like, which promote healing and tissue repair at the site of the injection. Such additional agents may be utilized in any of the embodiments described herein above, e.g., with whole cell lysates, soluble cell fractions, or further purified components and products produced by the umbilical cord tissue-derived cells.

In another aspect, the invention provides pharmaceutical compositions that utilize the umbilical cord tissue-derived cells, umbilical cord tissue-derived cell populations, components and products of umbilical cord tissue-derived cells in various methods for the treatment of injury or damage caused by a peripheral ischemic episode. Certain embodiments encompass pharmaceutical compositions comprising live cells (umbilical cord tissue-derived cells alone or admixed with other cell types). Other embodiments encompass pharmaceutical compositions comprising umbilical cord tissue-derived cell cellular components (e.g., cell lysates, soluble cell fractions, conditioned medium, ECM, or components of any of the foregoing) or products (e.g., trophic and other biological factors produced naturally by umbilical cord tissue-derived cells or through genetic modification, conditioned medium from umbilical cord tissue-derived cell culture). In either case, the pharmaceutical composition may further comprise other active agents, such as anti-inflammatory agents, anti-apoptotic agents, antioxidants, growth factors, myotrophic factors or myoregenerative or myoprotective drugs as known in the art.

Examples of other components that may be added to the pharmaceutical compositions include, but are not limited to: (1) other myobeneficial or myoprotective drugs, or angiobeneficial or angioprotective drugs; (2) selected extracellular matrix components, such as one or more types of collagen known in the art, and/or growth factors, platelet-rich plasma, and drugs (alternatively, umbilical cord tissue-derived cells may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-1 inhibitors, Pemirolast, Tranilast, REMICADE® (Centocor, Inc., Malvern, Pa.), Sirolimus, and non-steroidal anti-inflammatory drugs (NSAIDS) (such as Tepoxalin, Tolmetin, and Suprafen); (5) immunosuppressive or immunomodulatory agents, such as calcineurin inhibitors, mTOR inhibitors, antiproliferatives, corticosteroids and various antibodies; (6) antioxidants such as probucol, vitamins C and E, coenzyme Q-10, glutathione, L-cysteine and N-acetylcysteine; (6) local anesthetics; (7) trophic factors such as Agrin, VEGF, VEGF-B, VEGF-C, VEGF-D, NEGF-1, NEGF-2, PDGF, GDF, IGF1, IGF2, EGF, and FGF; and, (8) factors that function in the recruitment and incorporation of endothelial progenitor cells into ischemic tissue, such as VEGF, SDF-1, EPO, G-CSF, statins, estrogen, PPARγ, and CXCR4, to name only a few.

Pharmaceutical compositions of the invention comprise umbilical cord tissue-derived cells, components or products thereof, including preparations made from umbilical cord tissue-derived cells, formulated with a pharmaceutically acceptable carrier or medium. Suitable pharmaceutically acceptable carriers include water, salt solution (such as Ringer's solution), alcohols, oils, gelatins, polyvinyl pyrrolidine, carbohydrates (such as lactose, amylose, or starch, fatty acid esters), and hydroxymethylcellulose. Such preparations can be sterilized, and if desired, mixed with auxiliary agents such as lubricants, preservatives, stabilizers, wetting agents, emulsifiers, salts for influencing osmotic pressure, buffers, and coloring agents. Pharmaceutical carriers suitable for use in the present invention are known in the art and are described, for example, in Pharmaceutical Sciences ($17^{th}$ Ed., Mack Pub. Co., Easton, Pa.) and WO 96/05309.

Typically, but not exclusively, pharmaceutical compositions comprising umbilical cord tissue-derived cell components or products, but not live cells, are formulated as liquids (or as solid tablets, capsules and the like, when oral delivery is appropriate). These may be formulated for administration by any acceptable route known in the art to achieve delivery of drugs and biological molecules to the target skeletal muscle, vascular smooth muscle, pericyte, or vascular endothelial tissue, including, but not limited to, oral, nasal, ophthalmic and parenteral, including intravenous. Particular routes of parenteral administration include, but are not limited to, intramuscular, subcutaneous, intraperitoneal, intrathecal, intracisternal, or via syringes with needles or catheters with or without pump devices.

Pharmaceutical compositions comprising live umbilical cord tissue-derived cells are typically formulated as liquids, semisolids (e.g., gels (including fibrin glue)) or solids (e.g., matrices, scaffolds and the like, as appropriate for vascular or skeletal muscle tissue engineering). Liquid compositions are formulated for administration by any acceptable route known in the art to achieve delivery of live cells to the target vascular or skeletal muscle tissues. Typically, these include injection or infusion, either in a diffuse fashion, or targeted to the site of peripheral ischemic injury, damage, or distress, by a route of administration including, but not limited to, intramuscular, intravenous, or intra-arterial delivery via syringes with needles and/or catheters with or without pump devices.

Pharmaceutical compositions comprising live cells in a semi-solid or solid carrier are typically formulated for surgical implantation at the site of ischemic injury, damage, or distress. It will be appreciated that liquid compositions also may be administered by surgical procedures. In particular embodiments, semi-solid or solid pharmaceutical compositions may comprise semi-permeable gels, lattices, cellular scaffolds and the like, which may be non-biodegradable or biodegradable. For example, in certain embodiments, it may be desirable or appropriate to sequester the exogenous cells from their surroundings, yet enable the cells to secrete and deliver biological molecules (e.g. myotrophic factors, angiotrophic factors, or endothelial progenitor cell recruitment factors) to surrounding skeletal muscle or vascular cells. In these embodiments, cells may be formulated as autonomous implants comprising living umbilical cord tissue-derived cells or cell population comprising umbilical cord tissue-derived cells surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression (for a review of such devices and methods, see, e.g., P. A. Tresco et al., (2000) *Adv. Drug Delivery Rev.* 42:3-27).

In other embodiments, different varieties of degradable gels and networks are utilized for the pharmaceutical compositions of the invention. For example, degradable materials particularly suitable for sustained release formulations include biocompatible polymers, such as poly(lactic acid), poly (lactic acid-co-glycolic acid), methylcellulose, hyaluronic acid, collagen, and the like. The structure, selection and use of degradable polymers in drug delivery vehicles have been reviewed in several publications, including, A. Domb et al., 1992, *Polymers for Advanced Technologies* 3:279-292.

In other embodiments, it may be desirable or appropriate to deliver the cells on or in a biodegradable, preferably bioresorbable or bioabsorbable, scaffold or matrix. These typically three-dimensional biomaterials contain the living cells attached to the scaffold, dispersed within the scaffold, or incorporated in an extracellular matrix entrapped in the scaffold. Once implanted into the target region of the body, these implants become integrated with the host tissue, wherein the transplanted cells gradually become established (see, e.g., Tresco, Pa., et al. (2000) supra; see also Hutmacher, D W (2001) *J. Biomater. Sci. Polymer Edn.* 12:107-174).

The biocompatible matrix may be comprised of natural, modified natural or synthetic biodegradable polymers, including homopolymers, copolymers and block polymers, as well as combinations thereof. It is noted that a polymer is generally named based on the monomer from which it is synthesized.

Examples of suitable biodegradable polymers or polymer classes include fibrin, collagen, elastin, gelatin, vitronectin, fibronectin, laminin, thrombin, poly(aminoacid), oxidized cellulose, tropoelastin, silk, ribonucleic acids, deoxyribonucleic acids; proteins, polynucleotides, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof. For both glycolic acid and lactic acid, an intermediate cyclic dimer is typically prepared and purified prior to polymerization. These intermediate dimers are called glycolide and lactide, respectively. Other useful biodegradable polymers or polymer classes include, without limitation, aliphatic polyesters, poly(alkylene oxalates), tyrosine derived polycarbonates, polyiminocarbonates, polyorthoesters, polyoxaesters, polyamidoesters, polyoxaesters containing amine groups, poly(propylene fumarate), polydioxanones, polycarbonates, polyoxalates, poly(alpha-hydroxyacids), poly(esters), polyurethane, poly(ester urethane), poly(ether urethane), polyanhydrides, polyacetates, polycaprolactones, poly(orthoesters), polyamino acids, polyamides and blends and copolymers thereof. Additional useful biodegradable polymers include, without limitation stereopolymers of L- and D-lactic acid, copolymers of bis(para-carboxyphenoxy) propane and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, poly(hydroxyalkanoates) and mixtures thereof. Binary and ternary systems also are contemplated.

In general, a suitable biodegradable polymer for use as the matrix is desirably configured so that it has mechanical properties that are suitable for the intended application, remains sufficiently intact until tissue has in-grown and healed, does not invoke an inflammatory or toxic response, is metabolized in the body after fulfilling its purpose, is easily processed into the desired final product to be formed, demonstrates acceptable shelf-life, and is easily sterilized.

In one aspect of the invention, the biocompatible polymer used to form the matrix is in the form of a hydrogel. In one embodiment of the invention, the hydrogel comprisese a fibrin glue. In general, hydrogels are cross-linked polymeric materials that can absorb more than 20% of their weight in water while maintaining a distinct three-dimensional structure. This definition includes dry cross-linked polymers that will swell in aqueous environments, as well as water-swollen materials. A host of hydrophilic polymers can be cross-linked to produce hydrogels, whether the polymer is of biological origin, semi-synthetic, or wholly synthetic. The hydrogel may be produced from a synthetic polymeric material. Such synthetic polymers can be tailored to a range of properties and predictable lot-to-lot uniformity, and represent a reliable source of material that generally is free from concerns of immunogenicity. The matrices may include hydrogels formed from self assembling peptides, as those discussed in U.S. Pat. Nos. 5,670,483 and 5,955,343, U.S. Pub. App. No. 2002/0160471, and PCT Publication No. WO 02/062969.

Properties that make hydrogels valuable in drug delivery applications include the equilibrium swelling degree, sorption kinetics, solute permeability, and their in vivo performance characteristics. Permeability to compounds depends in part upon the swelling degree or water content and the rate of biodegradation. Since the mechanical strength of a gel declines in direct proportion to the swelling degree, it is also well within the contemplation of the present invention that the hydrogel can be attached to a substrate so that the composite system enhances mechanical strength. In some embodiments, the hydrogel can be impregnated within a porous substrate, so as to gain the mechanical strength of the substrate, along with the useful delivery properties of the hydrogel.

Non-limiting examples of scaffold or matrix (sometimes referred to collectively as "framework") that may be used in the present invention include textile structures such as weaves, knits, braids, meshes, non-wovens, and warped knits; porous foams, semi-porous foams, perforated films or sheets, microparticles, beads, and spheres and composite structures being a combination of the above structures. Nonwoven mats may, for example, be formed using fibers comprised of a synthetic absorbable copolymer of glycolic and lactic acids (PGA/PLA), sold under the tradename VICRYL sutures (Ethicon, Inc., Somerville, N.J.). Foams, composed of, for example, poly(epsilon-caprolactone)/poly(glycolic acid) (PCL/PGA) copolymer, formed by processes such as freeze-drying, or lyophilized, as discussed in U.S. Pat. No. 6,355,699, also may be utilized. Hydrogels such as self-assembling peptides (e.g., RAD16) may also be used. In situ-forming degradable networks are also suitable for use in the invention (see, e.g., Anseth, K S et al. (2002) *J. Controlled Release* 78:199-209; Wang, D. et al., (2003) *Biomaterials* 24:3969-3980; U.S. Patent Publication 2002/0022676 to He et al.). These in situ forming materials are formulated as fluids suitable for injection, and then may be induced to form a hydrogel by a variety of means such as change in temperature, pH, and exposure to light in situ or in vivo.

In another embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, cells are seeded onto foam scaffolds that may be composite structures.

In many of the abovementioned embodiments, the framework may be molded into a useful shape, such as that of a blood vessel. Furthermore, it will be appreciated that umbilical cord tissue-derived cells may be cultured on pre-formed, non-degradable surgical or implantable devices, e.g., in a manner corresponding to that used for preparing fibroblast-containing GDC endovascular coils, for instance (Marx, W F et al., (2001) *Am. J. Neuroradiol.* 22:323-333).

The matrix, scaffold or device may be treated prior to inoculation of cells in order to enhance cell attachment. For example, prior to inoculation, nylon matrices can be treated with 0.1 molar acetic acid and incubated in polylysine, PBS, and/or collagen to coat the nylon. Polystyrene can be similarly treated using sulfuric acid. The external surfaces of a framework may also be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), genetic materials such as cytokines and growth factors, a cellular matrix, and/or other materials, including but not limited to, gelatin, alginates, agar, agarose, and plant gums, among other factors affecting cell survival and differentiation.

hUTC-containing frameworks are prepared according to methods known in the art. For example, cells can be grown freely in a culture vessel to sub-confluency or confluency, lifted from the culture and inoculated onto the framework. Growth factors may be added to the culture medium prior to, during, or subsequent to inoculation of the cells to trigger differentiation and tissue formation, if desired. Alternatively, the frameworks themselves may be modified so that the growth of cells thereon is enhanced, or so that the risk of rejection of the implant is reduced. Thus, one or more biologically active compounds, including, but not limited to, anti-inflammatory compounds, immunosuppressants or growth factors, may be added to the framework for local release.

Umbilical cord tissue-derived cells, parts of umbilical cord tissue-derived cells, or cell populations comprising umbilical cord tissue-derived cells, or components of or products produced by umbilical cord tissue-derived cells, may be used in a variety of ways to support and facilitate the repair, regeneration, and improvement of skeletal muscle cells and tissues, to improve blood flow, and to stimulate and/or support angiogenesis, especially in peripheral vascular disease patients. Such utilities encompass in vitro, ex vivo and in vivo methods.

In one embodiment, as discussed above, umbilical cord tissue-derived cells can be cultured in vitro to produce biological products that are either naturally produced by the cells, or produced by the cells when induced to differentiate into skeletal muscle, vascular smooth muscle, pericyte, or vascular endothelial lineages, or produced by the cells via genetic modification. For instance, TIMP1, TPO, KGF, HGF, FGF, HBEGF, BDNF, MIP1b, MCP1, RANTES, I309, TARC, MDC, and IL-8 were found to be secreted from umbilicus-derived cells grown in Growth Medium. In addition, factors for endothelial progenitor cell recruitment such as VEGF, SDF-1, EPO, G-CSF, statins, estrogen, PPARγ, and CXCR4 may be produced by umbilical cord tissue-derived cells and may be secreted into the growth medium. Other trophic factors, as yet undetected or unexamined, for use in skeletal muscle or vascular repair and regeneration, are likely to be produced by umbilical cord tissue-derived cells and possibly secreted into the medium.

In this regard, another embodiment of the invention features use of umbilical cord tissue-derived cells for production of conditioned medium, either from undifferentiated umbilical cord tissue-derived cells or from umbilical cord tissue-derived cells incubated under conditions that stimulate differentiation into a skeletal muscle or vascular lineage. Such conditioned media are contemplated for use in in vitro or ex vivo culture of skeletal muscle, vascular smooth muscle, pericyte, or vascular endothelial precursor cells, or in vivo to support transplanted cells comprising homogeneous populations of umbilical cord tissue-derived cells or heterogeneous populations comprising umbilical cord tissue-derived cells and skeletal muscle, vascular smooth muscle, pericyte, or vascular endothelial progenitors, or to recruit endothelial progenitor cells to the site of ischemic injury, for example.

Yet another embodiment comprises the use of hUTC cell lysates, soluble cell fractions or components thereof, or ECM or components thereof, for a variety of purposes. As mentioned above, some of these components may be used in pharmaceutical compositions. In other embodiments, a cell lysate or ECM is used to coat or otherwise treat substances or devices to be used surgically, or for implantation, or for ex vivo purposes, to promote healing or survival of cells or tissues contacted in the course of such treatments. In some preferred embodiments, such preparations made from umbilical cord tissue-derived cells comprise FGF and HGF.

In another embodiment, umbilical cord tissue-derived cells are used advantageously in co-cultures in vitro to provide trophic support to other cells, in particular, skeletal muscle cells, skeletal muscle progenitor cells, vascular smooth muscle cells, vascular smooth muscle progenitor cells, pericytes, vascular endothelial cells, or vascular endothelium progenitor cells. In some preferred embodiments, the trophic support is proliferation of the cells. For co-culture, it may be desirable for the umbilical cord tissue-derived cells and the desired other cells to be co-cultured under conditions in which the two cell types are in contact. This can be achieved, for example, by seeding the cells as a heterogeneous population of cells in culture medium or onto a suitable culture substrate. Alternatively, the umbilical cord tissue-derived cells can first be grown to confluence, and then will serve as a substrate for the second desired cell type in culture. In this latter embodiment, the cells may further be physically separated, e.g., by a membrane or similar device, such that the other cell type may be removed and used separately, following the co-culture period. Use of umbilical cord tissue-derived cells in co-culture to promote expansion and differentiation of skeletal muscle or vascular cell types may find applicability in research and in clinical/therapeutic areas. For instance, umbilical cord tissue-derived cell co-culture may be utilized to facilitate growth and differentiation of skeletal muscle, vascular smooth muscle, pericytes, or vascular endothelial cells in culture, for basic research purposes or for use in drug screening assays, for example. Umbilical cord tissue-derived cell co-culture may also be utilized for ex vivo expansion of skeletal muscle, vascular smooth muscle, pericyte, or vascular endothelium progenitors for later administration for therapeutic purposes. For example, skeletal muscle, vascular smooth muscle, pericyte, or vascular endothelium progenitor cells may be harvested from an individual, expanded ex vivo in co-culture with umbilical cord tissue-derived cells, then returned to that individual (autologous transfer) or another individual (syngeneic or allogeneic transfer). In these embodiments, it will be appreciated that, following ex vivo expansion, the mixed population of cells comprising the umbilical cord tissue-derived cells and skeletal muscle, vascular smooth muscle, pericyte, or vascular endothelium progenitors could be administered to a patient in need of treatment. Alternatively, in situations where autologous transfer is appropriate or desirable, the co-cultured cell populations may be physically separated in culture, enabling removal of the autologous skeletal muscle, vascular smooth muscle, or vascular endothelium progenitors for administration to the patient.

As described in U.S. Patent Publication Nos. 2005/0058631, 2005/0054098 and 2005/0058630, umbilical cord tissue-derived cells have been shown to be effectively transplanted into the body, and to improve blood flow and reduce tissue necrosis in an accepted animal model. Those findings, along with the discoveries set forth in the present invention, support preferred embodiments of the invention, wherein umbilical cord tissue-derived cells are used in cell therapy for treating ischemic injury or damage by repairing or regenerating skeletal muscle and/or vascular tissue in a peripheral vascular disease patient, or by improving blood flow or stimulating and/or supporting angiogenesis in a peripheral vascular disease patient. In one embodiment, the umbilical cord tissue-derived cells are transplanted into a target location in the body, especially at or proximal to the location of the ischemic episode, where the umbilical cord tissue-derived cells can differentiate into one or more of skeletal muscle, vascular smooth muscle, pericyte, or vascular endothelium phenotypes, the umbilical cord tissue-derived cells can provide trophic support for skeletal muscle cell, vascular smooth muscle cell, pericyte, or vascular endothelial cell progenitors and/or skeletal muscle cells, vascular smooth muscle cells, pericytes, or vascular endothelial cells in situ, the umbilical cord tissue-derived cells can produce factors to recruit endothelial progenitor cells to the site of the ischemic injury, or the umbilical cord tissue-derived cells can exert a beneficial effect in two or more of those fashions, among others. Umbilical cord tissue-derived cells secrete trophic factors including, but not limited to GFGFm, IL-6, IL-8, HGF, IGF-1, TPO, and the like. Umbilical cord tissue-derived cells can aid in the recruitment of vascular progenitor cells such as angioblasts to stimulate new blood vessel formation.

Umbilical cord tissue-derived cells can exert trophic effects in the body of the patient to which they are administered. For example, umbilical cord tissue-derived cells can exert trophic effects on skeletal muscle cells, vascular smooth muscle cells, vascular endothelial cells, pericytes, or progenitor cells thereof. In some preferred embodiments, the trophic effect is the proliferation of such cells. Umbilical cord tissue-derived cells can also induce migration of cells in the body of the patient to which they are administered. Such migration can facilitate the repair, regeneration, and treatment of peripheral vascular disease such as peripheral ischemia. For example, umbilical cord tissue-derived cells administered at or near a site of peripheral vascular disease can induce migration of cells to the site of peripheral vascular disease in order to repair, regenerate, or otherwise treat the diseased tissue and its surroundings. Umbilical cord tissue-derived cells so administered can induce migration of skeletal muscle cells, vascular smooth muscle cells, vascular endothelial cells, pericytes, or progenitor cells thereof. In preferred embodiments, umbilical cord tissue-derived cells induce migration of vascular endothelial cells and/or vascular endothelium progenitor cells to the site, or at least near to the site of the peripheral vascular disease. In some embodiments, migration is induced or supported by FGF and/or HGF, preferably FGF and HGF expressed by the umbilical cord tissue-derived cells. Preparations made from umbilical cord tissue-derived cells, including cell lysates, subcellular fractions, and the like, can also be used to treat peripheral vascular disease. Such preparations can be formulated with pharmaceutically acceptable carriers such as those described and exemplified herein, and administered to patients in amounts effective to treat peripheral vascular disease. In preferred embodiments, preparations made from umbilical cord tissue-derived cells comprise FGF and HGF.

Specific embodiments of the invention are directed to the direct repair, regeneration, replacement of, or the support of the repair, regeneration, or replacement of blood vessels for the treatment of peripheral ischemic injury or damage.

Umbilical cord tissue-derived cells may be administered alone (e.g., as substantially homogeneous populations) or as admixtures with other cells. As described above, umbilical cord tissue-derived cells may be administered as formulated in a pharmaceutical preparation with a matrix or scaffold, or with conventional pharmaceutically acceptable carriers. Where umbilical cord tissue-derived cells are administered with other cells, they may be administered simultaneously or sequentially with the other cells (either before or after the other cells). Cells that may be administered in conjunction with umbilical cord tissue-derived cells include, but are not limited to, myocytes, skeletal muscle cells, skeletal muscle progenitor cells, vascular smooth muscle cells, vascular smooth muscle progenitor cells, pericytes, vascular endothelial cells, or vascular endothelium progenitor cells, and/or other multipotent or pluripotent stem cells. The cells of different types may be admixed with the umbilical cord tissue-derived cells immediately or shortly prior to administration, or they may be co-cultured together for a period of time prior to administration.

The umbilical cord tissue-derived cells may be administered with other beneficial drugs or biological molecules, or other active agents, such as anti-inflammatory agents, anti-apoptotic agents, antioxidants, growth factors, angiogenic factors, or myoregenerative or myoprotective drugs as known in the art. When umbilical cord tissue-derived cells are administered with other agents, they may be administered together in a single pharmaceutical composition, or in separate pharmaceutical compositions, simultaneously or sequentially with the other agents (either before or after administration of the other agents). The other agents may be a part of a treatment regimen that begins either before transplantation and continuing throughout the course of recovery, or may be initiated at the time of transplantation, or even after transplantation, as a physician of skill in the art deems appropriate.

Examples of other components that may be administered with umbilical cord tissue-derived cells include, but are not limited to: (1) other angiogenic factors, angiogenic drugs, or myoregenerative or myooprotective factors or drugs; (2) selected extracellular matrix components, such as one or more types of collagen known in the art, and/or growth factors, platelet-rich plasma, and drugs (alternatively, umbilical cord tissue-derived cells may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, statins, IL-6 and IL-1 inhibitors, Pemirolast, Tranliast, REMICADE® (Centocor, Inc., Malvern, Pa.), Sirolimus, and non-steroidal anti-inflammatory drugs (NSAIDS) (such as Tepoxalin, Tolmetin, and Suprafen); (5) immunosuppressive or immunomodulatory agents, such as calcineurin inhibitors, mTOR inhibitors, antiproliferatives, corticosteroids and various antibodies; (6) antioxidants such as probucol, vitamins C and E, coenzyme Q-10, glutathione, L-cysteine and N-acetylcysteine; and (6) local anesthetics, to name a few.

In one embodiment, umbilical cord tissue-derived cells are administered as undifferentiated cells, i.e., as cultured in Growth Medium. Alternatively, umbilical cord tissue-derived cells may be administered following exposure in culture to conditions that stimulate differentiation toward a desired skeletal muscle, vascular smooth muscle, pericyte, or vascular endothelium phenotype.

The cells of the invention may be surgically implanted, injected, delivered (e.g., by way of a catheter, syringe, shunt, stent, microcatheter, or pump), or otherwise administered directly or indirectly to the site of ischemic injury, damage, or distress. Routes of administration of the cells of the invention or compositions thereof include, but are not limited to, intravenous, intramuscular, subcutaneous, intranasal, intrathecal, intracisternal, or via syringes with needles or catheters with or without pump devices.

When cells are administered in semi-solid or solid devices, surgical implantation into a precise location in the body is typically a suitable means of administration. Liquid or fluid pharmaceutical compositions, however, may be administered through the blood, or directly into affected muscle tissue (e.g., throughout a diffusely affected area, such as would be the case for diffuse ischemic injury). The migration of the umbilical cord tissue-derived cells can be guided by chemical signals, growth factors, or calpains.

The umbilical cord tissue-derived cells or compositions and/or matrices comprising the umbilical cord tissue-derived cells may be delivered to the site via a micro catheter, intra-catheterization, or via a mini-pump. The vehicle excipient or carrier can be any of those known to be pharmaceutically acceptable for administration to a patient, particularly locally at the site at which cellular differentiation is to be induced. Examples include liquid media, for example, Dulbeccos Modified Eagle's Medium (DMEM), sterile saline, sterile phosphate buffered saline, Leibovitz's medium (L15, Invitrogen, Carlsbad, Calif.), dextrose in sterile water, and any other physiologically acceptable liquid.

Other embodiments encompass methods of treating peripheral ischemic injury or damage by administering therapeutic compositions comprising a pharmaceutically acceptable carrier and umbilical cord tissue-derived cell cellular components (e.g., cell lysates or components thereof) or products (e.g., trophic and other biological factors produced naturally by umbilical cord tissue-derived cells or through genetic modification, conditioned medium from umbilical cord tissue-derived cell culture), or umbilical cord tissue-derived cell growth medium or products purified from growth medium. In preferred embodiments, the biological factors are FGF and HGF. These methods may further comprise administering other active agents, such as growth factors, angiogenic factors or myoregenerative or myoprotective drugs as known in the art.

Dosage forms and regimes for administering umbilical cord tissue-derived cells or any of the other therapeutic or pharmaceutical compositions described herein are developed in accordance with good medical practice, taking into account the condition of the individual patient, e.g., nature and extent of the injury or damage from the peripheral ischemic event, age, sex, body weight and general medical condition, and other factors known to medical practitioners. Thus, the effective amount of a pharmaceutical composition to be administered to a patient is determined by these considerations as known in the art.

Umbilical cord tissue-derived cells have been shown not to stimulate allogeneic PBMCs in a mixed lymphocyte reaction. Accordingly, transplantation with allogeneic, or even xenogeneic, umbilical cord tissue-derived cells may be tolerated in some instances. In some embodiments, the umbilical cord tissue-derived cells themselves provide an immunosuppressant effect, thereby preventing host rejection of the transplanted umbilical cord tissue-derived cells. In such instances, pharmacological immunosuppression during cell therapy may not be necessary.

However, in other instances it may be desirable or appropriate to pharmacologically immunosuppress a patient prior to initiating cell therapy. This may be accomplished through the use of systemic or local immunosuppressive agents, or it may be accomplished by delivering the cells in an encapsulated device, as described above. These and other means for reducing or eliminating an immune response to the transplanted cells are known in the art. As an alternative, umbilical cord tissue-derived cells may be genetically modified to reduce their immunogenicity, as mentioned above.

Survival of transplanted umbilical cord tissue-derived cells in a living patient can be determined through the use of a variety of scanning techniques, e.g., computerized axial tomography (CAT or CT) scan, magnetic resonance imaging (MRI) or positron emission tomography (PET) scans. Determination of transplant survival can also be done post mortem by removing the skeletal muscle or vascular tissue, and examining it visually or through a microscope. Alternatively, cells can be treated with stains that are specific for skeletal muscle cells, vascular smooth muscle cells, pericytes, or vascular endothelial cells. Transplanted cells can also be identified by prior incorporation of tracer dyes such as rhodamine- or fluorescein-labeled microspheres, fast blue, ferric microparticles, bisbenzamide or genetically introduced reporter gene products, such as beta-galactosidase or beta-glucuronidase.

In another aspect, the invention provides kits that utilize the umbilical cord tissue-derived cells, umbilical cord tissue-derived cell populations, components and products of umbilical cord tissue-derived cells in various methods for stimulating and/or supporting angiogenesis, for improving blood flow, for regenerating, repairing, and improving skeletal muscle injured or damaged by a peripheral ischemic event, as described above. Where used for treatment of damage or injury caused by an ischemic event or other scheduled treatment, the kits may include one or more cell populations, including at least umbilical cord tissue-derived cells and a pharmaceutically acceptable carrier (liquid, semi-solid or solid). The kits also optionally may include a means of administering the cells, for example by injection. The kits further may include instructions for use of the cells. Kits prepared for field hospital use, such as for military use, may include full-procedure supplies including tissue scaffolds, surgical sutures, and the like, where the cells are to be used in conjunction with repair of acute injuries. Kits for assays and in vitro methods as described herein may contain one or more of (1) umbilical cord tissue-derived cells or components or products of umbilical cord tissue-derived cells, (2) reagents for practicing the in vitro method, (3) other cells or cell populations, as appropriate, and (4) instructions for conducting the in vitro method.

The following examples describe the invention in greater detail. These examples are intended to further illustrate, not to limit, aspects of the invention described herein.

EXAMPLE 1

Efficacy of Umbilicus-Derived Cells in the Murine Hindlimb Peripheral Ischemia Model Materials and Methods Umbilical Cell Culture and Isolation. Umbilicus-derived cells (UDCs) were prepared as described in U.S. Patent Publications 2005/0058631 or 2005/0054098. Cells were cultured to passage 10 or 11 (approximately 20 to 25 population doublings) and then cryogenically preserved.

Ischemia Model Treatment Groups:

| Group | |
|---|---|
| 1 | PBS, negative control |
| 2 | Expression plasmid for vascular endothelial growth factor(pVEGF), positive control |
| 3 | cell line #1 cells, $5 \times 10^5$ cells total |
| 4 | cell line #1 cells, $1 \times 10^6$ cells total |
| 5 | cell line #2 cells, $1 \times 10^6$ cells total |
| 6 | cell line #1 cells, cultured, $1 \times 10^6$ cells total | cell line 1: U120304 p10,
cell line 2: U072804A p11

Sample Preparation for Injection.

Cells were thawed immediately before injection (groups 3 to 5), or were cultured for 24 to 30 hours (group 6). Cells were counted and viability was determined by trypan blue staining and counting on a hemocytometer. The entire dose of cells or plasmid (100 µg) was resuspended in 100 µl of PBS and loaded into a 300 µl tuberculin syringe with 27 gauge needle for injection into the mice.

Surgery.

On day 0, acute hindlimb ischemia was surgically induced in athymic, nude mice by unilateral ligation and excision of the left iliofemerol artery. Mice were partitioned into 6 groups of at least n=8 for treatment with UDCs or controls. Mice were randomly assigned to treatment groups for groups 1 to 5. Because group 6 was added late in the study, randomization did not occur. In addition, scheduling conflicts precluded performing microCT/PET concurrently with the original study. This analysis was performed on a group of 8 additional animals (4 control and 4 cultured cell 1) enrolled after the completion of the 21 day study.

Cell Injections.

One day after surgery, mice were anesthetized for laser Doppler imaging analysis of the plantar region. While mice were still under anesthesia, cells were injected at 5 sites in the left (ischemic) limb: (1) 20 µl into the tibialis anterior; (2) 2×20 µl into gastrocnemius; and (3) 2×20 µl into rectus femoris of quadriceps bundle.

Analyses.

Laser Doppler imaging was performed at days 1, 4, 8, 14 and 21. At 21 days, mice were sacrificed and tibialis anterior (TA), gastrocnemius and quadriceps muscles were excised and cryofixed for thin sectioning and immunhistochemical staining with CD31 antibody. MicroCT/PET analysis using fluoromethane gas to determine perfusion status of muscles was performed at 8 days. These mice were sacrificed immediately after and hindlimb muscles were processed for CD31 immunohistochemistry on cryofixed thin sections.

Exclusion Criteria.

Mice exhibiting severe toe necrosis at day 1 following surgery were excluded from the study before injections. Mice were also excluded at any time in the study due to severe necrosis (e.g., total necrosis of the foot) or if they experienced severe weight loss or otherwise exhibited signs of extreme pain.

Results

The goal of these experiments was to determine if UDCs protect tissues from injury in a rodent hindlimb ischemia model. This model was performed by creating an injury in the femoral blood flow and injecting cells in the area approximately 24 hours after the injury. The results were evaluated by estimating perfusion of the limbs of these animals and comparing this to the contralateral limb that was not injured. The tissues were also collected from these animals at the end of the study to evaluate the vasculature and injury in the animals. This study was also performed with human cells in nude mice to avoid xenogenic rejection of the implanted cells.

Results presented in FIG. 1 show that the UDCs conferred a benefit on the mice, as there was improved perfusion in the animals treated with the cultured cells at Day 4 and 8, while blood flow was also improved in the animals treated with the 120304 cells thawed immediately before injection at Day 8. The cells 072804A did not show a benefit at any time point, suggesting a difference between these two lots of cells. Generally the animals showed improvement over time indicating that this strain of animals has some degree of native repair capability. These animals were also relatively young which may be a factor in their innate regenerative capabilities.

Figure 2A:
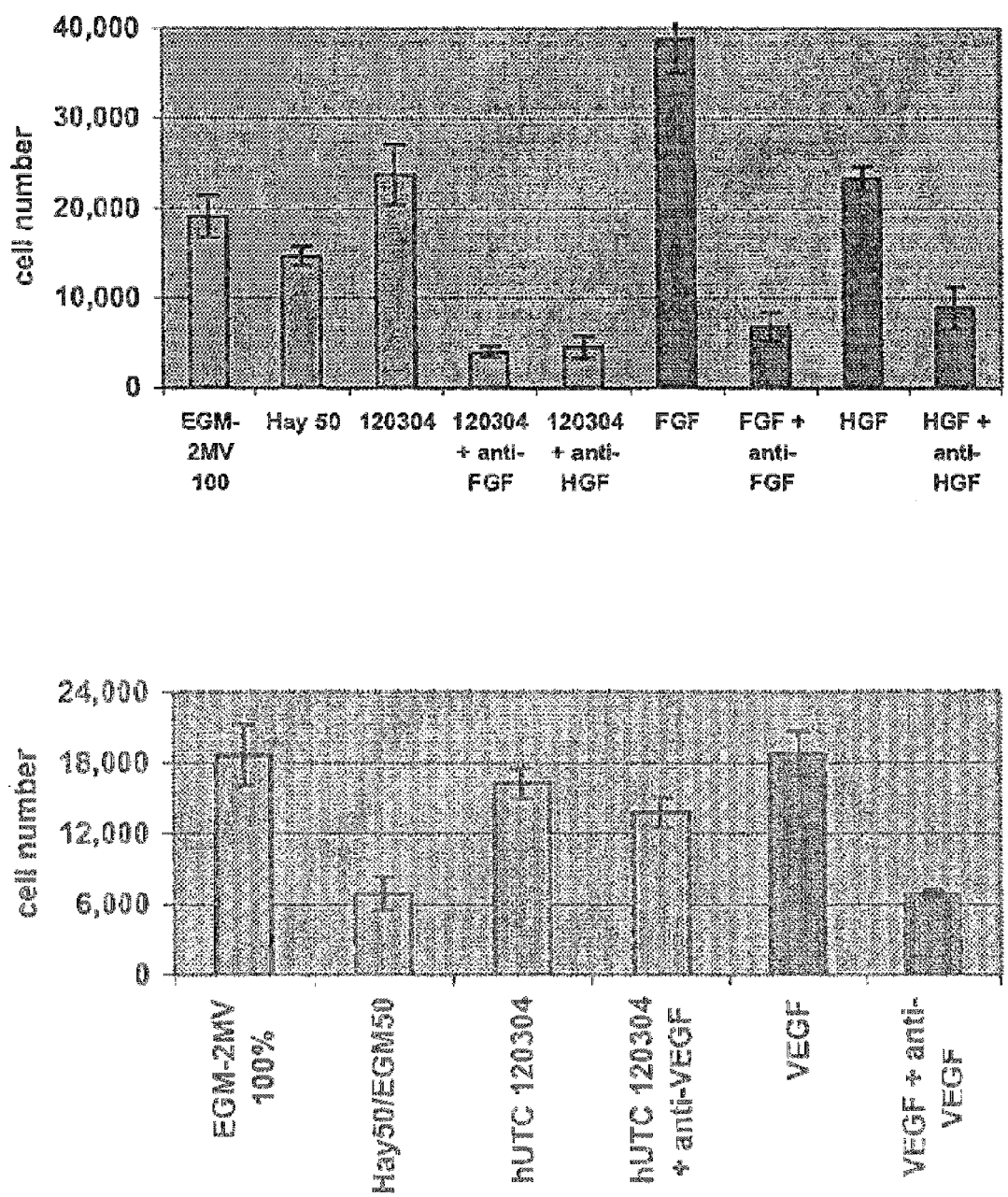
FIG. 2 shows the effect of hUTC lot#120304 and neutralizing antibodies on the proliferation of endothelial cells. HUVECs or HCAECs were seeded onto the bottom of a 24-well tissue culture dish at a density of 5000 cells/cm$^2$ (10,000 cells/well) and hUTC lot#120304 inside transwell inserts at a density of 5000 cells/cm$^2$ (1,650 cells/insert) in co-culture media (Hayflick 50%+EGM-2MV 50%). Neutralizing antibodies to FGF (7 µg/ml), HGF (1 µg/ml), or VEGF (1 µg/ml) were also added at this time. After 7 days of co-culture, cells were harvested and counted using a Guava® instrument. Endothelial cells were also maintained in EGM-2MV media as positive control. Cells treated with growth factor alone and growth factor plus neutralizing antibodies are shown. A and B, HUVECs. C and D, HCAECs.
Figure 2B:
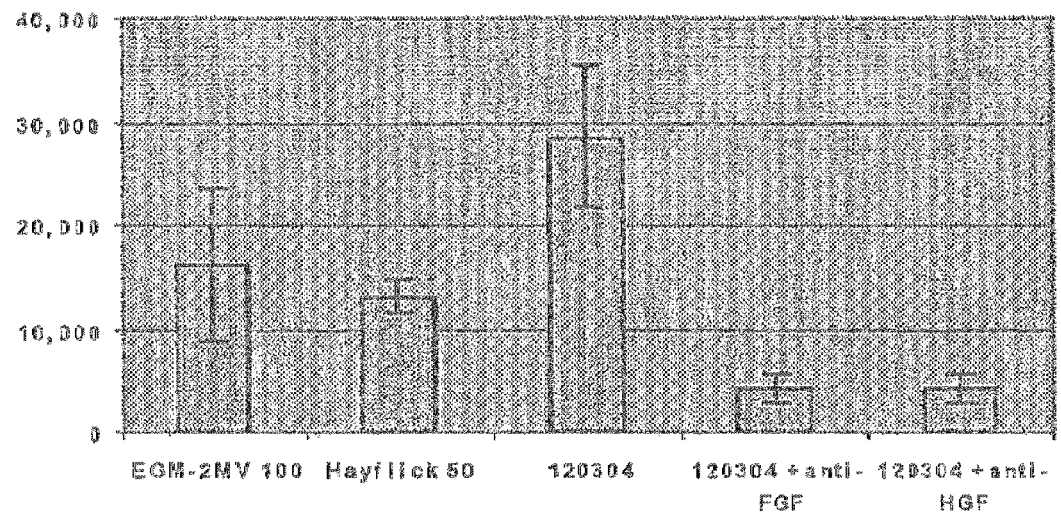
Figure 2B:
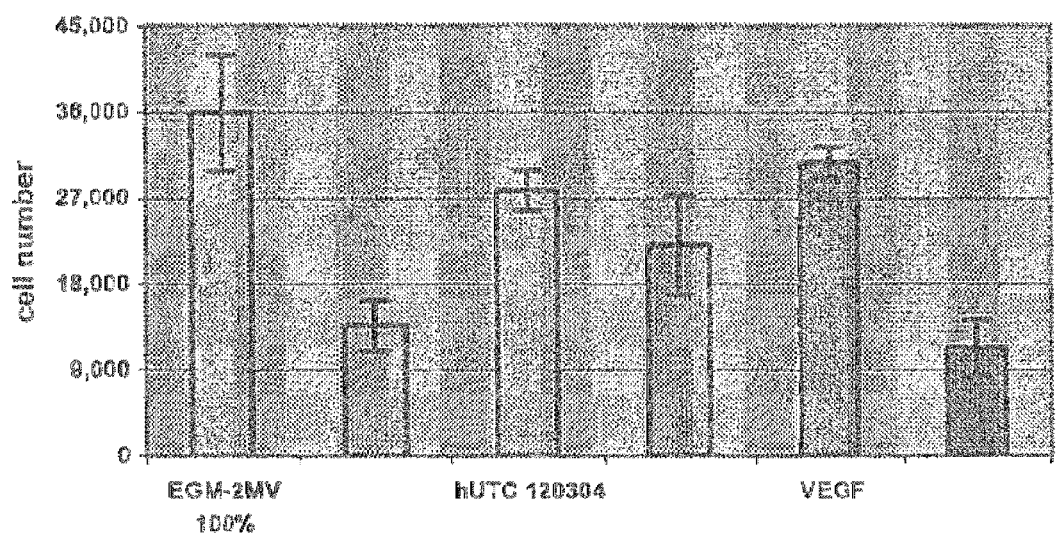

The TA muscles were collected at the end of the study, and sections were probed with an anti CD31 antibody to detect vascular endothelial cells. Representative results are shown in FIG. 2. The results show that the PBS control animals presented gross necrosis and limited vasculature in the ischemic limb, (for example mouse #26 & #43) whereas the UDC-treated limbs showed higher relative levels of CD31 staining and reduced levels of necrosis. The results also suggest that the animals treated with cultured UDCs showed improved vasculature as compared to controls—(PBS control and in some cases, the normal (uninjured) limb). Increased CD 31 staining was observed in the ischemic but treated limb as compared to the normal limb. The animals treated with VEGF plasmid and Umb072804A showed similar results as PBS control.

SUMMARY

These results provide evidence that umbilical cord-derived cells can be effective to improve blood flow and to reduce tissue necrosis in a rodent hind limb ischemia model. The study included two different lots of umbilical cells that were thawed immediately before injection, and the results suggested differences might exist between the lots. The cells that appeared to have some activity were also cultured for approximately 48 hours before injection and included in another treatment group. These cells appeared to be the most effective and this suggests that culturing changes the activity profile of the cells. The histology results also provide evidence that treatment can provide protective effects. The results do not provide sufficient information with respect to the mechanism by which the UDCs exert their effects. Without intending to be bound to any particular theory or mechanism of action, it is believed that the cells may exert their effect by stimulating the growth of new blood vessels or protecting the muscle tissue from the progression of the damage, for example, by protection from apoptosis or recruitment of endogenous active agents. Additional studies are necessary to investigate the precise mechanism of action.

REFERENCES

1) Rehman, J. et al. (2004) *Circulation* 109:1292-1298.

EXAMPLE 2

Endothelial Network Formation Assay

Angiogenesis, or the formation of new vasculature, is necessary for the growth of new tissue. Induction of angiogenesis is an important therapeutic goal in many pathological conditions. To identify potential angiogenic activity of the umbilical cord tissue-derived cells in vitro assays, a well-established method of seeding endothelial cells onto a culture plate coated with a biological cell culture substrate under the tradename MATRIGEL (BD Discovery Labware, Bedford, Mass.), a basement membrane extract (Nicosia and Ottinetti (1990) *In Vitro Cell Dev. Biol.* 26(2):119-28) was followed. Treating endothelial cells on MATRIGEL (BD Discovery Labware, Bedford, Mass.) with angiogenic factors will stimulate the cells to form a network that is similar to capillaries. This is a common in vitro assay for testing stimulators and inhibitors of blood vessel formation (Ito et al. (1996) *Int. J. Cancer* 67(1):148-52). The experiments made use of a co-culture system with the umbilical cord tissue-derived cells seeded onto culture well inserts. These permeable inserts allow for the passive exchange of media components between the endothelial and the umbilical cord tissue-derived cell culture media.

Methods & Materials
Cell Culture
  Umbilical and Placental Tissue-Derived Cells.
  Human umbilical cords and placenta were received and cells were isolated as previously described (see Example 1). Cells were cultured in Growth medium (Dulbecco's Modified Essential Media (DMEM; Invitrogen, Carlsbad, Calif.), 15% (v/v) fetal bovine serum (Hyclone, Logan Utah)), 100 Units/milliliter penicillin, 100 microgram/milliliter streptomycin (Invitrogen), 0.001% (v/v) 2-mercaptoethanol (Sigma, St. Louis, Mo.)) on gelatin-coated tissue culture plastic flasks. The cultures were incubated at 37° C. with 5% $CO_2$. Cells used for experiments were between passages 4 and 12.
  Actively growing cells were trypsinized, counted, and seeded onto COSTAR TRANSWELL 6.5 millimeter diameter tissue culture inserts (Corning, Corning, N.Y.) at 15,000 cells per insert. Cells were cultured on the inserts for 48 to 72 hours in Growth medium at 37° C. under standard growth conditions.
  Human Mesenchymal Stem Cells (hMSC).
  hMSCs were purchased from Cambrex (Walkersville, Md.) and cultured in MSCGM (Cambrex). The cultures were incubated under standard growth conditions.
  Actively growing MSCs were trypsinized and counted and seeded onto COSTAR TRANSWELL 6.5 millimeter diameter tissue culture inserts (Corning, Corning, N.Y.) at 15,000 cells per insert. Cells were cultured on the inserts for 48-72 hours in Growth medium under standard growth conditions.
  Human Umbilical Vein Endothelial Cells (HUVEC).
  HUVEC were obtained from Cambrex (Walkersville, Md.). Cells were grown in separate cultures in either EBM or EGM endothelial cell media (Cambrex). Cells were grown on standard tissue-cultured plastic under standard growth conditions. Cells used in the assay were between passages 4 and 10.
  Human Coronary Artery Endothelial Cells (HCAEC).
  HCAEC were purchased from Cambrex Incorporated (Walkersville, Md.). These cells were also maintained in separate cultures in either the EBM or EGM media formulations. Cells were grown on standard tissue cultured plastic under standard growth conditions. Cells used for experiments were between passages 4 and 8.
  Endothelial Network Formation (MATRIGEL) Assays.
  Culture plates were coated with MATRIGEL (BD Discovery Labware, Bedford, Mass.) according to manufacturer's specifications. Briefly, MATRIGEL (BD Discovery Labware, Bedford, Mass.) was thawed at 4° C. and approximately 250 microliters were aliquoted and distributed evenly onto each well of a chilled 24-well culture plate (Corning). The plate was then incubated at 37° C. for 30 minutes to allow the material to solidify. Actively growing endothelial cell cultures were trypsinized and counted. Cells were washed twice in Growth medium with 2% FBS by centrifugation, resuspension, and aspiration of the supernatant. Cells were seeded onto the coated wells at 20,000 cells per well in approximately 0.5 milliliter Growth medium with 2% (v/v) FBS. Cells were then incubated for approximately 30 minutes to allow cells to settle.
  Endothelial cell cultures were then treated with either 10 nanomolar human bFGF (Peprotech, Rocky Hill, N.J.) or 10 nanomolar human VEGF (Peprotech, Rocky Hill, N.J.) to serve as a positive control for endothelial cell response. Transwell inserts seeded with umbilical cord tissue-derived cells were added to appropriate wells with Growth medium with 2% FBS in the insert chamber. Cultures were incubated at 37° C. with 5% $CO_2$ for approximately 24 hours. The well plate was removed from the incubator, and images of the endothelial cell cultures were collected with an Olympus inverted microscope (Olympus, Melville, N.Y.).
Results
  In a co-culture system with placenta-derived cells or with umbilical cord-derived cells, HUVEC form cell networks (data not shown). HUVEC cells form limited cell networks in co-culture experiments with hMSCs and with 10 nanomolar bFGF (not shown). HUVEC cells without any treatment showed very little or no network formation (data not shown). These results suggest that the umbilical cord tissue-derived cells release angiogenic factors that stimulate the HUVEC.
  In a co-culture system with placenta-derived cells or with umbilical cord-derived cells, CAECs form cell networks (data not shown).
  Table 2-1 shows levels of known angiogenic factors released by the placental- and umbilical cord tissue-derived cells in Growth medium. Placental- and umbilical cord tissue-derived cells were seeded onto inserts as described above. The cells were cultured at 37° C. in atmospheric oxygen for 48 hours on the inserts and then switched to a 2% FBS media and returned at 37° C. for 24 hours. Media was removed, immediately frozen and stored at −80° C., and analyzed by the SearchLight multiplex ELISA assay (Pierce Chemical Company, Rockford, Ill.). Results shown are the averages of duplicate measurements. The results show that the umbilical- and placental-derived cells do not release detectable levels of platelet-derived growth factor-bb (PDGF-bb) or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

TABLE 2-1

Potential angiogenic factors released from umbilical and placental-derived cells.

| | TIMP1 (pg/ml) | ANG2 (pg/ml) | PDGFBB (pg/ml) | TPO (pg/ml) | KGF (pg/ml) | HGF (pg/ml) | FGF (pg/ml) | VEGF (pg/ml) | HBEGF (pg/ml) |
|---|---|---|---|---|---|---|---|---|---|
| Plac (P4) | 91655.3 | 175.5 | <2.0 | 275.5 | 3.0 | 58.3 | 7.5 | 644.6 | <1.2 |
| Plac (P11) | 1592832.4 | 28.1 | <2.0 | 1273.1 | 193.3 | 5960.3 | 34.8 | 12361.1 | 1.7 |
| Umb cord (P4) | 81831.7 | <9.8 | <2.0 | 365.9 | 14.1 | 200.2 | 5.8 | <4.0 | <1.2 |
| Media alone | <9.8 | 25.1 | <2.0 | <6.4 | <2.0 | <3.2 | <5.4 | <4.0 | <1.2 |

Umbilical- and placental-derived cells were cultured in 24 hours in media with 2% FBS in atmospheric oxygen. Media was removed and assayed by the SearchLight multiplex ELISA assay (Pierce). Results are the means of a duplicate analysis. Values are concentrations in the media reported in picograms per milliliter of culture media. Plac: placenta derived cells; Umb cord: umbilical cord derived cells.

Table 2-2 shows levels of known angiogenic factors released by the umbilical- and placental-derived cells. Umbilical- and placental-derived cells were seeded onto inserts as described above. The cells were cultured in Growth medium at 5% oxygen for 48 hours on the inserts and then switched to a 2% FBS medium and returned to 5% $O_2$ incubation for 24 hours. Media was removed, immediately frozen, and stored at −80° C., and analyzed by the SearchLight multiplex ELISA assay (Pierce Chemical Company, Rockford, Ill.). Results shown are the averages of duplicate measurements. The results show that the umbilical- and placental-derived cells do not release detectable levels of platelet-derived growth factor-bb (PDGF-BB) or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

Umbilical- and placental-derived cells were cultured in 24 hours in media with 2% FBS in 5% oxygen. Media was removed and assayed by the SearchLight multiplex ELISA assay (Pierce). Results are the means of a duplicate analysis. Values are concentrations in the media reported in picograms per milliter of culture media. Plac: placenta derived cells; Umb cord: umbilical cord derived cells.

SUMMARY

The results show that umbilical- and placental-derived cells can stimulate both human umbilical vein and coronary artery endothelial cells to form networks in an in vitro MATRIGEL (BD Discovery Labware, Bedford, Mass.) assay. This effect is similar to that seen with known angiogenic factors in this assay system. These results suggest that the umbilical- and placental-derived cells are useful for stimulating angiogenesis in vivo.

EXAMPLE 3

Effect if hUTCs on the In Vitro Proliferation and Migration of Endothelial Cells Studies were undertaken to determine the effects of human umbilical tissue-derived cells (hUTCs) on the proliferation and migration of endothelial cells in vitro. These effects were examined by co-culturing hUTCs and endothelial cells and by incubating cultures of human umbilical vein endothelial cells (HUVECs) with hUTC lysates. The results presented here show that hUTCs induce increases in proliferation and migration of endothelial cells. Furthermore, the data suggest that these effects are mediated, in part, by fibroblast growth factor (FGF) and hepatocyte growth factor (HGF).
Materials and Methods
Cell Culture
Cryopreserved human umbilical tissue-derived cells (hUTCs) lot#120304 were thawed at passage 8-9 and seeded onto gelatin-coated flasks and cultured in Hayflick growth media (DMEM—low glucose (Gibco, catalog number11885-084), 15% v/v fetal bovine serum (FBS, Hyclone, catalog number SH30070.03), 0.001% v/v beta-mercaptoethanol

TABLE 2-2

Potential angiogenic factors released from umbilical- and placental-derived cells.

| | TIMP1 (pg/ml) | ANG2 (pg/ml) | PDGF-BB (pg/ml) | TPO (pg/ml) | KGF (pg/ml) | HGF (pg/ml) | FGF (pg/ml) | VEGF (pg/ml) | HBEGF (pg/ml) |
|---|---|---|---|---|---|---|---|---|---|
| Plac (P4) | 72972.5 | 253.6 | <2.0 | 743.1 | 2.5 | 30.2 | 15.1 | 1495.1 | <1.2 |
| Plac (P11) | 458023.1 | 55.1 | <2.0 | 2562.2 | 114.2 | 2138.0 | 295.1 | 7521.3 | 1.8 |
| Umb cord (P4) | 50244.7 | <9.8 | <2.0 | 403.3 | 10.7 | 156.8 | 5.7 | <4.0 | <1.2 |
| Media alone | <9.8 | 25.1 | <2.0 | <6.4 | <2.0 | <3.2 | <5.4 | <4.0 | <1.2 |

(Sigma, catalog number M7154), and 50 U/ml penicillin and 50 micrograms/ml streptomycin (Gibco, catalog number 3810-74-0)). For studies detailed here, cells used were at passage 10 or 11. Human umbilical vein endothelial cells (HUVECs, catalog number C2517A), human coronary artery endothelial cells (HCAECs, catalog number CC2585), and human iliac artery endothelial cells (HIAECs, catalog number CC2545) were obtained from Cambrex and were cultured in endothelial growth medium (EGM-2MV, catalog number 3202) according to manufacturer's recommendations. Human mesenchymal stem cells (MSCs, catalog number PT-2501) were also purchased from Cambrex and were maintained in mesenchymal stem cell growth medium (MSCGM, catalog number PT-3001) according to manufacturer's recommendations. Human dermal fibroblasts (CCD9) were from ATCC and were maintained in DMEM/F12 media containing 10% FBS and 1 U/ml penicillin-streptomycin.

For routine passage, cells were washed once with phosphate buffered saline (PBS, Invitrogen, catalog number 14190) and detached by trypsinization (0.25% trypsin-EDTA, Invitrogen, catalog number 25200-056). Cells were counted using a Guava® instrument (Guava Technologies, Hayward, Calif.) and seeded at a density of 5000 cells/cm². Cells were routinely passaged every 3-4 days.

Growth Factors and Antibodies

Recombinant human basic fibroblast growth factor (bFGF, catalog number 100-18B) and recombinant human hepatocyte growth factor (HGF, catalog number 100-39) were from Peprotech and recombinant human vascular endothelial growth factor (VEGF, catalog number 293-VE) was from R and D Systems. Antibodies to bFGF (catalog number ab11937), HGF (catalog number ab10678), and VEGF (catalog number ab9570) were purchased from Abcam (Cambridge, Mass.).

Preparation of Cell Lysate

Cell lysates were prepared from frozen hUTC lot#120304 cell pellets from previous grow-ups. Briefly, hUTC lot#120304 were cultured for 4 days, harvested by trypsinization, and pelleted by centrifugation. Cells were then washed with PBS 3 times and resuspended in PBS at 1×10⁷ cells/ml. Aliquots of 1 ml suspensions were placed into 1.5 ml sterile siliconized microcentrifuge tubes and centrifuged at 300 rcf for 5 minutes. PBS was aspirated and cell pellets stored at −80° C. until use.

To prepare cell lysates, tubes containing cell pellets were immersed in liquid nitrogen (LN2) for 60 seconds and then immediately immersed in a 37° C. water bath for 60 seconds or until thawed but not longer than 3 minutes. This step was repeated 3 times. Following this step, the freeze-thawed samples were centrifuged at 13000 rcf at 4° C. for 10 minutes and then placed on ice. The supernatant was carefully removed and transferred to a fresh sterile siliconized 1.5 ml tube. The centrifugation step was repeated 3 times and the resulting supernatant pooled. Protein concentration was determined using the microassay protocol of the Quickstart Bradford protein assay kit (Bio-rad, catalog number 500-0201).

Measurement of Cell Proliferation

Cells were harvested and plated directly into the indicated media formulation at a concentration of 5000 cells/cm². For co-culture experiments, 24-well transwells (Corning catalog number 3413) were used with endothelial cells plated on the bottom of the well (10,000 cells/well) and hUTCs, MSCs, or fibroblasts plated inside the transwell inserts (1650 cells/transwell inserts). At the indicated time periods, inserts containing hUTCS, MSCs, or fibroblasts were removed and discarded. Endothelial cells were harvested by adding 90 μl of trypsin to each well. Cells were released by pipetting up and down and then transferred to a clean 96-well plate. Trypsin was inhibited by the addition of 90 μl of media. Cells were stained by addition of 20 μl of staining solution (18 μl of media+1 μl Guava Viacount Flex Reagent+1 μl of DMSO) and quantitated using a Guava® instrument (Guava Technologies, Hayward, Calif.).

For studies on the effect of hUTC lot#120304 cell lysate on the proliferation of HUVECs, HUVECs were seeded onto 24-well tissue culture dishes at a density of 10,000 cells/well in EGM-2MV media for 8 hours. Cells were then serum-starved by overnight incubation in 0.5 ml of EGM-2MV media containing 0.5% FBS and without growth factors. Afterwards, FBS, freshly prepared hUTC lot#120304 cell lysate containing 62.5 μg or 125 μg of protein, and neutralizing antibodies to FGF (7 μg/ml) or HGF (1 μg/ml) were added. After 4 days of culture, cells were harvested and counted using a Guava® instrument.

For studies on the potential mechanisms of hUTC-mediated increase in endothelial cell proliferation, neutralizing antibodies to FGF (7 ng/ml), HGF (1 ng/ml), and VEGF (1 ng/ml) were included in co-cultures of HUVECs and HCAECs with hUTCs. The antibodies were added to the cell culture media when the cells were initially plated. After 7 days of co-culture, cells were harvested and counted using a Guava® instrument.

Assessment of Cell Migration

For measurement of cell migration, a 6-well transwell (Corning catalog number 3428) set-up was used. Cells were seeded directly into the indicated media formulation at a density of 5000 cells/cm². Endothelial cells were seeded inside the transwell inserts (23,000 cells/transwell insert) and hUTC lot#120304 or MSCs plated onto the bottom of the well (48,000 cells/well). Migration was assessed after 7 days of co-culture by counting the number of cells on the underside of the transwell. Briefly, transwells were transferred to a clean well and washed once with PBS. Cells from the underside of the well were harvested by adding trypsin to the bottom of the well. Trypsin was inhibited by the addition of complete growth media and cells collected by centrifugation. Cells were then resuspended in 25 μl of media and 20 μl of this used to obtain cell counts using a Guava® instrument.

For studies on the potential mechanisms of hUTC-mediated increase in endothelial cell migration, neutralizing antibodies to FGF (7 ng/ml) and HGF (1 ng/ml) were included in co-cultures of HUVECs and HCAECs with hUTC lot#120304. The antibodies were added to the cell culture media when the cells were initially plated. After 7 days of co-culture, cells that were on the underside of the transwell insert were harvested and counted using a Guava® instrument.

Results

Effect of hUTCs on Proliferation of Endothelial Cells

A co-culture system was utilized to study the effects of hUTCs on the proliferation of endothelial cells. This was performed using a transwell set-up with endothelial cells plated on the bottom of a 24-well tissue culture dish and hUTCs plated inside the transwell inserts. In these experiments, two different media formulations were used (media composition detailed in Materials and Methods): (1) Hayflick 80%+EGM-2MV 20% (H80) or (2) Hayflick 50%+EGM-2MV 50% (H50). After 6 or 7 days of co-culture, the transwell inserts were removed, endothelial cells harvested by trypsinization, and counted using the Guava® instrument.

Figure 1B:
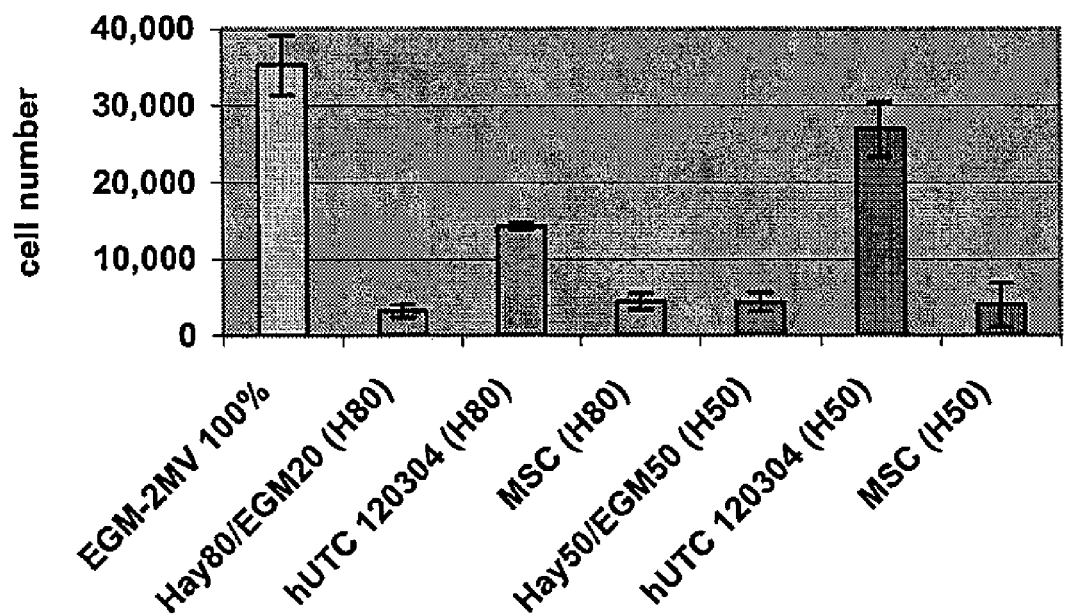
Figure 1C:
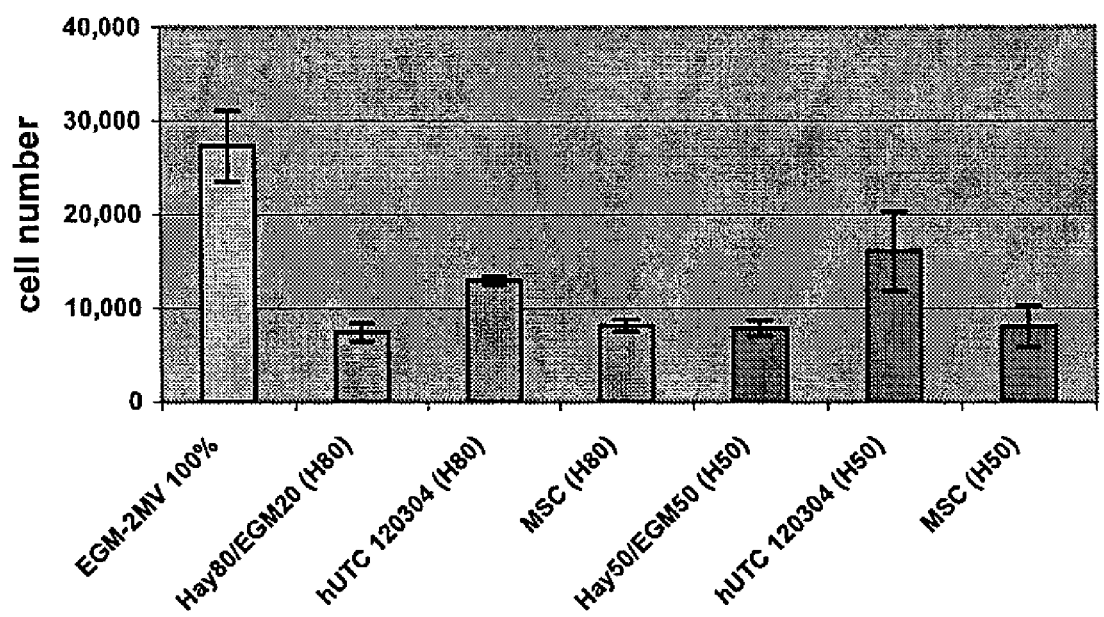

The effect of hUTC lot#120304 on the proliferation of endothelial cells cultured in H80 compared with H50 is shown in FIG. 1. The proliferation of HUVECs maintained in H50 was higher than those kept in H80 (FIG. 1A) while HCAECs and HIAECs exhibited similar growth in these co-culture media formulations (FIG. 1B and FIG. 1C). In both media formulations, co-culture of endothelial cells with hUTC lot#120304 resulted in significant increases in cell number after 7 days. All subsequent co-culture studies of hUTCs and endothelial cells were performed in the Hayflick 50%+EGM-2MV 50% (H50) media formulation.

MSCs and fibroblasts were also tested in co-cultures with endothelial cells to determine whether other cell types have the ability to influence the proliferation of endothelial cells. As shown in FIG. 1A, there was no difference in the proliferation of HUVECs in co-culture media (H50 or H80) and those that were co-cultured with MSCs or with fibroblasts. The same was true of HCAECs (FIG. 1B) and HIAECs (FIG. 1C) where co-culture with hUTC lot#120304 resulted in increased cell proliferation while no differences can be observed between cells in co-culture media (H50 or H80) and those that were co-cultured with MSCs.

To investigate the potential mechanisms of hUTC-mediated increase in endothelial cell proliferation, neutralizing antibodies to FGF (7 mg/ml), HGF (1 mg/ml), and VEGF (1 μg/ml) were included in co-cultures of HUVECs and HCAECs with hUTCs. Results in FIGS. 2A to 2D show that in both HUVECs and HCAECs the addition of neutralizing antibodies to FGF and HGF reduced the increase in cell number induced by hUTC lot#120304. At the concentrations that were used for these studies, these neutralizing antibodies blocked proliferation of HUVECs induced by the growth factors (FIGS. 2A and 2B). It is interesting to note that a neutralizing antibody to VEGF did not have a significant effect on the cell proliferation induced by co-culture of both HUVECs (FIGS. 2A and 2B) and HCAECs (FIGS. 2C and 2D) with hUTC lot#120304. In separate studies, the proliferation of hUTC lot#120304 was not affected by the addition of neutralizing antibodies to FGF and VEGF to the culture media (data not shown).

Effect of hUTC Lot#120304 Cell Lysate on Proliferation of HUVECs

Studies were also conducted to determine the effect of cell lysate on the proliferation of HUVECs. HUVECs were seeded onto 24-well plates in EGM-2MV media for 8 h at a density of 5000 cells/cm$^2$. The cells were then serum-starved by an overnight incubation in 0.5 ml of EGM-2MV media containing 0.5% fetal bovine serum (FBS) and without growth factors. Following the incubation, varying concentrations of freshly prepared hUTC lot#120304 cell lysate were added. In some instances, FGF, HGF, and neutralizing antibodies were also included. After 4 days of culture, HUVECs were harvested and counted using a Guava® instrument.

Figure 3:
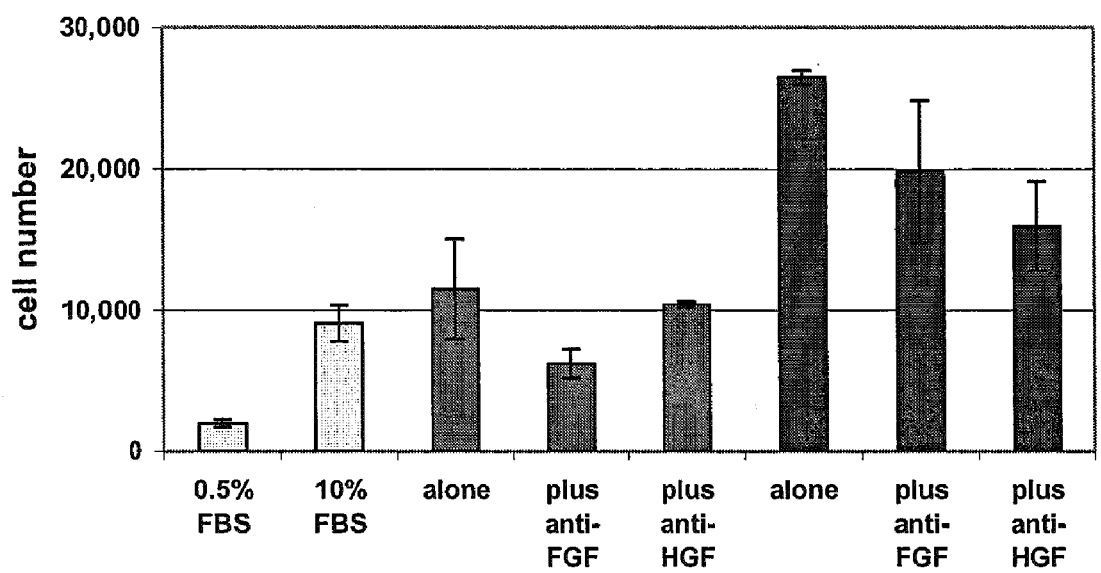
FIG. 3 shows the effect of hUTC lot#120304 cell lysate and neutralizing antibodies on proliferation of HUVECs. HUVECs were seeded onto the bottom of a 24-well tissue culture dish at a density of 5000 cells/cm$^2$ (10,000 cells/well) in EGM-2MV media for 8 h. Cells were then serum-starved by overnight incubation in 0.5 ml of EGM-2MV media containing 0.5% FBS and without growth factors. Afterwards, FBS, freshly prepared hUTC lot#120304 cell lysates, and neutralizing antibodies to FGF (7 µg/ml) or HGF (1 µg/ml) were added. After 4 days of culture, cells were harvested and counted using a Guava® instrument. Light grey bars, media controls. Medium grey bars, HUVECs incubated with lysate containing 62.5 µg of protein. Dark grey bars, HUVECs incubated with lysate containing 125 µg of protein.

FIG. 3 shows that the addition of cell lysates led to an increase in HUVECs cell number compared to cells kept in low serum (0.5% FBS) and the increase in cell number was proportional to the amount of added cell lysate. The lower concentration of cell lysate used (62.5 mg/ml) resulted in a cell number comparable to cells incubated in optimal media condition (10% FBS). Furthermore, the addition of a neutralizing antibody to either FGF or HGF moderated the increase in cell number induced by the 2 different concentrations of cell lysate. These results are consistent with the results obtained in co-cultures of HUVECs with hUTC lot#120304.

Effect of hUTCs on Migration of Endothelial Cells

Figure 4:
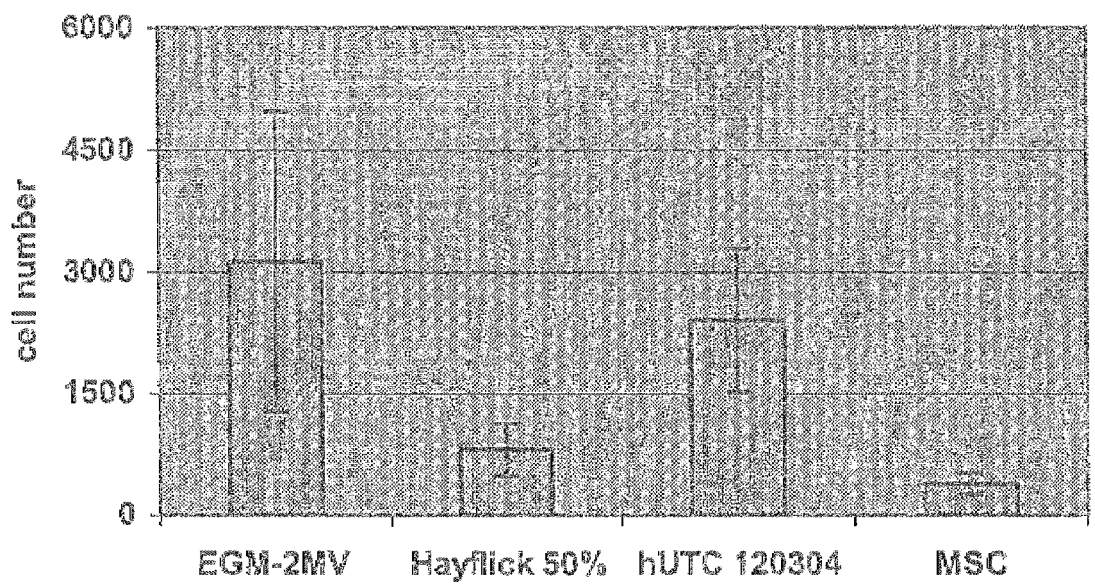
FIG. 4 shows the effect of hUTCs and MSCs on the migration of endothelial cells. HUVECs or HCAECs were seeded inside transwell inserts at a density of 5000 cells/cm$^2$ (23,000 cells/insert) and hUTC lot#120304 or MSCs onto the bottom of a E-well tissue culture dish at a density of 5000 cells/cm$^2$ (48,000 cells/well) in co-culture media (Hayflick 50%+EGM-2MV 50%). After 7 days of co-culture, cells that were on the underside of the transwell insert were harvested and counted using a Guava® instrument. Endothelial cells were also maintained in EGM-2MV media as control. A, HUVECs. B, HCAECs.
Figure 4:
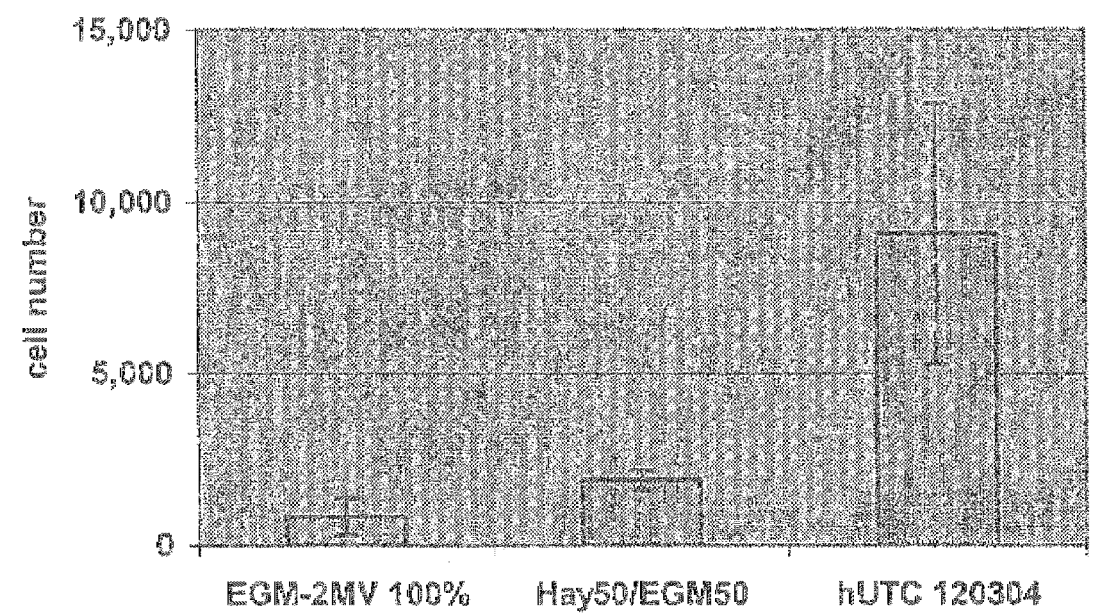

The migration of endothelial cells was assessed by determining the number of cells that have moved through a transwell membrane (pore size=8 microns). The responder cells, endothelial cells, were seeded onto 6-well transwell inserts and hUTCs were plated on the bottom of the well. After a period of co-culture, cells that were on the underside of the transwell were harvested and counted. FIG. 4A shows the migration of HUVECs that were co-cultured with hUTCs and MSCs. hUTC lot#120304 induced the movement of HUVECs to the underside of the transwell while MSCs did not (FIG. 4A). The same result was observed with HCAECs where co-culture with hUTC lot#120304 resulted in more cells migrating through the transwell relative to media control (FIG. 4B).

Figure 5:
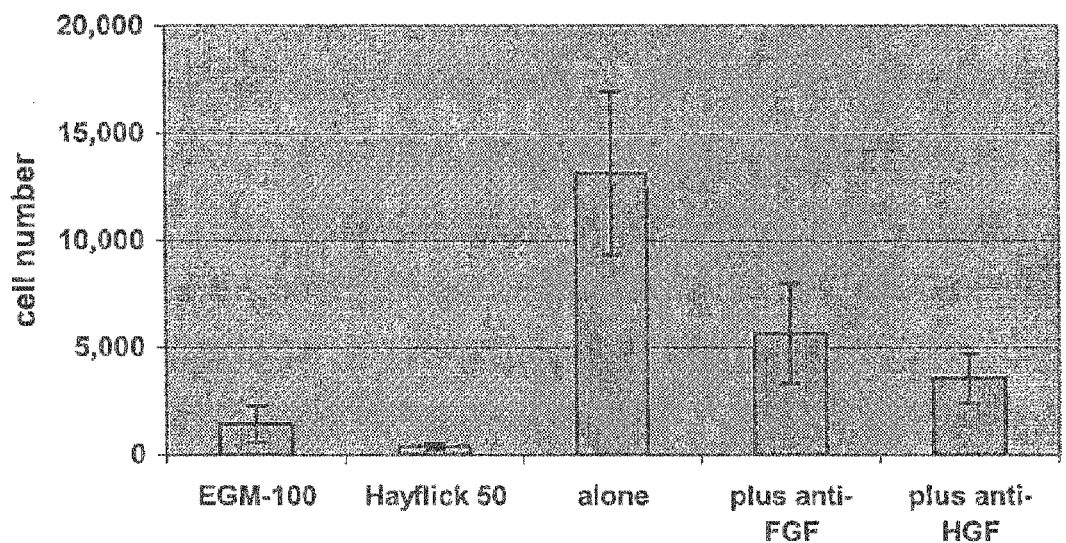
FIG. 5 shows the effect of hUTC lot#120304 and neutralizing antibodies on the migration of endothelial cells. HUVECs or HCAECs were seeded inside transwell inserts at a density of 5000 cells/cm$^2$ (23,000 cells/insert) and hUTC lot#120304 onto the bottom of a 6-well tissue culture dish at a density of 5000 cells/cm$^2$ (48,000 cells/well) in co-culture media (Hayflick 50%+EGM-2MV 50%). Neutralizing antibodies to FGF (7 ng/ml) or HGF (1 ng/ml) were added at this time. After 7 days of co-culture, cells that were on the underside of the transwell insert were harvested and counted using a Guava® instrument. Endothelial cells were also maintained in EGM-2MV media as control. A, HUVECs. B, HCAECs.
Figure 5:
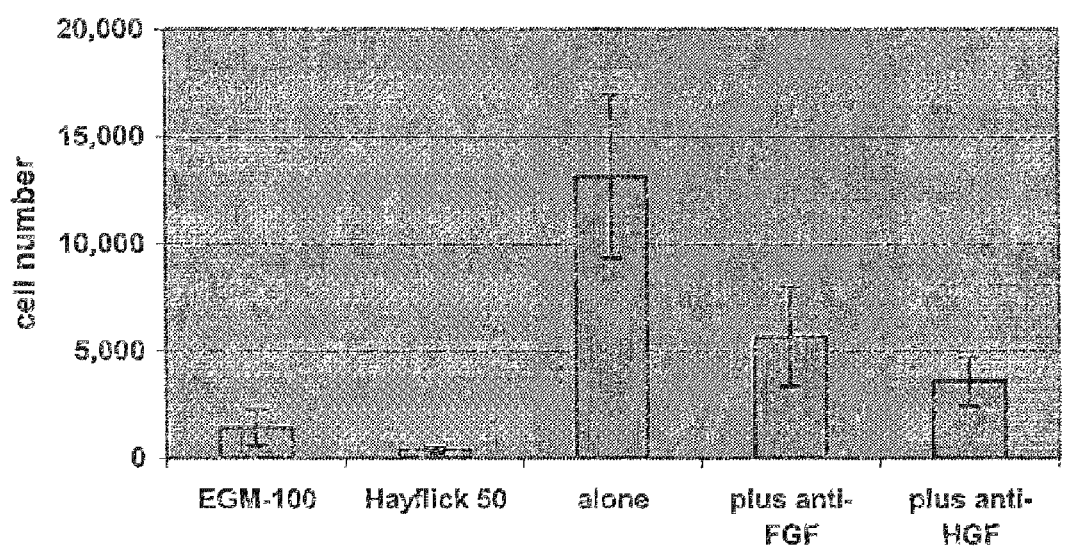

The effect of hUTC lot#120304 on the migratory behavior of HUVECs and HCAECs was further tested with the use of neutralizing antibodies to FGF and HGF. As shown in FIG. 5A, these antibodies reduced the migration of HUVECs induced by hUTC lot#120304. In co-cultures of HCAECs with hUTC lot#120304, a neutralizing antibody to HGF blocked hUTC lot#120304-mediated increase in cell migration while a neutralizing antibody to FGF did not (FIG. 5B).

SUMMARY

The results outlined here describe the effects of hUTCs on the proliferative and migratory behavior of endothelial cells in vitro. The studies were performed using co-cultures of hUTC lot#120304 and endothelial cells or direct incubation of endothelial cells with cell lysate prepared from hUTC lot#120304.

For studies of proliferation, the effects of hUTC lot#120304 were tested and three endothelial cell types from different vascular beds were used as responder cells. Co-culture with hUTCs resulted in enhanced proliferation of endothelial cells. Co-culture with MSCs or fibroblasts resulted in cell numbers comparable to media controls. The proliferative response of HUVECs to hUTC lot#120304 was dampened by the addition of neutralizing antibodies to FGF and HGF, but not by neutralizing antibody to VEGF. This implies that the induction of proliferation by hUTC lot#120304 is mediated by FGF and HGF. It is worth noting that incubation of HUVECs with hUTC lot#120304 lysate mirrored the effect observed with co-cultures.

Migration was quantitated by counting the number of cells that were on the underside of a transwell and both HUVECs and HCAECs were used as responder cells. Unlike the studies with proliferation, the migratory responses of these cells are slightly different. HUTC lot#120304 induced the migration of both HUVECs and HCAECs. MSCs did not induce the migration of HUVECs suggesting specificity of this response to hUTCs. Antibodies to FGF and HGF negated the effect of hUTC lot#120304 on the migration of HUVECs while only antibody to HGF affected the migration of HCAECs suggesting differences between the two endothelial cell types.

In summary, the data show that hUTCs induce proliferation and migration of endothelial cells in vitro. The use of neutralizing antibodies implicates both FGF and HGF in these observed effects. However, other factors may also be involved in the proliferative and migratory behavior of endothelial cells.

EXAMPLE 4

Telomerase Expression in Umbilical-Derived Cells

Telomerase functions to synthesize telomere repeats that serve to protect the integrity of chromosomes and to prolong the replicative life span of cells (Liu, K, et al., *PNAS*, 1999; 96:5147-5152). Telomerase consists of two components, telomerase RNA template (hTER) and telomerase reverse transcriptase (hTERT). Regulation of telomerase is determined by transcription of hTERT but not hTER. Real-time polymerase chain reaction (PCR) for hTERT mRNA thus is an accepted method for determining telomerase activity of cells.

Cell Isolation.

Real-time PCR experiments were performed to determine telomerase production of human umbilical cord tissue-derived cells. Human umbilical cord tissue-derived cells were prepared in accordance the examples set forth above. Generally, umbilical cords obtained from National Disease Research Interchange (Philadelphia, Pa.) following a normal delivery were washed to remove blood and debris and mechanically dissociated. The tissue was then incubated with digestion enzymes including collagenase, dispase and hyaluronidase in culture medium at 37° C. Human umbilical cord tissue-derived cells were cultured according to the methods set forth in the examples above. Mesenchymal stem cells and normal dermal skin fibroblasts (cc-2509 lot #9F0844) were obtained from Cambrex, Walkersville, Md. A pluripotent human testicular embryonal carcinoma (teratoma) cell line nTera-2 cells (NTERA-2 cl.D1), (see, Plaia et al., Stem Cells, 2006; 24(3):531-546) was purchased from ATCC (Manassas, Va.) and was cultured according to the methods set forth above.

Total RNA Isolation.

RNA was extracted from the cells using RNeasy® kit (Qiagen, Valencia, Calif.). RNA was eluted with 50 microliters DEPC-treated water and stored at −80° C. RNA was reverse transcribed using random hexamers with the TaqMan® reverse transcription reagents (Applied Biosystems, Foster City, Calif.) at 25° C. for 10 minutes, 37° C. for 60 minutes and 95° C. for 10 minutes. Samples were stored at −20° C.

Real-Time PCR.

PCR was performed on cDNA samples using the Applied Biosystems Assays-On-Demand™ (also known as TaqMan® Gene Expression Assays) according to the manufacturer's specifications (Applied Biosystems). This commercial kit is widely used to assay for telomerase in human cells. Briefly, hTert (human telomerase gene (Hs00162669) and human GAPDH (an internal control) were mixed with cDNA and TaqMan® Universal PCR master mix using a 7000 sequence detection system with ABI prism 7000 SDS software (Applied Biosystems). Thermal cycle conditions were initially 50° C. for 2 minutes and 95° C. for 10 minutes followed by 40 cycles of 95° C. for 15 seconds and 60° C. for 1 minute. PCR data was analyzed according to the manufacturer's specifications.

Human umbilical cord tissue-derived cells (ATCC Accession No. PTA-6067), fibroblasts, and mesenchymal stem cells were assayed for hTert and 18S RNA. As shown in Table 4-1, hTert, and hence telomerase, was not detected in human umbilical cord tissue-derived cells.

TABLE 4-1

|  | hTert | 18S RNA |
|---|---|---|
| Umbilical cells (022803) | ND | + |
| Fibroblasts | ND | + |

ND—not detected;
+ signal detected

Human umbilical cord tissue-derived cells (isolate 022803, ATCC Accession No. PTA-6067) and nTera-2 cells were assayed and the results showed no expression of the telomerase in two lots of human umbilical cord tissue-derived cells while the teratoma cell line revealed high level of expression (Table 4-2).

TABLE 4-2

|  | hTert | | GAPDH | | |
|---|---|---|---|---|---|
| Cell type | Exp. 1 | Exp. 2 | Exp. 1 | Exp. 2 | hTert norm |
| nTera2 | 25.85 | 27.31 | 16.41 | 16.31 | 0.61 |
| 022803 | — | — | 22.97 | 22.79 | — |

Therefore, it can be concluded that the human umbilical tissue-derived cells of the present invention do not express telomerase.

EXAMPLE 5

Efficacy of hUTC Transplantation in a Murine Model of Hindlimb Ischemia

Previous data demonstrated that systemic administration of hUTC significantly improved blood flow at 5 and 10 days post-treatment in mice with unilateral hindlimb ischemia. In addition, a side-by-side comparative study showed that systemic (intravenous) injection of hUTC resulted in more significant restoration of blood flow compared with local (intramuscular) injection.

This example evaluates the efficacy of intramuscular injection of hUTC and hUTC in fibrin glue in a mouse model of peripheral hindlimb ischemia (unilateral hindlimb ischemia model) Immunocompromised nude and NOD/scid IL2r$\gamma^{-/-}$ (NSG) strains of mice were used.

Animal Model & Description

For the studies in this example, comparisons were made between nude mice and NSG mice.

The NSG mouse strain has generated interest for xenotransplantation studies because of its multiple immunological defects including absence of mature lymphocytes, T cells, B cells, and NK cells. These animals survive longer than 6 months and do not develop thymic lymphomas even after sublethal irradiation (Ito M. et al. (2002) *Blood.* 100: 3175-82).

Unilateral hindlimb ischemia was created in these mice. Briefly, animals were anesthetized by isoflurane inhalation. An incision was made at the midline of the left hindlimb. The femoral artery and its branches were ligated, beginning from the inguinal ligament to the bifurcation of saphenous and popliteal arteries. The regions between the ligatures were excised and the incisions were closed with 5-0 silk Vicryl sutures (Ethicon).

Cells and Fibrin Glue

Frozen cell suspensions were provided by shipment in a dry shipper. Once received, the cells were transferred to liquid nitrogen for long-term storage. Cells were thawed immediately before injection. Cells were counted and viability was determined by trypan blue staining and counting on a hemocytometer. The entire dose was resuspended in PBS and loaded into a 0.3 ml tuberculin syringe with 28 gauge needle for injection.

Fibrin glue (EVICEL® Fibrin sealant (Human), Omrix Pharmaceuticals) was used for these studies. The components were thawed prior to use and diluted to a final concentration of 16-24 IU/ml of thrombin and 39.3-60.7 mg/ml for BAC2 (fibrinogen). Stock solutions of thrombin (stock concentration of approximately 800-1200 IU/ml) and BAC2 (fibrinogen) (stock concentration of approximately 55 to 85 mg/ml) were diluted 1:50 for thrombin and 1:1.4 for BAC2, respectively.

Study Design

A total of forty-eight (48) nude mice (6 to 8-weeks old) and forty-eight (48) NOG/SCID (NSG) mice (6 to 11-weeks old), matched by date of birth, were randomized into the groups as detailed in Table 5-1 below.

TABLE 5-1

| Grp # | Test Animal | # of Animals | Test Material | Cell Dose | Necrosis | Blood Flow by LDI | Capillary density |
|---|---|---|---|---|---|---|---|
| 1 | Nude | 12 | hUTC vehicle | N/A | 1-7 | 1, 7, 14, 21, and 28 | 7 and 28 |
| 2 | Nude | 12 | hUTC | $1 \times 10^6$ | 1-7 | 1, 7, 14, 21, and 28 | 7 and 28 |
| 3 | Nude | 12 | Saline + Fibrin | N/A | 1-7 | 1, 7, 14, 21, and 28 | 7 and 28 |
| 4 | Nude | 12 | Saline + Fibrin + hUTC | $1 \times 10^6$ | 1-7 | 1, 7, 14, 21, and 28 | 7 and 28 |
| 5 | NSG | 12 | hUTC Vehicle | N/A | 1-7 | 1, 7, 14, 21, and 28 | 7 and 28 |
| 6 | NSG | 12 | hUTC | $1 \times 10^6$ | 1-7 | 1, 7, 14, 21, and 28 | 7 and 28 |
| 7 | NSG | 12 | Saline + Fibrin | N/A | 1-7 | 1, 7, 14, 21, and 28 | 7 and 28 |
| 8 | NSG | 12 | Saline + Fibrin + hUTC | $1 \times 10^6$ | 1-7 | 1, 7, 14, 21, and 28 | 7 and 28 |

Endpoint Testing was conducted by measuring the following parameters: Evaluation of blood flow by laser Doppler Imaging on days 1, 7, 14, 21 and 28; assessment of capillary density by CD31 staining on day 7 (3 animals from each group) and day 28.

Method

One day after creation of unilateral hindlimb ischemia, vehicle, hUTC in vehicle, fibrin glue, or hUTC in fibrin glue were injected into the ischemic hindlimb muscle.

For hUTC injections, the specified number of hUTC in vehicle or hUTC in fibrin glue was injected into the ischemic hindlimb muscle. There were three (3×20 µL) injections into the upper limbs and two (2×20 µL) into the lower limbs for a total dose of 100 µl. Control animals received vehicle in the same manner as the cells.

For each injection of hUTC in fibrin glue, cells were resuspended in thrombin (final concentration of 16 to 24 IU/ml). BAC2 (fibrinogen; final concentration of 39.3 to 60.7 mg/ml) was aliquoted into a separate eppendorf tube.

Immediately prior to injection, hUTC in thrombin were transferred into the tube containing BAC2, mixed, and drawn into a 0.3 ml tuberculin syringe (with 28 gauge needle) and injected into the mouse hindlimb. The 100 µL was delivered in five 20 µl intramuscular (IM) injections-3 injections into the upper hindlimb and 2 into the lower hindlimb. Control animals received fibrin glue delivered in the same manner as the cells.

Statistical Analysis

Data are expressed as mean±standard error of the mean. Comparisons between groups were performed with a two-tailed Student's t test.

Evaluation of Blood Flow

Blood perfusion in mice hindlimbs was evaluated using laser Doppler imaging with a Moor LDI device. Animals were anesthetized by isoflurane inhalation and will be placed on a heating pad set at 37° C. To establish baseline ischemia, blood perfusion data in plantar region of both hindlimbs was collected at 24 hours after creation of injury. Serial perfusion assessment was performed at days 7, 14, 21 and 28. Data is reported as a ratio of perfusion values in the left (ischemic) versus right (non-ischemic) limbs.

Results and Analysis

Laser Doppler Perfusion Imagining

Figure 6:
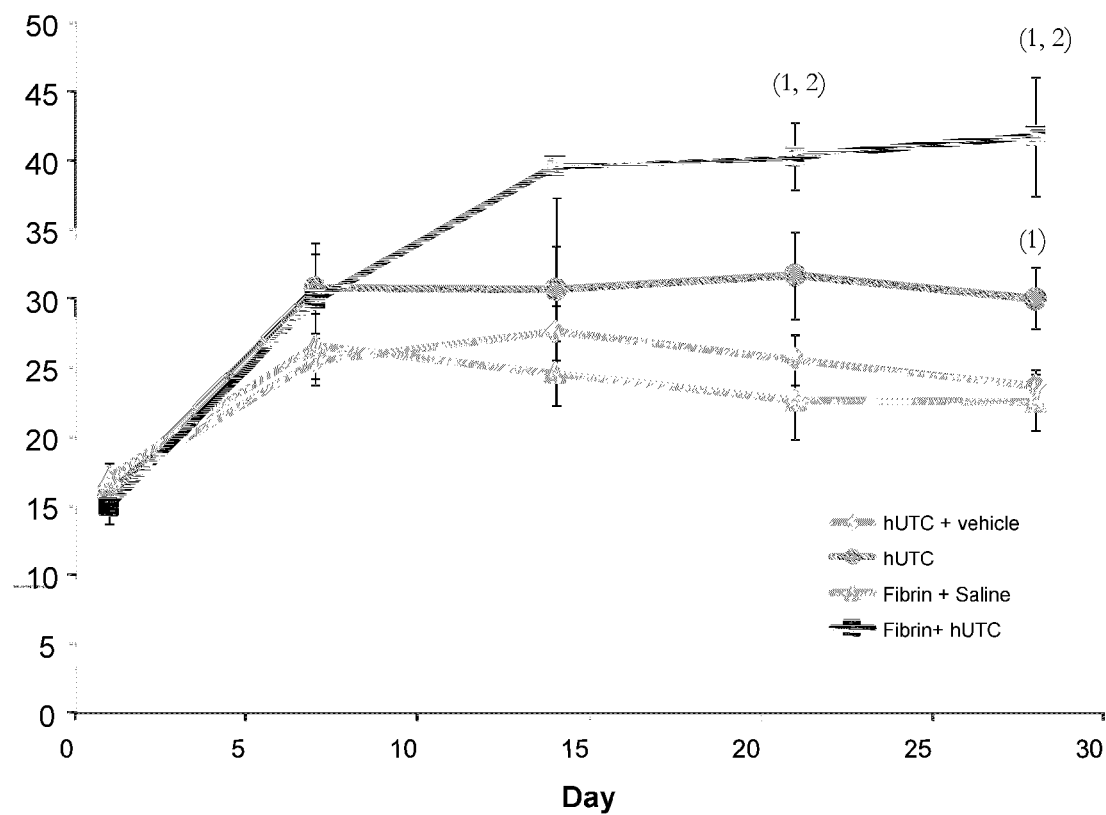
FIG. 6 shows the laser doppler perfusion data from the experiment with NSG mice for the study disclosed in Example 5. Data are expressed as mean±sem. The identity of data points is displayed in the legend. Numbers in parentheses are (1) P<0.001 compared to appropriate control; (2) P<0.05 compared to hUTC cells without fibrin.

Laser Doppler perfusion data (expressed as percentage of perfusion in the ischemic left limb compared to the non-ischemic control right limb) for NSG mice is shown in FIG. 6 and Table 5-2 (below). The largest treatment effect was observed with hUTC delivered in fibrin matrix; relative perfusion in these mice was nearly double the fibrin control group by 21 days (40.3±2.43 vs. 22.6±2.34). At 21 and 28 days this effect was significantly greater than both control groups (P<0.001) as well as the group which received hUTC delivered in vehicle alone (P<0.05). The effect of hUTC delivered in vehicle on relative perfusion was 27% greater than control at 28 days (P<0.05). At this time point relative perfusion in the ischemic limb of NSG mice treated with hUTC in vehicle alone was 30.0±2.3 compared to 23.7±1.6 for mice treated with only vehicle.

TABLE 5-2

Means ± sems for relative perfusion values in NSG mice.

| Agent | Day | | | | |
|---|---|---|---|---|---|
| | 1 | 7 | 14 | 21 | 28 |
| vehicle | 16.5 ± 0.9 | 25.4 ± 1.7 | 27.5 ± 1.9 | 25.6 ± 1.8 | 23.7 ± 1.6 |
| hUTC | 15.7 ± 1.1 | 30.8 ± 3.3 | 30.6 ± 3.1 | 31.7 ± 3.1 | 30.0 ± 2.3 |
| saline + fibrin | 17.0 ± 1.1 | 26.5 ± 2.4 | 24.6 ± 2.3 | 22.6 ± 2.3 | 22.5 ± 2.0 |
| Fibrin + hUTC | 14.9 ± 1.2 | 29.9 ± 3.4 | 39.6 ± 7.5 | 40.3 ± 2.4 | 41.8 ± 4.3 |

Average ± sem

Figure 7:
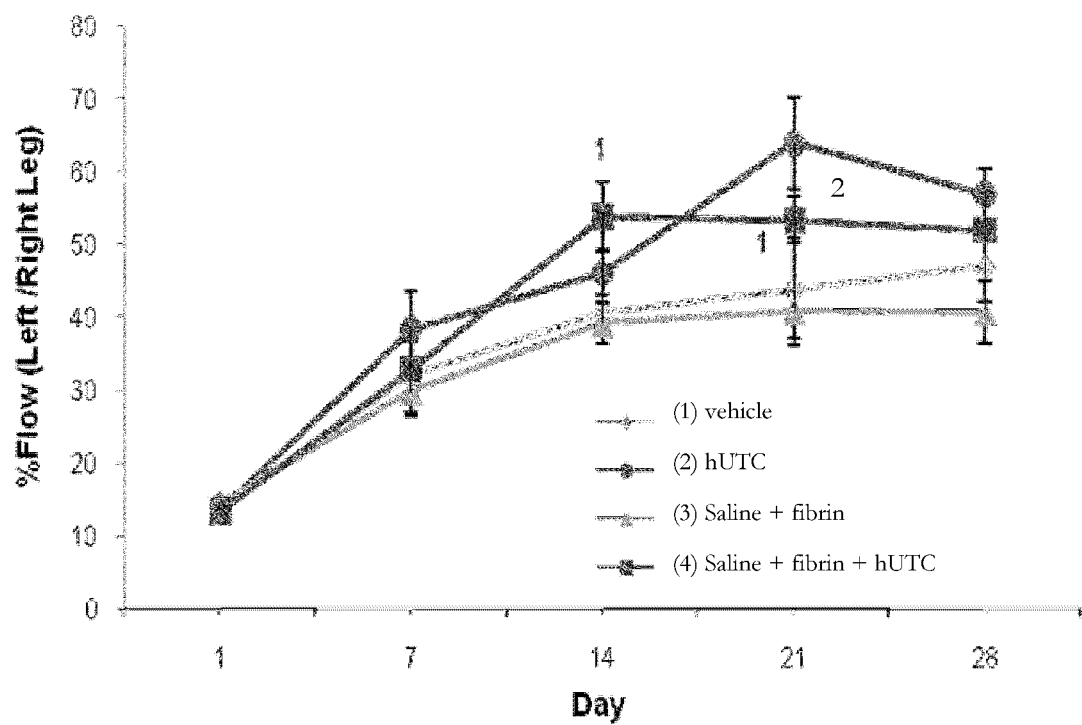
FIG. 7 shows the laser doppler perfusion data from the experiment with nude mice for the study disclosed in Example 5. Data are expressed as mean±sem. The identity of data points is displayed in the legend. Numbers in parentheses are (1) P<0.001 compared to appropriate control; (2) P<0.05 compared to hUTC cells without fibrin.

Perfusion data for nude mice is shown in FIG. 7 and Table 5-3. Treatment with hUTC in fibrin significantly (P<0.05) increased perfusion in the ischemic limb at days 14

(53.9±4.7) and 21 (53.4±3.2) compared to fibrin only treated controls (39.2±1.7 and 40.9±3.7, respectively). The effect of cells in fibrin trended higher at 28 days (52.0±5.8) compared to control (40.8±4.3) but was not significant due to a large deviation in measurements between animals. Local delivery of hUTC in vehicle only trended toward enhanced perfusion at 21 days (64.0±6.3 vs. 43.7±7.4 for the control) and significantly ($P<0.05$) enhanced perfusion by 28 days (52.0±3.5 vs. 40.8±4.9). There was not a significant difference between effects with hUTC delivered in fibrin or vehicle only.

TABLE 5-3

Means ± sems for relative perfusion values in nude mice.

| Agent | Day 1 | 7 | 14 | 21 | 28 |
|---|---|---|---|---|---|
| vehicle | 13.9 ± 1.1 | 32.0 ± 5.1 | 40.6 ± 1.7 | 43.7 ± 7.4 | 47.1 ± 4.9 |
| hUTC | 13.7 ± 0.6 | 38.4 ± 5.1 | 46.1 ± 3.0 | 64.0 ± 6.3 | 57.0 ± 3.5 |
| saline + fibrin | 14.5 ± 0.84 | 29.9 ± 3.5 | 39.2 ± 2.7 | 40.1 ± 3.7 | 40.8 ± 4.3 |
| Fibrin + hUTC | 13.4 ± 0.69 | 33.0 ± 3.7 | 54.9 ± 4.7 | 53.4 ± 3.2 | 52.0 ± 5.8 |

Average ± sem

These data indicate that in both NSG and nude mouse strains hUTC delivered locally by IM injection had early effects when admixed in fibrin carrier. In NSG mice the sustained effect was significantly more pronounced than delivery of cells in vehicle alone.

CONCLUSION

Direct intramuscular administration of hUTC 1 day after creating ischemia enhanced reperfusion of ischemic muscles in both NSG and nude mice. Delivery of the cells in a fibrin matrix to NSG mice appeared to produce a response which was superior to delivery of cells in vehicle alone. Animals treated with direct intramuscular administration of hUTC in a murine hindlimb model of peripheral ischemia showed an enhanced reperfusion of ischemic limbs in both NSG and nude mice. However, animals that were treated with hUTC in fibrin glue exhibited a more significant and sustained response compared to delivery of cells in vehicle alone in the NSG mice.

EXAMPLE 6

Efficacy of hUTC Transplantation in the NOD/Scid IL2r$\gamma^{-/-}$ Mouse Model of Peripheral Limb Ischemia: Dose and Route of Administration Studies This study evaluated the efficacy of hUTC in a mouse model of peripheral hindlimb ischemia (unilateral hindlimb ischemia model). For this study, the NOD/scid IL2r$\gamma^{-/-}$ (NSG) strain of mice was used. The effect on restoration of blood flow was assessed when hUTC were delivered (1) locally (intramuscular) with vehicle, (2) locally (intramuscular) with fibrin glue, or (3) systemically (intravenous). The study also assessed the effect of hUTC administered intramuscularly at different doses with or without fibrin glue, on restoration of blood flow.

Materials and Methods

Animal Model & Description

NSG mice were used. The NSG mouse strain has generated interest for xenotransplantation studies because of its multiple immunological defects including absence of mature lymphocytes, T cells, B cells, and NK cells. These animals survive longer than 6 months and do not develop thymic lymphomas even after sublethal irradiation (Ito M. et al. (2002) *Blood.* 100: 3175-82).

Unilateral hindlimb ischemia was created in these mice. Briefly, animals were anesthetized by isoflurane inhalation. An incision was made at the midline of the left hindlimb. The femoral artery and its branches were ligated, beginning from the inguinal ligament to the bifurcation of saphenous and popliteal arteries. The region between the ligatures was excised and the incision was closed with 5-0 silk Vicryl sutures.

Cells and Fibrin Glue

Cryopreserved hUTC were thawed immediately before injection. Cells were counted and viability was determined by trypan blue staining and counting on a hemocytometer. The entire dose was resuspended in either vehicle or fibrin glue and loaded into a 0.3 ml tuberculin syringe with 28 gauge needle for injection.

Fibrin glue (EVICEL® Fibrin sealant [Human], Omrix Pharmaceuticals) was used. The components were thawed prior to use and diluted to a final concentration of 16 to 24 IU/ml of thrombin and 39.3 to 60.7 mg/ml for BAC2. Stock solutions of thrombin (stock concentration of approximately 800-1200 IU/ml) and BAC2 (fibrinogen) (stock concentration of approximately 55 to 85 mg/ml) were provided and diluted 1:50 for thrombin and 1:1.4 for BAC2, respectively.

Study Design

NSG mice (6 to 11 weeks old), matched by date of birth, were randomized into the groups as detailed in Table 6-1 below:

TABLE 6-1

| Group | #/Group | Test Material | Total Cells Delivered | ROA | Blood Flow by LDI |
|---|---|---|---|---|---|
| 1 | 12 | Vehicle | N/A | IM | 1, 7, 14, 21, and 28 |
| 2 | 12 | hUTC | 1 × 10$^6$ | IM | 1, 7, 14, 21, and 28 |
| 3 | 12 | hUTC | 0.5 × 10$^6$ | IM | 1, 7, 14, 21, and 28 |
| 4 | 12 | Vehicle + Fibrin | N/A | IM | 1, 7, 14, 21, and 28 |
| 5 | 12 | Vehicle + Fibrin + hUTC | 1 × 10$^6$ | IM | 1, 7, 14, 21, and 28 |
| 6 | 12 | Vehicle + Fibrin + hUTC | 0.5 × 10$^6$ | IM | 1, 7, 14, 21, and 28 |
| 7 | 12 | Vehicle + Fibrin + hUTC | 0.25 × 10$^6$ | IM | 1, 7, 14, 21, and 28 |
| 8 | 12 | Vehicle + Fibrin + hUTC | 0.125 × 10$^6$ | IM | 1, 7, 14, 21, and 28 |
| 9 | 12 | Vehicle | N/A | IV | 1, 7, 14, 21, and 28 |
| 10 | 12 | hUTC | 1 × 10$^6$ | IV | 1, 7, 14, 21, and 28 |

One day after creation of unilateral hindlimb ischemia, hUTC were injected either systemically or locally. For systemic injections, the specified number of hUTC in 100 μL of vehicle was administered through the tail vein using a 0.3 cc insulin syringe and a 28-gauge needle. Cell injections were performed over a period of approximately 1 minute. Control animals received vehicle only.

For local injections, the specified number of hUTC in vehicle or hUTC in fibrin glue was injected into the ischemic hindlimb muscle. Injections were made into 5 sites; each delivered 20 μl intramuscular (IM) injections. There were three injections (3×20 μl) injections into the upper limbs and two (2×20 μl) into the lower limbs for a total dose of 100 μL. Control animals received vehicle in the same manner as the cells.

For each injection of hUTC in fibrin glue, cells were resuspended in thrombin (final concentration of 16 to 24 IU/ml). BAC2 (fibrinogen; final concentration of 39.3 to 60.7 mg/ml) was aliquoted into a separate eppendorf tube. Immediately prior to injection, hUTC in thrombin were transferred into the tube containing BAC2, mixed, and drawn into a 0.3 ml tuberculin syringe (with 28 gauge needle) and injected into the mouse hindlimb. The 100 μl dose was delivered in five 20 μl intramuscular (IM) injections-3 injections into the upper hindlimb and 2 into the lower hindlimb. Control animals received fibrin glue delivered in the same manner as the cells.

Evaluation of Blood Flow

Blood perfusion in mice hindlimbs was evaluated using laser Doppler imaging with a Moor LDI device. Animals were anesthetized by isoflurane inhalation and were placed on a heating pad set at 37° C. To establish baseline ischemia, blood perfusion data in plantar region of both hindlimbs was collected at 24 hours after creation of injury. Serial perfusion assessment was performed at days 7, 14, 21 and 28 post-injury. Data is reported as a ratio of perfusion values in the left (ischemic) versus right (non-ischemic) limbs.

Results

Figure 8:
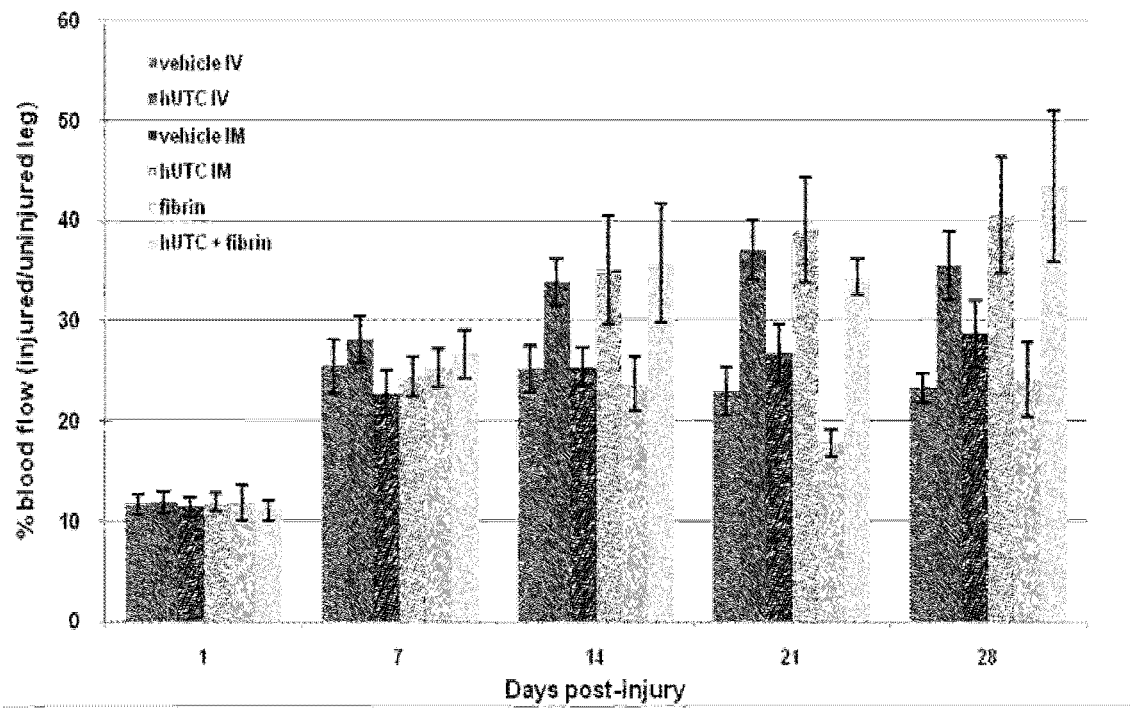
FIG. 8 shows laser doppler perfusion data comparing systemic (IV), local (IM), and local+fibrin glue delivery for the study disclosed in Example 6. Data are expressed as mean±sem.

The mean (±sem) values for relative perfusion in the ischemic limbs for each group are displayed in Table 6-2 (shown below). Two-way ANOVA statistical analysis was conducted on the three sets of data (e.g., IM (no fibrin), IM with fibrin and IV (no fibrin)) using a 5% significance level. Overall effects of time and treatment were evaluated. There was a significant effect (P<0.01) of treatment and time in all groups. A Bonferroni post-test was performed to compare all groups to control and each other within each set (e.g., IM, IM with fibrin and IV).

relative perfusion of 40.6% (see FIG. 8). For cells delivered systemically, relative perfusion in the ischemic limbs of mice receiving hUTC was significantly greater than the control on days 21 and 28 post-injury (P<0.01).

Two doses of cells were tested using local (IM) administration. The higher dose was significantly different (P<0.05) than the control at 21 and 28 days post-injury. The low dose group was not significantly different than control at any day. The high and low dose groups were not significantly different from each other at any time point (Table 6-2).

Figure 9:
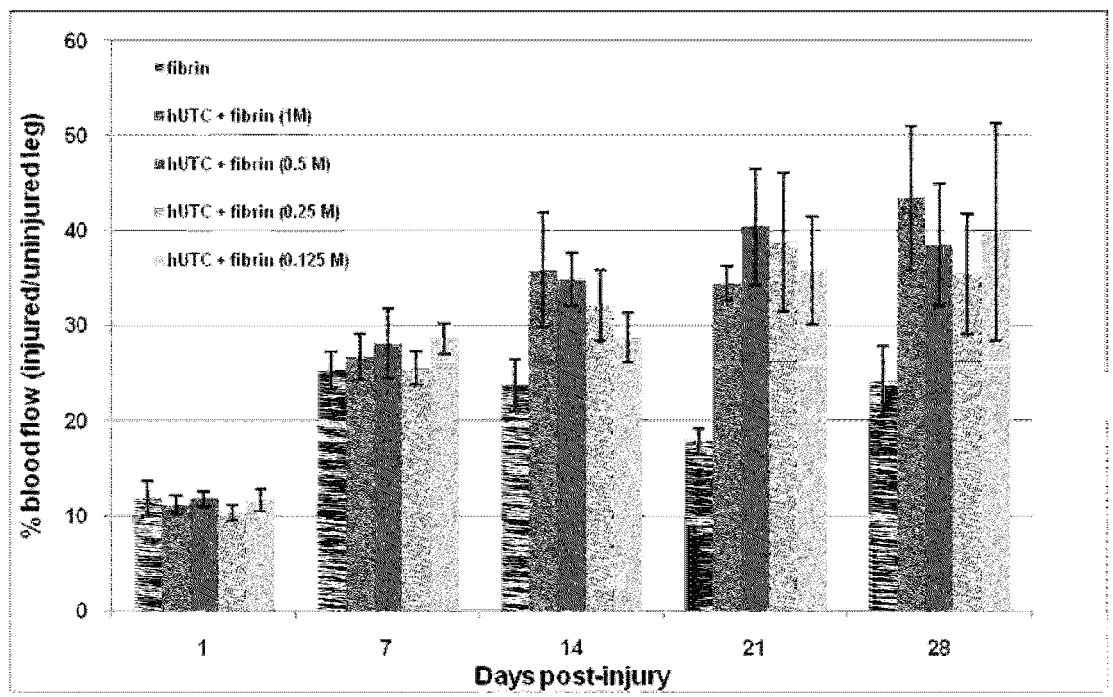
FIG. 9 shows laser doppler perfusion data showing different doses of hUTC in fibrin glue delivered locally (IM) for the study disclosed in Example 6. Data are expressed as mean±sem.

Four different doses of hUTC in fibrin glue were tested using local (IM) administration. In the group receiving $1 \times 10^6$ cells, relative perfusion in the ischemic limb was significantly greater than the control on days 21 (P<0.05) and 28 (P<0.01) post-injury. Relative perfusion in the groups receiving doses of 0.5, 0.25 and $0.125 \times 10^6$ cells were all significantly greater than the control only at day 21 (P<0.001, P<0.01 and P<0.05, respectively) post-injury. There was no difference between any of the dose groups (FIG. 9).

Figure 10:
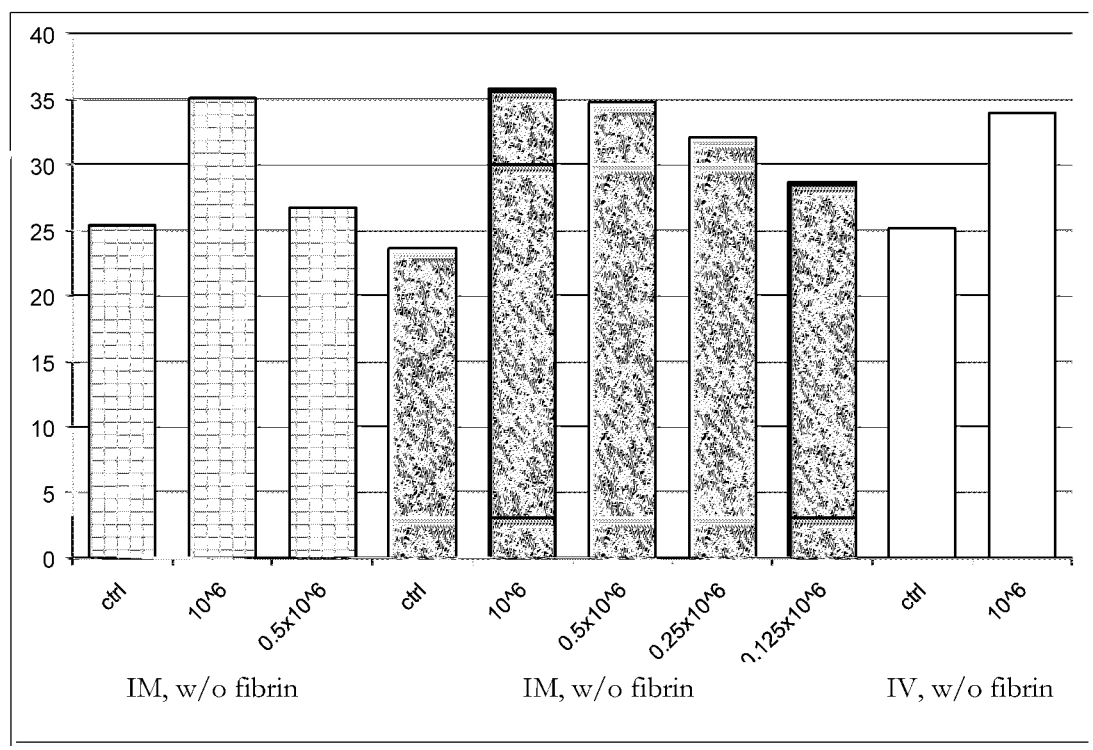
FIG. 10 shows laser doppler perfusion data comparing systemic (IV), local (IM), and local+fibrin glue delivery at 14 days post-injury for the study disclosed in Example 6. Data shown as mean for clarity.

There was a slight trend toward greater reperfusion with increasing dose, which is especially apparent at 14 days post-injury (data without error bars shown for clarity in FIG. 10).

In summary, animals treated with hUTC delivered by all three methods showed increased reperfusion of ischemic limbs. In this study, there was no clear difference in the magnitude of effects with delivery modality. It is notable that the relative perfusion was significantly higher at 28 days post-injury for the highest dose groups; independent of delivery route or cell number.

EXAMPLE 7

Evaluation of the Efficacy of hUTC Cell Transplantation in a Mouse Model of Peripheral Limb Ischemia: A Route of Administration Study The purpose of this study was to evaluate if hUTC cell delivery restores blood flow in a mouse model of peripheral

TABLE 6-2

Summary of laser Doppler imaging data.

| | | | | Day | | | | | | | | |
|---|---|---|---|---|---|---|---|---|---|---|---|---|
| | | | | 1 | | 7 | | 14 | | 21 | | 28 | |
| Group | Treatment | Cell Dose | ROA | mean | sem | mean | sem | mean | sem | mean | sem | mean | sem |
| 1 | Vehicle | N/A | IM | 11.4 | 1.0 | 22.8 | 2.2 | 25.4 | 1.9 | 26.8 | 2.8 | 28.1 | 3.3 |
| 2 | hUTC | $1 \times 10^6$ | IM | 11.9 | 0.9 | 24.4 | 2.0 | 35.1 | 5.4 | *39.1* | 5.3 | *40.6* | 5.8 |
| 3 | hUTC | $0.5 \times 10^6$ | IM | 12.4 | 1.3 | 26.7 | 2.4 | 26.7 | 2.0 | 35.3 | 4.0 | 36.7 | 3.1 |
| 4 | Vehicle + Fibrin | N/A | IM | 11.8 | 1.8 | 25.3 | 1.9 | 23.7 | 2.7 | 17.8 | 1.4 | 24.1 | 3.7 |
| 5 | Vehicle + Fibrin + hUTC | $1 \times 10^6$ | IM | 11.1 | 1.0 | 26.7 | 2.4 | 35.8 | 6.0 | *34.4* | 1.8 | *43.4* | 7.6 |
| 6 | Vehicle + Fibrin + hUTC | $0.5 \times 10^6$ | IM | 11.8 | 0.8 | 28.1 | 3.6 | 34.8 | 2.8 | *40.4* | 6.1 | 38.5 | 6.5 |
| 7 | Vehicle + Fibrin + hUTC | $0.25 \times 10^6$ | IM | 10.3 | 0.8 | 25.5 | 1.7 | 32.1 | 3.7 | *38.8* | 7.3 | 35.4 | 6.3 |
| 8 | Vehicle + Fibrin + hUTC | $0.125 \times 10^6$ | IM | 11.6 | 1.2 | 28.6 | 1.6 | 28.7 | 2.6 | *35.8* | 5.7 | 39.8 | 11.4 |
| 9 | Vehicle | N/A | IV | 11.7 | 1.0 | 25.5 | 2.7 | 25.2 | 2.3 | 22.9 | 2.4 | 23.3 | 1.5 |
| 10 | hUTC | $1 \times 10^6$ | IV | 11.9 | 1.1 | 28.1 | 2.3 | 33.9 | 2.3 | *37.1* | 3.0 | *35.6* | 3.4 |

Mean ± standard errors (sem) for the measurements for specific days (post-injury) are shown.
Bold and italicized numbers indicate statistical significance compared to control.

There was no clear difference in the magnitude of effects with the 3 different delivery modalities. Using $1 \times 10^6$ hUTC in fibrin resulted in approximately 43.4% relative perfusion at 28 days post-injury while hUTC alone resulted in a maximum limb ischemia (unilateral hindlimb ischemia model). A comparison was made between two routes of administration—intravenous and intramuscular delivery; the latter which also included suspension of cells in a fibrin matrix.

Methods

The treatment groups are shown in Table 7-1 below:

TABLE 7-1

Treatment Groups

| Grp # | Test Animal | # of Animals | Test Material | ROA | Cell Dose |
|---|---|---|---|---|---|
| 1 | Nude | 12 | Saline | IV | N/A |
| 2 | Nude | 12 | hUTC | IV | $1 \times 10^6$ |
| 3 | Nude | 12 | Saline | IM | N/A |
| 4 | Nude | 12 | Saline + hUTC | IM | $1 \times 10^6$ |
| 5 | Nude | 12 | Saline + Fibrin | IM | N/A |
| 6 | Nude | 12 | Saline + Fibrin + hUTC | IM | $1 \times 10^6$ |

The fibrin glue formations for Groups 5 and 6, IM administration are shown below in Table 7-2:

TABLE 7-2

Fibrin glue formations for Groups 5 and 6, IM administration

|  | Group 5 | Group 6 |
|---|---|---|
| Cells | None | $1 \times 10^6$ |
| Saline (PBS) | 0.075 ml | 0.075 ml |
| Solution A (thrombin) | 0.0125 ml | 0.0125 ml |
| Solution B (fibrinogen) | 0.0125 ml | 0.0125 ml |

All amounts shown are per animal (0.1 ml per animal)
Thrombin = 1:5000 final dilution of stock solution (stock solution contains 1.6 µl thrombin (800-1200 IU/ml)) + 998.4 µl PBS
Fibrinogen = 1:8 dilution (stock solution is 55-85 mg/ml)

Male immunotolerant nude mice (8 to 10 weeks old) underwent surgically-induced unilateral hindlimb ischemia. At 1 day after surgery, blood flow in both hindlimbs was evaluated by laser Doppler perfusion imaging (LDPI). A single dose ($10^6$) of hUTC cells or vehicle control was administered to 6 groups of mice (N=15/group) as shown in the Table 7-1. The route of administration was either IV injection of 100 µl through the tail vein or the same cumulative dose via 20 µl IM injection into the upper (3 sites) and lower (2 sites) skeletal muscle in the ischemic limb. In 2 groups receiving IM injections, a fibrin matrix was also included.

Serial LDPI was performed at 1, 3, 7, 10, 14 and 21 days; the latter being the last day of the study. Swim endurance was evaluated on 3 days before surgery and again at 10 days after surgery. A mouse was judged to reach its limit for swim endurance when unable to rise to the surface within 5 seconds of submerging. The ratio of post-ischemia swim endurance time to the average endurance before ischemia was compared. Post-mortem gastrocnemius muscle tissue samples, obtained from ischemic and normal limbs of 5 mice from each group having reached day 21 of the study, were processed for histological staining of capillaries (CD31/PECAM-1) and arterioles (smooth muscle a actin). Vessel densities were quantitated from digitized images of immuno-stained slides.

Cell engraftment and vessel densities in tissues harvested at 7 days were evaluated. Vessel density analysis at 7 days was deemed not useful given that the separation of mean relative perfusion values for the IV cell treatment and control groups was statistically different at 21 day. Cell engraftment assays were not performed due to technical difficulties with the methods for cell detection.

Evaluation of Blood Flow

Blood flow in mice hindlimb was evaluated using laser Doppler imaging with a Moor LDI device. Animals were anesthetized by isoflurane inhalation and will be placed on a heating pad set at 37° C. To establish baseline ischemia, blood perfusion data in plantar region of both hindlimbs will be collected at 24 hours after creation of injury. Serial perfusion assessment was performed at days 5, 10, 15 and 20. Data was reported as a ratio of perfusion values in the left (ischemic) versus right (non-ischemic) limbs.

Swimming Endurance Testing

Mice were also monitored for ability to swim or stay afloat in a swimming chamber. To do this, mice were trained to stay afloat in the swimming chamber. Mice were trained everyday for 3 days. At the end of this period, mice were assessed according to the length of time they stay afloat until fatigue, defined as the failure to rise to the surface of the water to breathe within 7-10s (baseline, −3 days). At day 0, mice were subjected to unilateral hindlimb injury and cells were administered 24 hours post-injury. The animals were then assessed for their swimming ability/floating endurance on days 10 and 15.

Results and Analysis

Attrition of animals due to limb necrosis was low in all groups. All attrition occurred by 1 week. The numbers of mice in each group that were removed from the study (shown in parentheses) were: Group 1 (2); Group 2 (1); Group 3 (2); Group 4 (2); Group 5 (1); and Group 6 (2).

Laser Doppler Perfusion Imaging

Figure 11:
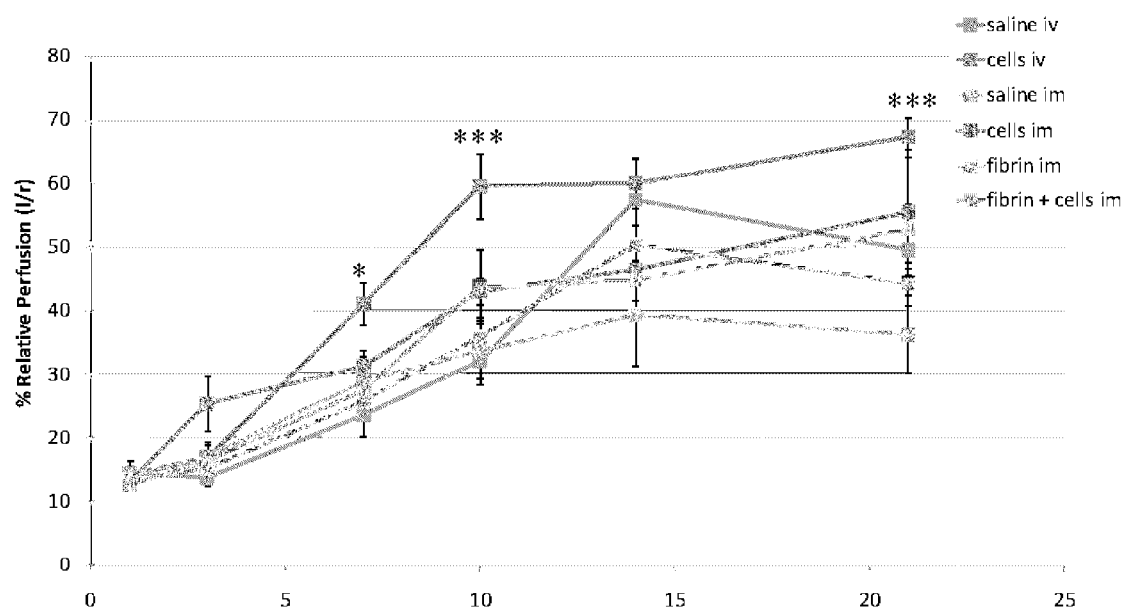
FIG. 11 shows laser doppler perfusion for the study disclosed in Example 7. The identity of data points is displayed in the legend. *, P<0.05; ***, P<0.001.

Laser Doppler perfusion data (expressed as percentage of perfusion in the ischemic left limb compared to the non-ischemic control right limb) is shown in FIG. 11 and Table 7-3. There was enhanced relative reperfusion in the mice treated by IV infusion of hUTC cells compared the control which received saline by IV infusion. This effect was significant at days 7, 10 and 21. There was no significant difference between any of the other treatment groups and the appropriate controls. An unexplained maximum in relative perfusion in all control group animals occurred at 14 days. By 21 days, the values in the control animals had decreased. The relative perfusion values at day 14 of 2 mice in the IV control group were excluded based on relative values which were greater than 100%. Even with these exclusions, there was no difference between the IV cell group and control at this time point.

TABLE 7-3

Means ± sems for relative perfusion values

| Dose | Day | | | | | |
| --- | --- | --- | --- | --- | --- | --- |
|  | 1 | 3 | 7 | 10 | 14 | 21 |
| saline iv | 14.41 ± 0.85 | 1363 ± 1.16 | 23.57 ± 3.39 | 32.07 ± 2.80 | 57.29 ± 6.64* | 49.53 ± 2.86 |
| cells iv | 14.19 ± 2.18 | 16.63 ± 2.18 | 41.07 ± 3.34 | 59.46 ± 5.10 | 59.92 ± 3.93 | 67.24 ± 3.18 |
| saline im | 1422 ± 1.39 | 16.98 ± 2.39 | 28.82 ± 3.99 | 33.66 ± 5.29 | 39.34 ± 8.14 | 36.21 ± 6.14 |

TABLE 7-3-continued

| | Means ± sems for relative perfusion values | | | | | |
|---|---|---|---|---|---|---|
| | Day | | | | | |
| Dose | 1 | 3 | 7 | 10 | 14 | 21 |
| cells im | 12.98 ± 0.71 | 25.32 ± 4.33 | 31.13 ± 2.58 | 42.95 ± 2.00 | 46.34 ± 1.66 | 55.43 ± 9.84 |
| fibrin im | 13.15 ± 1.01 | 15.16 ± 2.08 | 25.64 ± 2.82 | 35.99 ± 2.51 | 50.35 ± 3.03 | 44.20 ± 3.4 |
| fibrin + cells im | 12.47 ± 0.70 | 16.34 ± 1.73 | 27.49 ± 1.73 | 43.76 ± 5.84 | 44.73 ± 3.12 | 52.84 ± 3.9 |

*values for 2 mice excluded based on ischemic limb value >100% control limb

Figure 12:
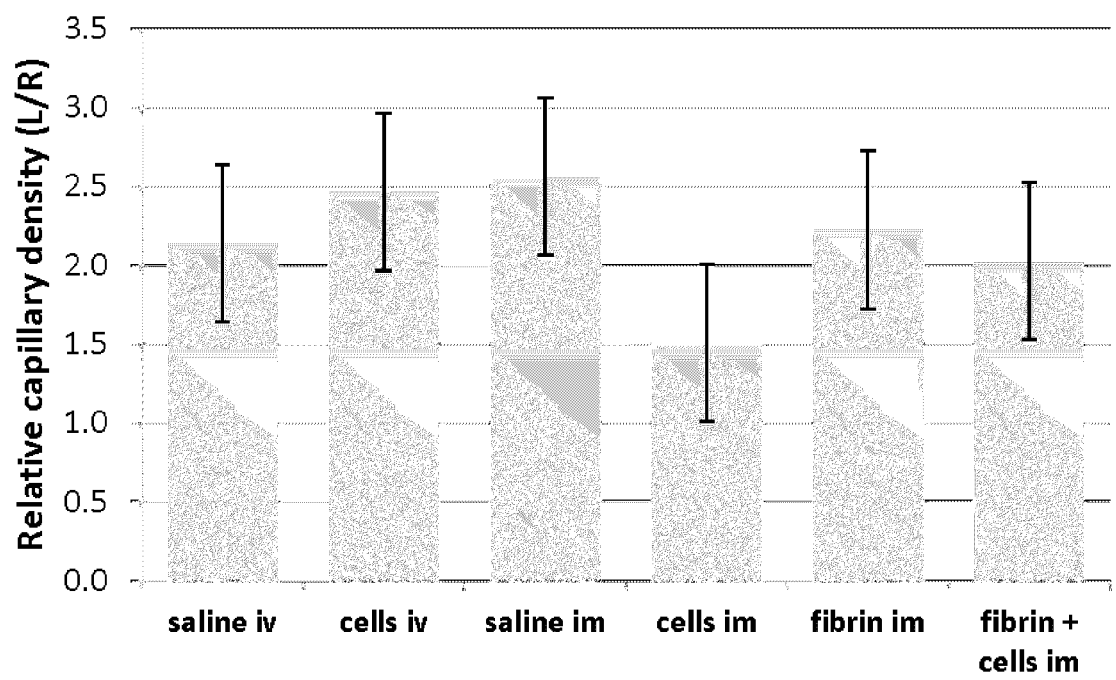
FIG. 12 shows capillary density of ischemic limbs compared to non-ischemic limbs of mice surviving to 21 days for the study disclosed in Example 7.

Capillary and arteriole densities in both lower limbs were determined in immunohistologically stained thin sections harvested at 21 days. There was no correlation between microvascular density and perfusion. The relative density of capillaries was not significantly different between controls and treated groups (FIG. 12).

Figure 13:
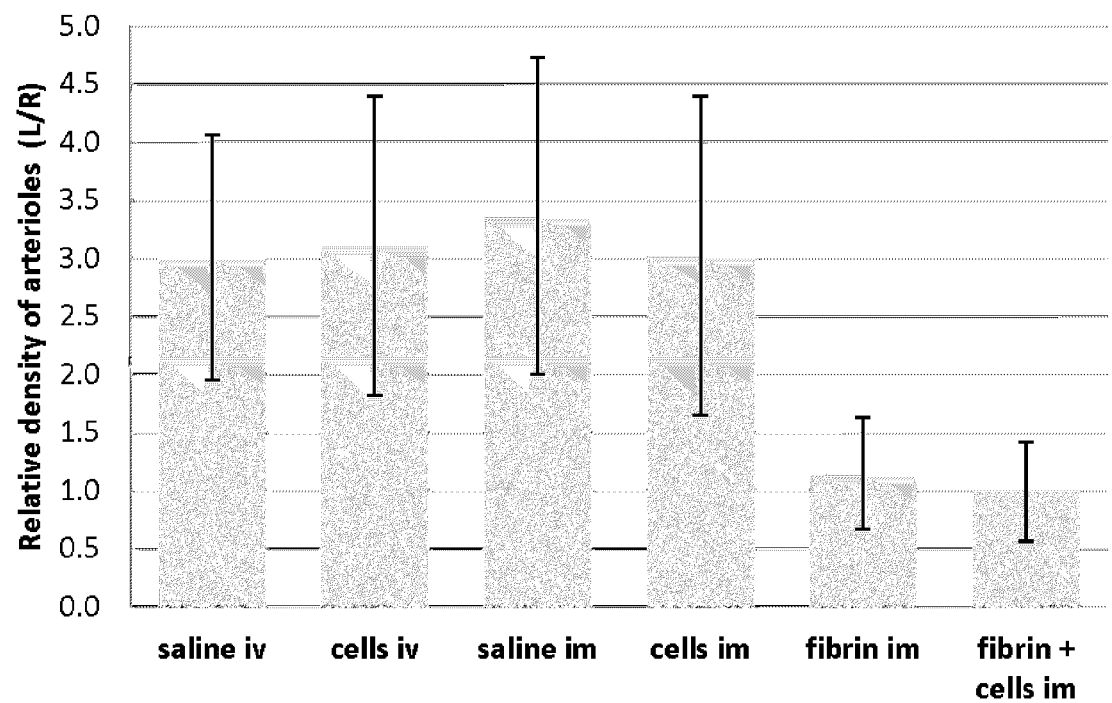
FIG. 13 shows arteriole density ischemic limbs compared to non-ischemic limbs of mice surviving to 21 days for the study disclosed in Example 7.

There was no difference between arteriolar densities of controls and treated animals (FIG. 13). There was a trend toward reduced density of arterioles in the muscles injected directly with fibrin.

The capacity of mice to swim against a laminar flow current was assessed before surgery and again at 10 days after surgery. The total time of swimming was recorded before induction of ischemia each session and compared. There was no significant difference between controls and treatment groups in the functional assessment.

In summary, the results show that intravenous administration of hUTC lead to restoration of blood flow in ischemic muscles on day 3, day 10 and day 21 post-injury. In particular, intravenous administration of hUTC 1 day after creating ischemia resulted in accelerated reperfusion of ischemic muscles and a greater level of relative perfusion at the end of the experiment (21 days). Other treatments did not have an apparent affect by any of the measures used in this study. The mechanism by which IV delivered hUTC enhanced reperfusion was not apparent based on the analysis of vessel regrowth in the ischemic region. It is possible that other mechanisms may explain the observed effects. Recently it has been shown that systemically delivered bone marrow-derived mesenchymal stem cells trap in the lung where they promote protection at a distance via secretion of anti-inflammatory factors which may reduce the degree of earlier injury to the tissues (Lee et al. (2009) *Stem Cell*. 5(1):54-63).

The present invention is not limited to the embodiments described and exemplified above. It is capable of variation and modification within the scope of the appended claims.

What is claimed is:

1. A method of improving blood flow in ischemic tissue in a patient having peripheral ischemia, comprising administering by intramuscular injection or injection into adipose depots in muscle a pharmaceutical composition comprising a pharmaceutically acceptable carrier and a mixture of fibrin and an isolated homogenous population of cells obtained from human umbilical cord tissue in an amount effective to improve blood flow in the ischemic tissue, wherein the umbilical cord tissue is substantially free of blood, and wherein said isolated homogenous population of the cells is capable of self-renewal and expansion in culture, has the potential to differentiate and further has the following characteristics:
   (a) expresses oxidized low density lipoprotein receptor 1, chemokine receptor ligand 3, and granulocyte chemotactic protein;
   (b) does not express CD117, CD31, CD34, or CD45;
   (c) expresses, relative to a human fibroblast, mesenchymal stem cell, or iliac crest bone marrow cell, increased levels of interleukin 8 and reticulon 1;
   (d) has the potential to differentiate into cells of at least a skeletal muscle, vascular smooth muscle, pericyte or vascular endothelium phenotype; and
   (e) expresses CD10, CD13, CD44, CD73, and CD90.

2. The method of claim 1, wherein the pharmaceutical composition is administered at the sites of peripheral ischemia.

3. The method of claim 1, wherein the pharmaceutical composition is administered locally.

4. The method of claim 1, wherein the isolated population of cells is induced in vitro to differentiate into a skeletal muscle, vascular muscle, pericyte or vascular endothelium lineage prior to administration.

5. The method of claim 1, wherein the population of cells is genetically engineered to produce a gene product that promotes treatment of peripheral vascular disease.

6. The method of claim 1, wherein the composition further comprises an agent selected from the group consisting of an antithrombogenic agent, an immunosuppressive agent, an immunomodulatory agent, a pro-angiogenic, an antiapoptotic agent and mixtures thereof.

7. The method of claim 1, wherein the composition further comprises at least one other cell type.

8. The method of claim 7, wherein the other cell type is a skeletal muscle cell, a skeletal muscle progenitor cell, a vascular smooth muscle cell, a vascular smooth muscle progenitor cell, a pericyte, a vascular endothelial cell, a vascular endothelium progenitor cell or other multipotent or pluripotent stem cell.

9. The method of claim 1, wherein the pharmaceutical composition exerts a trophic effect.

10. The method of claim 9, wherein the trophic effect is proliferation of vascular endothelial cells.

11. The method of claim 1, wherein the pharmaceutical composition induces migration of vascular endothelial cells and/or vascular endothelium progenitor cells to the sites of the peripheral disease.

12. The method of claim 1, wherein the pharmaceutical composition induces migration of vascular smooth muscle cells and/or vascular smooth muscle progenitor cells to the sites of the peripheral disease.

13. The method of claim 1, wherein the pharmaceutical composition induces migration of pericytes to the sites of the peripheral vascular disease.

14. A method of improving blood flow in ischemic tissue in a patient having peripheral ischemia, comprising administering by intramuscular injection or injection into adipose depots in muscle a mixture of fibrin and an isolated homogenous population of cells obtained from human umbilical cord tissue in an amount effective to improve blood flow in the ischemic tissue, wherein the umbilical cord tissue is substantially free of blood, and wherein said isolated homogenous population of the cells is capable of self-renewal and expansion in culture, has the potential to differentiate and further has the following characteristics:
- (a) expresses oxidized low density lipoprotein receptor 1, chemokine receptor ligand 3, and granulocyte chemotactic protein;
- (b) does not express CD117, CD31, CD34, or CD45;
- (c) expresses, relative to a human fibroblast, mesenchymal stem cell, or iliac crest bone marrow cell, increased levels of interleukin 8 and reticulon 1;
- (d) has the potential to differentiate into cells of at least a skeletal muscle, vascular smooth muscle, pericyte or vascular endothelium phenotype; and
- (e) expresses CD10, CD13, CD44, CD73, and CD90.

15. The method of claim 14, wherein the mixture of the population of cells and fibrin is administered at the sites of peripheral ischemia.

16. The method of claim 14, wherein the mixture of fibrin glue and the population of cells is administered locally.

17. The method of claim 14, wherein the isolated population of cells is induced in vitro to differentiate into a skeletal muscle, vascular muscle, pericyte or vascular endothelium lineage prior to administration.

18. The method of claim 14, wherein the population of cells is genetically engineered to produce a gene product that promotes treatment of peripheral vascular disease.

19. The method of claim 14, further comprising administration of an agent selected from the group consisting of an antithrombogenic agent, an immunosuppressive agent, an immunomodulatory agent, a pro-angiogenic, an antiapoptotic agent and mixtures thereof.

20. The method of claim 14 further comprising administration of at least one other cell type.

21. The method of claim 20, wherein the other cell type is a skeletal muscle cell, a skeletal muscle progenitor cell, a vascular smooth muscle cell, a vascular smooth muscle progenitor cell, a pericyte, a vascular endothelial cell, a vascular endothelium progenitor cell or other multipotent or pluripotent stem cell.

22. The method of claim 14, wherein the population of cells exerts a trophic effect.

23. The method of claim 21, wherein the trophic effect is proliferation of vascular endothelial cells.

24. The method of claim 14, wherein the population of cells induces migration of vascular endothelial cells and/or vascular endothelium progenitor cells to the sites of the peripheral disease.

25. The method of claim 14, wherein the population of cells induces migration of vascular smooth muscle cells and/or vascular smooth muscle progenitor cells to the sites of the peripheral disease.

26. The method of claim 14, wherein the population of cells induces migration of pericytes to the sites of the peripheral vascular disease.

27. A method of improving blood flow in ischemic tissue in a patient having peripheral ischemia, comprising administering by intramuscular injection or injection into adipose depots in muscle a pharmaceutical composition comprising a pharmaceutically acceptable carrier and a mixture of fibrin glue and an isolated homogenous population of cells obtained from human umbilical cord tissue in an amount effective to improve blood flow in the ischemic tissue, wherein the umbilical cord tissue is substantially free of blood, wherein the fibrin glue comprises from about 16 to about 24 IU/ml of thrombin and from about 39.3 to about 60.7 mg/ml of fibrinogen, and wherein said isolated homogenous population of the cells is capable of self-renewal and expansion in culture, has the potential to differentiate and further has the following characteristics:
- (a) expresses oxidized low density lipoprotein receptor 1, chemokine receptor ligand 3, and granulocyte chemotactic protein;
- (b) does not express CD117, CD31, CD34, or CD45;
- (c) expresses, relative to a human fibroblast, mesenchymal stem cell, or iliac crest bone marrow cell, increased levels of interleukin 8 and reticulon 1;
- (d) has the potential to differentiate into cells of at least a skeletal muscle, vascular smooth muscle, pericyte or vascular endothelium phenotype; and
- (e) expresses CD10, CD13, CD44, CD73, and CD90.

28. A method of improving blood flow in ischemic tissue in a patient having peripheral ischemia, comprising administering by intramuscular injection or injection into adipose depots in muscle a mixture of fibrin glue and an isolated homogenous population of cells obtained from human umbilical cord tissue in an amount effective to improve blood flow in the ischemic tissue, wherein the umbilical cord tissue is substantially free of blood, wherein the fibrin glue comprises from about 16 to about 24 IU/ml of thrombin and from about 39.3 to about 60.7 mg/ml of fibrinogen, and wherein said isolated homogenous population of the cells is capable of self-renewal and expansion in culture, has the potential to differentiate and further has the following characteristics:
- (a) expresses oxidized low density lipoprotein receptor 1, chemokine receptor ligand 3, and granulocyte chemotactic protein;
- (b) does not express CD117, CD31, CD34, or CD45;
- (c) expresses, relative to a human fibroblast, mesenchymal stem cell, or iliac crest bone marrow cell, increased levels of interleukin 8 and reticulon 1;
- (d) has the potential to differentiate into cells of at least a skeletal muscle, vascular smooth muscle, pericyte or vascular endothelium phenotype; and
- (e) expresses CD10, CD13, CD44, CD73, and CD90.

* * * * *